US008357690B2

(12) United States Patent
Armstrong et al.

(10) Patent No.: US 8,357,690 B2
(45) Date of Patent: Jan. 22, 2013

(54) METHODS OF TREATMENT USING COMBINATION THERAPY

(75) Inventors: Robert C. Armstrong, San Diego, CA (US); Barbara A. Belli, San Diego, CA (US)

(73) Assignee: Ambit Biosciences Corporation, San Diego, CA (US)

(*) Notice: Subject to any disclaimer, the term of this patent is extended or adjusted under 35 U.S.C. 154(b) by 340 days.

(21) Appl. No.: 12/730,097

(22) Filed: Mar. 23, 2010

(65) Prior Publication Data

US 2010/0292177 A1 Nov. 18, 2010

Related U.S. Application Data

(60) Provisional application No. 61/202,647, filed on Mar. 23, 2009, provisional application No. 61/173,803, filed on Apr. 29, 2009, provisional application No. 61/266,989, filed on Dec. 4, 2009.

(51) Int. Cl.
*A61K 31/497* (2006.01)

(52) U.S. Cl. .................. 514/254.02; 514/322; 514/366; 544/132; 544/133; 544/368; 546/199

(58) Field of Classification Search .................. None
See application file for complete search history.

(56) References Cited

U.S. PATENT DOCUMENTS

| | | | |
|---|---|---|---|
| 3,350,388 A | 10/1967 | Sorm et al. | |
| 3,817,980 A | 6/1974 | Vorbruggen et al. | |
| 4,751,221 A | 6/1988 | Watanabe et al. | |
| 5,033,252 A | 7/1991 | Carter | |
| 5,052,558 A | 10/1991 | Carter | |
| 5,323,907 A | 6/1994 | Kalvelage | |
| 5,384,310 A | 1/1995 | Montgomery et al. | |
| 6,680,382 B2 | 1/2004 | Bauta et al. | |
| 7,038,038 B2 | 5/2006 | Ionescu et al. | |
| 7,078,518 B2 | 7/2006 | Ionescu et al. | |
| 7,192,781 B2 | 3/2007 | Luna et al. | |
| 7,820,657 B2 * | 10/2010 | Bhagwat et al. | ........... 514/233.2 |
| 2007/0232604 A1 | 10/2007 | Bhagwat et al. | |
| 2008/0057086 A1 | 3/2008 | Etter | |
| 2009/0123418 A1 | 5/2009 | James | |
| 2009/0131426 A1 | 5/2009 | Bhagwat et al. | |

FOREIGN PATENT DOCUMENTS

| | | |
|---|---|---|
| EP | 0816366 | 1/1998 |
| WO | WO 02/076439 | 10/2002 |
| WO | WO 2007/109120 | 9/2007 |
| WO | WO 2009/038757 | 3/2009 |
| WO | WO 2009/061446 | 5/2009 |
| WO | WO 2010/054058 | 5/2010 |
| WO | WO 2010/132787 | 11/2010 |
| WO | WO 2011/056939 | 5/2011 |

OTHER PUBLICATIONS

Ravandi et al. Cancer (2004), vol. 100, pp. 441-454.*
Amidon, et al., Transport Processes in Pharmaceutical Systems Marcell Dekker, 185-218 (2000).
Balant, et al., Eur. J. Drug Metab. Pharmacokinet, 15, 143-153 (1990).
Balimane et al., Adv. Drug Delivery Rev., 39, 183-209 (1999).
Birge, et al., J. Pharm. Sci., 66, pp. 1-19 (1977).
Bundgaard, Arch. Pharm. Chem., 86, 1-39 (1979).
Bundgaard, Controlled Drug Delivery, 17, 179-196 (1987).
Bundgaard, Adv. Drug Delivery Rev., 8, 1-38 (1992).
Browne, Clin. Neuropharmacol, 20, 1-12 (1997).
Cheson et al., Blood 108, 419-425 (2006).
Cheson, et al., J. Clin. Oncol. 21, 4642-4649 (2003).
Chou et al., Adv. Enzyme Regul. 22, 27-55 (1984).
Chou, Pharmacological Reviews, vol. 58, No. 3, pp. 621-681, (2006).
Farquhar, et al., J. Pharm. Sci., 72, 324-325 (1983).
Fleisher, et al., Adv. Drug Delivery Rev., 19, 115-130 (1996).
Fleisher, et al., Methods Enzymol., 112, 360-381 (1985).
Freeman, et al., J. Chem. Soc., Chem. Commun., 875-877 (1991).
Friis, et al., Eur. J. Pharm. Sci., 4, 49-59 (1996).
Wermuth, et al., Pract. Med. Chem, 671-696 (1996).
Gangwar, et al., Des. Biopharm. Prop. Prodrugs Analogs, 409-421 (1977).
Gangwar, et al., Drug Discovery Today 2, 148-155 (1997).
Harper, Progress in Drug Research 4, 221-294, (1962).
Levis, et al., Blood, vol. 104, No. 4, pp. 1145-1150, (2004).
Mizen, et al., Integration of Pharmaceutical Discovery and Development: Case Histories, 11, 345-365 (1998).
Nathwani et al., Drugs, 45, 866-894 (1993).
Pauletti et al., Adv. Drug Delivery Rev., 27, 235-256 (1997).
Sinhababu et al., Adv. Drug Delivery Rev., 19, 241-273 (1996).
Stella, et al., Drug 29, 455-473 (1985).
Tan, et al., Adv. Drug Delivery Rev., 39, 117-151 (1999).
Taylor, Adv. Drug Delivery Rev., 19, 131-148 (1996).
Therasse, et al., Journal of the National Cancer Institute 92, 205-216 (2000).
Yamamoto, et al., Blood 97(8), 2434-2439 (2001).
Wang, et al., Curr. Pharm. Design, 5, 265-287 (1999).
Wiebe et al., Adv. Drug Delivery Rev., 39, 63-80 (1999).
Waller, et al., Br. J. Clin. Pharmac., 28, 497-507 (1989).
Yee, et al., Blood 104 (13), 4202-4209 (2001).
Buchner, et al., Blood, 93 (12), 4116-4124 (1999).
Burnett, et al., Cancer, 109 (6), 1114-1124 (2007).
Clavio, et al., Haematologica 81:513-520 (1996).
Faderl, et al., Blood 105 (3) 940-947 (2004).
Kantarjian, et al., Blood, 102 (7) 2379-2386 (2003).
O'Donnell et al. National Comprehensive Cancer Network Inc., Clinical Practice Guidelines in Oncology Version 1 (2009).
Stone, et al. Abstract #157, Blood, 108 (11) (2006).
Sudan, et al., Cancer, 107 (8) 1839-1843 (2006).
Visani, et al., Bone Marrow Transplantation 27, 829-835 (2001).
Wiernik, et al., Blood 79 (2), 313-319 (1992).
Yates, et al., Blood 60 (2), 454-462 (1982).
Naito Seiji et al., Oncology Research, vol. 10, No. 3, 123-132 (1998).

* cited by examiner

*Primary Examiner* — Patrick Lewis
(74) *Attorney, Agent, or Firm* — Jones Day

(57) ABSTRACT

Provided herein are methods of treating a proliferative disease in a subject, comprising administering to the subject a therapeutically effective amount of AC220 and a nucleoside analog, a topoisomerase inhibitor or an anthracycline, or a combination thereof.

44 Claims, 10 Drawing Sheets

METHODS OF TREATMENT USING COMBINATION THERAPY

RELATED APPLICATIONS

This application claims priority to U.S. provisional application Nos. 61/202,647, filed Mar. 23, 2009; 61/173,803 filed Apr. 29, 2009; and 61/266,989 filed Dec. 4, 2009. The disclosures of the above referenced applications are incorporated by reference herein in their entireties.

FIELD

Provided herein is a combination therapy for treating a proliferative disease. Further provided herein are methods of administering N-(5-tert-butyl-isoxazol-3-yl)-N'-{4-[7-(2-morpholin-4-yl-ethoxy)imidazo[2,1-b][1,3]benzothiazol-2-yl]phenyl}urea, or a pharmaceutically acceptable salt, hydrate, solvate or prodrug thereof, in combination with a chemotherapeutic agent such as a nucleoside analog, an anthracycline, a topoisomerase inhibitor or a combination thereof. In certain embodiments, the methods are for treating a cancer.

BACKGROUND

Cancer has been one of the ten leading causes of death worldwide in recent years. For example, cancer accounted for 7.9 million deaths (around 13% of all deaths) in 2007. According to a 2008 report by the International Agency for Research on Cancer (IARC), a division of the World Health Organization (WHO), the burden of cancer doubled globally between 1975 and 2000, and cancer is expected to become the leading cause of death worldwide in 2010.

Hematological cancers, such as leukemia, lymphoma, multiple myeloma, and other cancers related to blood and blood-producing organs, are the fifth most commonly occurring cancers and the second leading cause of cancer death. Despite the recent development of novel anti-cancer agents, the current therapy of hematological cancers is still dominated by using drugs for the treatment of solid tumors.

N-(5-tert-butyl-isoxazol-3-yl)-N'-{4-[7-(2-morpholin-4-yl-ethoxy)imidazo[2,1-b][1,3]benzothiazol-2-yl]phenyl}urea or AC220 is known for its anti-tumor activity. Treatment of the various cancers with AC220 has been proposed in the literature. Various dosing regimens have been reported, for example, see, U.S. Patent Application Pub. Nos. US 2007/0232604, US 2009/0123418, US 2009/0131426, all of which are incorporated herein by reference in their entirety.

There is a continuing need for developing therapy for proliferative diseases, including cancer.

SUMMARY OF THE DISCLOSURE

In one embodiment, provided herein is a method of treating a proliferative disease comprising co-administering to a patient in need thereof a therapeutically effective amount of (a) a nucleoside analog, an anthracycline, a topoisomerase inhibitor, or a combination thereof; and (b) a compound of structural formula (I) or a salt, solvate, hydrate, ester and/or prodrug thereof. In one embodiment, the nucleoside analog is a neoplastic cell antimetabolite. In one embodiment, provided herein is a method of treating a hematological neoplastic disease comprising co-administering to a patient in need thereof a therapeutically effective amount of (a) a nucleoside analog, wherein the nucleoside analog is a neoplastic cell antimetabolite; an anthracycline; a topoisomerase inhibitor; or a combination thereof; and (b) a compound of structural formula (I) or a salt, solvate, hydrate, ester and/or prodrug thereof.

The compound of formula (I) is:

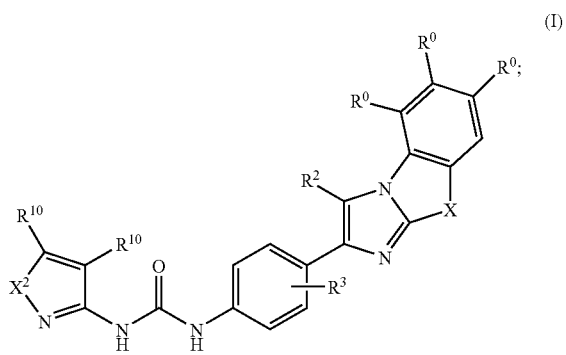

wherein
$X^2$ is —O— or —S—;
X is —S—, —N($R^5$)— or —O—;
two of the three $R^0$ are hydrogen; and the other $R^0$ is halo, hydroxy, optionally substituted alkyl, optionally substituted alkoxy, or

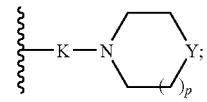

$Y$ is —O—, —S—, —N($R^{14}$)— or —C(H)$R^{15}$—;
$K$ is —O(CH$_2$)$_q$—, —C(O), —C(O)NH(CH$_2$)$_q$—, —(CH$_2$)$_q$O—, or —(CH$_2$)$_q$O(CH$_2$)$_q$—;
p is an integer from 0 to 2;
each q is independently an integer from 1 to 4;
$R^2$ is hydrogen, halo, nitro, cyano, optionally substituted alkyl, —OR$^{12}$, —SR$^{12}$, —N(R$^{12}$)$_2$, —S(O)$_t$R$^{13}$, —C(O)R$^{12}$, —C(O)OR$^{12}$, —C(O)N(R$^{12}$)$_2$, —C(O)SR$^{12}$, or —N(R$^{12}$)S(O)$_t$R$^{13}$;
$R^3$ is hydrogen, halo, nitro, cyano, optionally substituted alkyl, —OR$^{12}$, —SR$^{12}$, —N(R$^{12}$)$_2$, —S(O)$_t$R$^{13}$, —C(O)R$^{12}$, —C(O)OR$^{12}$, —C(O)N(R$^{12}$)$_2$, —C(O)SR$^{12}$, or —N(R$^{12}$)S(O)$_t$R$^{13}$;
$R^5$ is hydrogen or optionally substituted alkyl;
each $R^{10}$ is independently selected from hydrogen, halo, optionally substituted alkyl, optionally substituted cycloalkyl, or optionally substituted aryl;
each $R^{12}$ is independently selected from the group consisting of hydrogen, optionally substituted alkyl, optionally substituted alkenyl, optionally substituted alkynyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl and optionally substituted heteroaralkyl;
$R^{13}$ is optionally substituted alkyl;
$R^{14}$ is hydrogen, optionally substituted alkyl, —C(O)OR$^{12}$, —C(O)SR$^{12}$, —C(O)NR$^{12}$ or —S(O)$_t$R$^{13}$;
$R^{15}$ is hydrogen or optionally substituted alkyl; and
t is 1 or 2.

In another embodiment, provided herein is a combination package comprising (a) at least one individual dose of a nucleoside analog, an anthracycline, a topoisomerase inhibitor, or a combination thereof; and (b) at least one individual dose of a compound of structural formula (I) as described above, or a salt, solvate, ester and/or prodrug thereof.

In another embodiment, provided herein is a combination package comprising (a) at least one individual dose of a nucleoside analog, wherein the nucleoside analog is a neoplastic cell antimetabolite; and (b) at least one individual dose of a compound of structural formula (I) as described above, or a salt, solvate, ester and/or prodrug thereof.

In another embodiment, provided herein is a combination package comprising (a) at least one individual dose of an anthracycline, a topoisomerase inhibitor or a combination thereof; and (b) at least one individual dose of a compound of structural formula (I) as described above, or a salt, solvate, ester and/or prodrug thereof.

In another embodiment, provided herein is a pharmaceutical composition comprising a therapeutically effective amount of (a) a nucleoside analog, an anthracycline, a topoisomerase inhibitor, or a combination thereof; and (b) a compound of structural formula (I) as described above, or a salt, solvate, ester and/or prodrug thereof.

In another embodiment, provided herein is a pharmaceutical composition comprising a therapeutically effective amount of (a) a nucleoside analog, wherein the nucleoside analog is a neoplastic cell antimetabolite; and (b) a compound of structural formula (I) as described above, or a salt, solvate, ester and/or prodrug thereof.

In another embodiment, provided herein is a pharmaceutical composition comprising a therapeutically effective amount of (a) an anthracycline, a topoisomerase inhibitor, or a combination thereof; and (b) a compound of structural formula (I) as described above, or a salt, solvate, ester and/or prodrug thereof.

In certain embodiments, provided herein are methods of treating, preventing or managing a proliferative disease. In certain embodiments, the methods comprise administering to a subject a therapeutically or prophylactically effective amount of AC220, or a pharmaceutically acceptable prodrug, salt, solvate or hydrate thereof in combination with a second anticancer agent. In one embodiment, the second agent is a nucleoside analog, an anthracycline, a topoisomerase inhibitor, or combinations thereof. In one embodiment, the second agent is a nucleoside analog, wherein the nucleoside analog is a neoplastic cell antimetabolite. In one embodiment, the second agent is an anthracycline, a topoisomerase inhibitor or a combination thereof. In one embodiment, the topoisomerase inhibitor is selected from amsacrine, etoposide, etoposide phosphate, and teniposide. In one embodiment, the topoisomerase inhibitor is etoposide. In one embodiment, the anthracycline is selected from daunorubicin, doxorubicin, epirubicin, idarubicin, mitoxantrone, amrubicin and valrubicin. In one embodiment, the anthracycline is daunorubicin. In one embodiment, the second agent is cytarabine, daunorubicin, etoposide or a combination thereof.

In one embodiment, the methods provided include the administration of AC220, or a pharmaceutically acceptable salt, prodrug, solvate or hydrate thereof in combination with cytarabine administered intrathecally at a dose from about 5 mg/m$^2$ to about 75 mg/m$^2$ once per day or once every four days, or about 30 mg/m$^2$ every four days, in another embodiment, intravenously cytarabine administered from about 5 mg/m$^2$/day to about 3 g/m$^2$/day or about 100 mg/m$^2$/day to about 200 mg/m$^2$/day. In one embodiment, the administration of AC220 occurs once a day for one week, two weeks, three weeks, four weeks or five weeks. The administration of cytarabine can be made by intravenous infusion, intravenous push, bolus injection or subcutaneous injection. In one embodiment, the administration of cytarabine occurs for 5 days. In one embodiment, the administration of cytarabine occurs for 7 days. In one embodiment, the administration of cytarabine occurs on days 1 to 5. In one embodiment, the administration of cytarabine occurs on days 1 to 7.

In one embodiment, the methods provided include the administration of AC220, or a pharmaceutically acceptable salt, prodrug, solvate or hydrate thereof in combination with about 10 mg/m$^2$ to about 150 mg/m$^2$ etoposide. For example, one embodiment includes administration of etoposide at a dose of about 30 to about 120 mg/m$^2$. One embodiment includes administration of etoposide at a dose of about 35, 50, or 100 mg/m$^2$. The administration of etoposide can be made by intravenous infusion, intravenous push, bolus injection or subcutaneous injection. In one embodiment, the administration of etoposide is once a day for 5 days, while the administration of AC220 occurs once a day for one week, two weeks, three weeks, four weeks or five weeks. In one embodiment, the administration of etoposide is once a day on days 1, 3 and 5, while the administration of AC220 occurs once a day for one week, two weeks, three weeks, four weeks or five weeks.

In one embodiment, the methods provided include the administration of AC220, or a pharmaceutically acceptable salt, prodrug, solvate or hydrate thereof in combination with about 10 mg/m$^2$ to about 50 mg/m$^2$ daunorubicin. For example, one embodiment includes administration of daunorubicin at a dose of about 20 to about 50 mg/m$^2$. One embodiment includes administration of daunorubicin at a dose of about 25, 30, or 45 mg/m$^2$. The administration of daunorubicin can be made by intravenous infusion, intravenous push, bolus injection or subcutaneous injection. In one embodiment, the administration of daunorubicin is once a day on days 1, 2 and 3, while the administration of AC220 occurs once a day for one week, two weeks, three weeks, four weeks or five weeks. In one embodiment, the administration of daunorubicin is once a day on days 1, and 2, while the administration of AC220 occurs once a day for one week, two weeks, three weeks, four weeks or five weeks. In one embodiment, the administration of daunorubicin is once a day on day 1, while the administration of AC220 occurs once a day for one week, two weeks, three weeks, four weeks or five weeks.

In one embodiment, the methods provided include the administration of AC220, or a pharmaceutically acceptable salt, prodrug, solvate or hydrate thereof in combination with cytarabine and daunorubicin.

In certain embodiments, the administration of AC220 and the second agents selected from a nucleoside analog, an anthracycline, a topoisomerase inhibitor and combinations thereof as set forth above in a week is considered a weekly cycle. The methods contemplate performing one weekly cycle, optionally waiting a period of one day to several days or one week to weeks where neither the second agent nor AC220 is given, then repeating a weekly cycle. The methods also contemplate repeating the weekly cycles continuously, for example, for 2 to 5 weeks. In addition, the methods contemplate repeating the cycle for several cycles, waiting a period of a day to several days or one week to several weeks where neither AC220 nor the second agent is given then repeating one or more cycles. Finally, the methods provide administration of a AC220/second agent weekly cycle followed by a cycle of only the second agent or AC220.

Also provided herein is a method of inhibiting the growth of a cell, comprising contacting the cell with an effective amount of AC220, or a pharmaceutically acceptable prodrug, salt, solvate or hydrate thereof in combination with a second anticancer agent selected from an anthracycline, a topoisomerase inhibitor and combinations thereof.

DETAILED DESCRIPTION

Figure 1:
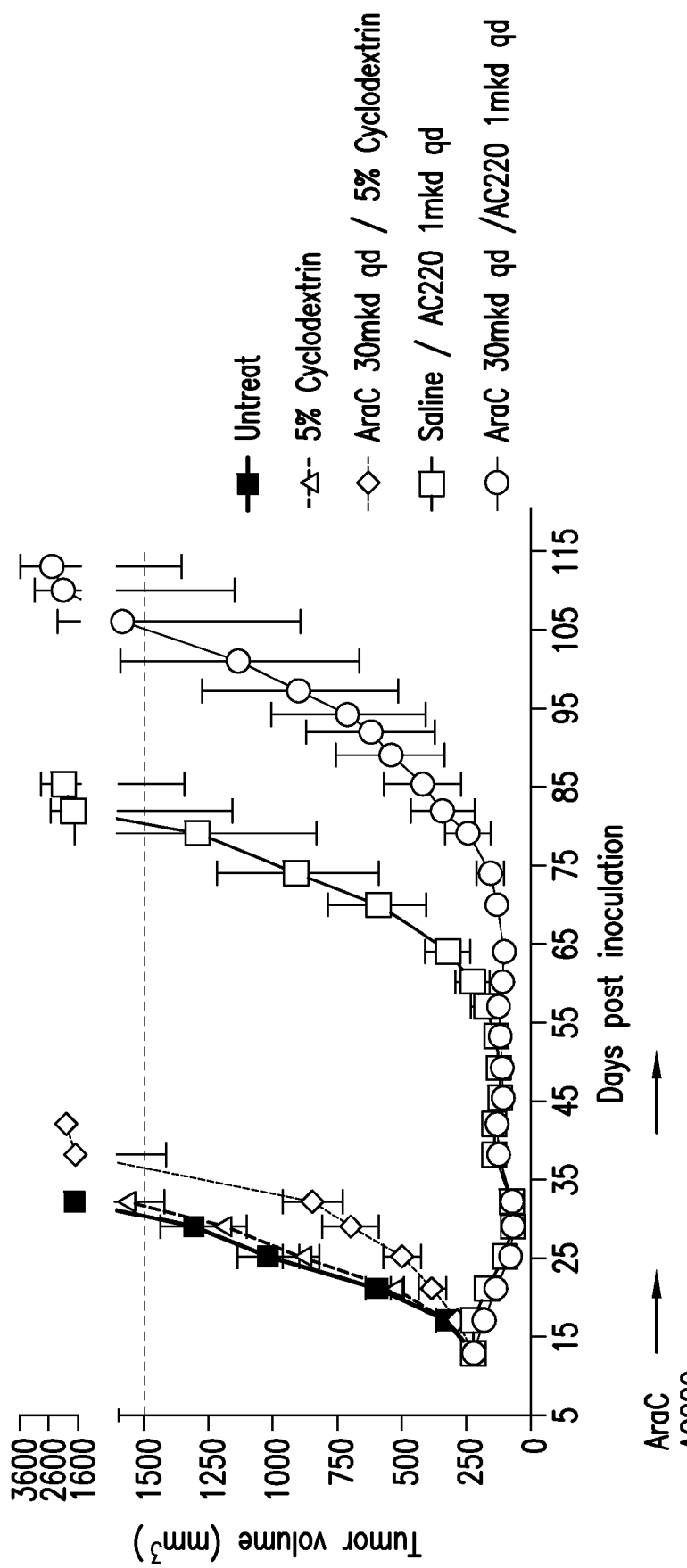
FIG. 1 is a graph showing the efficacy of AC220 plus cytarabine (overlapping administration) in controlling tumor growth as compared to control, AC220 alone, and cytarabine alone.

In certain embodiments, provided herein are methods of treating, managing, or preventing proliferative diseases comprising administering to a subject, such as a mammal in need of such treatment, management or prevention a therapeutically or prophylactically effective amount of a compound of structural formula (I) as described above, or a salt, solvate, ester and/or prodrug thereof in combination with a second agent selected from a nucleoside analog, an anthracycline, a topoisomerase inhibitor, or a combination thereof.

In certain embodiments, provided herein are methods of treating, managing, or preventing proliferative diseases comprising administering to a subject, such as a mammal in need of such treatment, management or prevention a therapeutically or prophylactically effective amount of AC220, or a pharmaceutically acceptable salt, prodrug, solvate or hydrate thereof in combination with a second agent selected from a nucleoside analog, an anthracycline, a topoisomerase inhibitor, or a combination thereof.

In certain embodiments, provided herein are methods of treating, managing, or preventing proliferative diseases comprising administering to a subject, such as a mammal in need of such treatment, management or prevention a therapeutically or prophylactically effective amount of AC220, or a pharmaceutically acceptable salt, prodrug, solvate or hydrate thereof in combination with a second agent selected from an anthracycline and a topoisomerase inhibitor.

In certain embodiments, provided herein are methods and compositions for treating a hematological neoplastic disease by combined use of a nucleoside analog, an anthracycline, a topoisomerase inhibitor, or a combination thereof, and a compound of structural formula (I) as described above, or a salt, solvate, ester and/or prodrug thereof.

In certain embodiments, provided herein are methods and compositions for treating a hematological neoplastic disease by combined use of a nucleoside analog and a compound of structural formula (I) as described above, or a salt, solvate, ester and/or prodrug thereof.

In one embodiment, the methods encompass treating, preventing or managing various cancers selected from bladder cancer, breast cancer, cervical cancer, CNS cancer, colon cancer, esophageal cancer, head and neck cancer, liver cancer, lung cancer, nasopharyngeal cancer, neuroendocrine cancer, ovarian cancer, pancreatic cancer, prostate cancer, renal cancer, salivary gland cancer, small cell lung cancer, skin cancer, stomach cancer, testicular cancer, thyroid cancer, uterine cancer, or hematologic malignancy. The cancer can be relapsed, refractory or resistant to conventional therapy.

In certain embodiments, in the methods provided herein, AC220 or a pharmaceutically acceptable salt, prodrug, solvate or hydrate thereof is administered in combination with a second active agent selected from clofarabine, cytarabine, daunorubicin and etoposide, or a combination thereof. In certain embodiments, in the methods provided herein, AC220 or a pharmaceutically acceptable salt, prodrug, solvate or hydrate thereof is administered in combination with a second active agent selected from daunorubicin and etoposide. Specific doses and dosing regimens for these combinations are provided below.

A. DEFINITIONS

To facilitate understanding of the disclosure set forth herein, a number of terms are defined below.

Generally, the nomenclature used herein and the laboratory procedures in organic chemistry, medicinal chemistry, biochemistry, biology, pharmacology, and others described herein are those well known and commonly employed in the art. Unless defined otherwise, all technical and scientific terms used herein generally have the same meaning as commonly understood by one of ordinary skill in the art to which this disclosure belongs.

The term "tumor," "neoplasm," and "neoplastic disorder or disease" are used interchangeably herein and are meant to refer to unwanted cell proliferation of one or more subset of cells in a multicellular organism resulting in harm (i.e., discomfort or decreased life expectancy) to the multicellular organisms. In certain embodiments, a tumor can be benign (non-invasive) or malignant (invasive).

The term "cancer" is meant to refer to a malignant neoplasm, which is characterized by uncontrolled cell proliferation where cells have lost their normal regulatory controls that would otherwise govern the rate of cell growth. These unregulated, dividing cells can spread throughout the body and invade normal tissues in a process referred to as "metastasis."

The term "naturally occurring" or "native" when used in connection with biological materials such as nucleic acid molecules, polypeptides, host cells, and the like, refers to materials which are found in nature and are not manipulated by man. Similarly, "non-naturally occurring" or "non-native" refers to a material that is not found in nature or that has been structurally modified or synthesized by man.

The terms "FLT3" which stands for FMS-related tyrosine kinase 3, "FLK-2" which stands for fetal liver kinase 2, "STK1" which stands for stem cell kinase 1 and cluster of differentiation 135 (CD135) are used interchangeably herein and refer to a FLT3 receptor protein or variant thereof, as described, for example, in Small et al. (1994) *Proc. Natl. Acad. Sci. USA* 91:459-463. FLT3 variants include proteins substantially homologous to a native FLT3, i.e., proteins having one or more naturally or non-naturally occurring amino acid deletions, insertions or substitutions (e.g., FLT3 derivatives, homologs and fragments), as compared to the amino acid sequence of a native FLT3. The amino acid sequence of an FLT3 variant is at least about 80% identical, at least about 90% identical, or at least about 95% identical to a native FLT3. Examples of naturally occurring mutant forms of a native FLT3 include the FLT3 ITD (internal tandem duplication) mutation, i.e. an internal tandem duplication insertion mutation, also described in Nakao et al. (1996) *Leukemia* 10:1911-1918 and the FLT3 tyrosine kinase domain mutation, i.e. a missense mutation such as the FLT3 D835 which is also described in Yamamoto et al. (2001) *Blood* 97(8):2434-2439.

The term "proliferative disorder or disease" refers to unwanted cell proliferation of one or more subset of cells in a multicellular organism resulting in harm (i.e., discomfort or decreased life expectancy) to the multicellular organisms. A proliferative disorder or disease can occur in different types of animals and humans. For example, as used herein, "proliferative disorder or disease" includes neoplastic disorders and other proliferative disorders.

The term "neoplastic disorder or disease" or "cancer" refers to a tumor resulting from abnormal or uncontrolled cellular growth. Examples of neoplastic disorders include, but are not limited to, hematopoietic disorders, such as the myeloproliferative disorders, thrombocythemia, essential thrombocytosis (ET), angiogenic myeloid metaplasia, myelofibrosis (MF), myelofibrosis with myeloid metaplasia (MMM), chronic idiopathic myelofibrosis (IMF), polycythemia vera (PV), the cytopenias, and pre-malignant myelodysplastic syndromes; cancers, such as glioma cancers, lung cancers, breast cancers, colorectal cancers, prostate cancers, gastric cancers, esophageal cancers, colon cancers, pancreatic cancers, ovarian cancers, and hematologic malignancies.

The term "hematologic malignancy" refers to cancer of the body's blood
  forming and immune system—the bone marrow and lymphatic tissue. Examples of hematological malignancies include, for instance, myelodysplasia, lymphomas, leukemias, lymphomas (non-Hodgkin's lymphoma), Hodgkin's disease (also called Hodgkin's lymphoma), and myeloma, such as acute lymphocytic leukemia (ALL), acute myeloid leukemia (AML), acute promyelocytic leukemia (APL), chronic lymphocytic leukemia (CLL), chronic myeloid leukemia (CML), chronic neutrophilic leukemia (CNL), acute undifferentiated leukemia (AUL), anaplastic large-cell lymphoma (ALCL), prolymphocytic leukemia (PML), juvenile myelomonocytic leukemia (JMML), adult T-cell ALL, AML with trilineage myelodysplasia (AML/TMDS), mixed lineage leukemia (MLL), myelodysplastic syndromes (MDSs), myeloproliferative disorders (MPD), and multiple myeloma, (MM).

The term "leukemia" refers to malignant neoplasms of the blood-forming tissues, including, but not limited to, chronic lymphocytic leukemia, chronic myelocytic leukemia, acute lymphoblastic leukemia, acute myelogenous leukemia and acute myeloblastic leukemia. The leukemia can be relapsed, refractory, or resistant to conventional therapy.

The term "relapsed" refers to a situation where a subject or a mammal, which has had a remission of cancer after therapy has a return of cancer cells.

The term "refractory or resistant" refers to a circumstance where a subject or a mammal, even after intensive treatment, has residual cancer cells in his body.

The term "drug resistance" refers to the condition when a disease does not respond to the treatment of a drug or drugs. Drug resistance can be either intrinsic, which means the disease has never been responsive to the drug or drugs, or it can be acquired, which means the disease ceases responding to a drug or drugs that the disease had previously responded to. In certain embodiments, drug resistance is intrinsic. In certain embodiments, the drug resistance is acquired. As used herein, the term "drug resistance" is meant to include imatinib-resistance, dasatinib-resistance, and/or nilotinib-resistance.

The term "overexpress" or "overexpression" is meant that a cell associated with a disease, disorder, or condition comprises a detectably higher level of a protein, such as FLT3 or FLT3, than an otherwise identical cell that is not associated with a disease, disorder or condition.

The term "subject" refers to an animal, including, but not limited to, a primate (e.g., human), cow, pig, sheep, goat, horse, dog, cat, rabbit, rat, or mouse. The terms "subject" and "patient" are used interchangeably herein in reference, for example, to a mammalian subject, such as a human subject, in one embodiment, a human.

The terms "treat," "treating," and "treatment" are meant to include alleviating or abrogating a disorder, disease, or condition, or one or more of the symptoms associated with the disorder, disease, or condition; or alleviating or eradicating the cause(s) of the disorder, disease, or condition itself.

The terms "prevent" "preventing" and "prevention" include the inhibition of a symptom of the particular disease or disorder. In some embodiments, patients with familial history of cancer or leukemia are candidates for preventive regimens. Generally, the term "preventing" refers to administration of the drug prior to the onset of symptoms, particularly to patients at risk of cancer.

As used herein and unless otherwise indicated, the terms "manage", "managing" and "management" encompasse preventing the recurrence of the particular disease or disorder in a patient who had suffered from it, lengthening the time a patient who had suffered from the disease or disorder remains in remission, reducing mortality rates of the patients, and/or maintaining a reduction in severity or avoidance of a symptom associated with the disease or condition being managed.

The term "contacting" or "contact" is meant to refer to bringing together of a therapeutic agent and cell or tissue such that a physiological and/or chemical effect takes place as a result of such contact. Contacting can take place in vitro, ex vivo, or in vivo. In one embodiment, a therapeutic agent is contacted with a cell in cell culture (in vitro) to determine the effect of the therapeutic agent on the cell. In another embodiment, the contacting of a therapeutic agent with a cell or tissue includes the administration of a therapeutic agent to a subject having the cell or tissue to be contacted.

The term "therapeutically effective amount" are meant to include the amount of a compound that, when administered, is sufficient to prevent development of, or alleviate to some extent, one or more of the symptoms of the disorder, disease, or condition being treated. The term "therapeutically effective amount" also refers to the amount of a compound that is sufficient to elicit the biological or medical response of a biological molecule (e.g., a protein, enzyme, RNA, or DNA), cell, tissue, system, animal, or human, which is being sought by a researcher, veterinarian, medical doctor, or clinician.

The terms "co-administration" and "in combination with" include the administration of two therapeutic agents (for example, AC220 and a second anti-cancer agent, such as daunorubicin or etoposide) either simultaneously, concurrently or sequentially with no specific time limits. In one embodiment, both agents are present in the cell or in the patient's body at the same time or exert their biological or therapeutic effect at the same time. In one embodiment, the two therapeutic agents are in the same composition or unit dosage form. In another embodiment, the two therapeutic agents are in separate compositions or unit dosage forms.

As used herein, the term "nucleoside analog" denotes an organic compound containing a nucleobase bound to a carbohydrate ring via a nitrogen atom of the nucleobase. In one embodiment, the nucleobase is a nitrogenous base. In another embodiment, the carbohydrate ring is a sugar ring. The nucleoside analog optionally contains a phosphate moiety. Examples of the nitrogenous base include, but are not limited to purine and their derivatives, such as adenine, guanine, and hypoxanthine, and pyrimidine and their derivatives, such as cytosine, uracil, thymine, and 4-amino-triazin-2(1H)-one (an aza derivative of cytosine). The nucleoside analog for use herein is a neoplastic cell antimetaboite, i.e., a compound that interferes with the biological functions of neoplastic cells. For example, the nucleoside analog may interfere with DNA methylation, DNA synthesis, and other functions related to cell division.

As used herein, the term "anthracycline" refers to a type of antineoplastic antibiotics that come from certain types of Streptomyces bacteria, or derivatives thereof.

As used herein, the term "topoisomerase inhibitor" refers to a substance that blocks topoisomerase enzymes.

As used herein, the term "non-void day", it is meant a day when at least one of the compound of formula (I), or a salt, solvate, ester and/or prodrug thereof, or a second agent, such as a nucleoside analog, an anthracyclin or a topoisomerase inhibitor is administered.

By "simultaneous administration", it is meant that the nucleoside analog, an anthracyclin or a topoisomerase inhibitor and the compound of structural formula (I), or a salt, solvate, ester and/or prodrug thereof, are administered on the same day. For the simultaneous administration, the nucleoside analog, an anthracyclin or a topoisomerase inhibitor, and the compound of structural formula (I), or a salt, solvate, ester and/or prodrug thereof, can be administered at the same time or one at a time.

By "sequential administration", it is meant that during a period of two or more days of continuous co-administration without any void day, only one of the nucleoside analog, an anthracyclin or a topoisomerase inhibitor, and the compound of structural formula (I), or a salt, solvate, ester and/or prodrug thereof, is administered on any given day.

By "overlapping administration", it is meant that during a period of two or more days of continuous co-administration without any void day, there is at least one day of simultaneous administration and at least one day when only one of the nucleoside analog, an anthracyclin or a topoisomerase inhibitor, and the compound of structural formula (I), or a salt, solvate, ester and/or prodrug thereof, is administered.

By "interval administration", it is meant a period of co-administration with at least one void day. By "continuous administration", it is meant a period of co-administration without any void day. The continuous administration may be simultaneous, sequential, or overlapping, as described above.

The term "pharmaceutically acceptable carrier," "pharmaceutically acceptable excipient," "physiologically acceptable carrier," or "physiologically acceptable excipient" refers to a pharmaceutically-acceptable material, composition, or vehicle, such as a liquid or solid filler, diluent, solvent, or encapsulating material. In one embodiment, each component is "pharmaceutically acceptable" in the sense of being compatible with the other ingredients of a pharmaceutical formulation, and suitable for use in contact with the tissue or organ of humans and animals without excessive toxicity, irritation, allergic response, immunogenicity, or other problems or complications, commensurate with a reasonable benefit/risk ratio. See, *Remington: The Science and Practice of Pharmacy,* 21st Edition, Lippincott Williams & Wilkins: Philadelphia, Pa., 2005; *Handbook of Pharmaceutical Excipients,* 5th Edition, Rowe et al., Eds., The Pharmaceutical Press and the American Pharmaceutical Association: 2005; and *Handbook of Pharmaceutical Additives,* 3rd Edition, Ash and Ash Eds., Gower Publishing Company: 2007; *Pharmaceutical Preformulation and Formulation,* 2nd Edition, Gibson Ed., CRC Press LLC: Boca Raton, Fla., 2009.

The term "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 50%, 20%, 15%, 10%, 9%, 8%, 7%, 6%, 5%, 4%, 3%, 2%, 1%, 0.5%, or 0.05% of a given value or range.

The terms "active ingredient" and "active substance" refer to a compound, which is administered, alone or in combination with one or more pharmaceutically acceptable excipients, to a subject for treating, preventing, or ameliorating one or more symptoms of a condition, disorder, or disease. As used herein, "active ingredient" and "active substance" may be an optically active isomer of a compound described herein.

The terms "drug," "therapeutic agent," and "chemotherapeutic agent" refer to a compound, or a pharmaceutical composition thereof, which is administered to a subject for treating, preventing, or ameliorating one or more symptoms of a condition, disorder, or disease.

As used herein and unless otherwise indicated, the term "hydrate" means a compound provided herein or a salt thereof, that further includes a stoichiometric or non-stoichiometric amount of water bound by non-covalent intermolecular forces.

As used herein and unless otherwise indicated, the term "solvate" means a solvate formed from the association of one or more solvent molecules to a compound provided herein. The term "solvate" includes hydrates (e.g., mono-hydrate, dihydrate, trihydrate, tetrahydrate thereof and the like).

"Alkyl" refers to a straight or branched hydrocarbon chain consisting solely of carbon and hydrogen atoms, containing no unsaturation, having from one to ten carbon atoms, and which is attached to the rest of the molecule by a single bond, e.g., methyl, ethyl, n-propyl, 1-methylethyl(iso-propyl), n-butyl, n-pentyl, 1,1-dimethylethyl(t-butyl), and the like.

"Alkenyl" refers to a straight or branched hydrocarbon chain consisting solely of carbon and hydrogen atoms, containing at least one double bond, having from two to ten carbon atoms, and which is attached to the rest of the molecule by a single bond or a double bond, e.g., ethenyl, prop-1-enyl, but-1-enyl, pent-1-enyl, penta-1,4-dienyl, and the like.

"Alkynyl" refers to a straight or branched hydrocarbon chain consisting solely of carbon and hydrogen atoms, containing at least one triple bond, having from two to ten carbon atoms, and which is attached to the rest of the molecule by a single bond or a triple bond, e.g., ethynyl, prop-1-ynyl, but-1-ynyl, pent-1-ynyl, pent-3-ynyl and the like.

"Alkylene" and "alkylene chain" refer to a straight or branched divalent hydrocarbon chain consisting solely of carbon and hydrogen, containing no unsaturation and having from one to eight carbon atoms, e.g., methylene, ethylene, propylene, n-butylene and the like. The alkylene chain may be attached to the rest of the molecule through any two carbons within the chain.

"Alkoxy" refers to the group having the formula —OR wherein R is alkyl or haloalkyl. An "optionally substituted alkoxy" refers to the group having the formula —OR wherein R is an optionally substituted alkyl as defined herein.

"Amino" refers to a group having the formula —NR'R" wherein R' and R" are each independently hydrogen, alkyl or haloalkyl. An "optionally substituted amino" refers to a group having the formula —NR'R" wherein one or both of R' and R" are optionally substituted alkyl as defined herein.

"Aryl" refers to a group of carbocylic ring system wherein at least one of the rings is aromatic. The aryl may be fully aromatic, examples of which are phenyl, naphthyl, anthracenyl, acenaphthylenyl, azulenyl, fluorenyl, indenyl and pyrenyl. The aryl may also contain an aromatic ring in combination with a non-aromatic ring, examples of which are acenaphene, indene, and fluorene.

"Aralkyl" refers to a group of the formula —$R_aR_b$ where $R_a$ is an alkyl group as defined above, substituted by $R_b$, an aryl group, as defined above, e.g., benzyl. Both the alkyl and aryl groups may be optionally substituted as defined herein.

"Cycloalkyl" refers to a stable monovalent monocyclic or bicyclic hydrocarbon group consisting solely of carbon and hydrogen atoms, having from three to ten carbon atoms, and which is saturated and attached to the rest of the molecule by a single bond, e.g., cyclopropyl, cyclobutyl, cyclopentyl, cyclohexyl, decalinyl, norbomane, norbomene, adamantyl, bicyclo[2.2.2]octane and the like.

"Cycloalkylalkyl" refers to a group of the formula —$R_aR_d$ where $R_a$ is an alkyl group as defined above and $R_d$ is a cycloalkyl group as defined above. The alkyl group and the cylcoalkyl group may be optionally substituted as defined herein.

"Halo", "halogen" or "halide" refers to F, Cl, Br or I.

"Haloalkyl" refers to an alkyl group in which one or more of the hydrogen atoms are replaced by halogen. Such groups include, but are not limited to, chloromethyl, trifluoromethyl and 1-chloro-2-fluoroethyl.

"Haloalkenyl" refers to an alkenyl group in which one or more of the hydrogen atoms are replaced by halogen. Such groups include, but are not limited to, 1-chloro-2-fluoroethenyl.

"Heterocyclyl" refers to a stable 3- to 15-membered ring which consists of carbon atoms and from one to five heteroatoms selected from the group consisting of nitrogen, oxygen and sulfur. In one embodiment, the heterocyclic ring system may be a monocyclic, bicyclic or tricyclic ring or tetracyclic ring system, which may include fused or bridged ring systems; and the nitrogen or sulfur atoms in the heterocyclic ring system may be optionally oxidized; the nitrogen atom may be optionally quaternized; and the heterocyclyl group may be partially or fully saturated or aromatic. The heterocyclic ring system may be attached to the main structure at any heteroatom or carbon atom which results in the creation of a stable compound. Exemplary heterocylic radicals include, morpholinyl, piperidinyl, piperazinyl, pyranyl, pyrrolidinyl and others.

"Heteroaralkyl" refers to a group of the formula —$R_aR_f$ where $R_a$ is an alkyl group as defined above and $R_f$ is a heteroaryl group as defined herein. The alkyl group and the heteroaryl group may be optionally substituted as defined herein.

"Heteroaryl" refers to a heterocyclyl group as defined above which is aromatic. The heteroaryl group may be attached to the main structure at any heteroatom or carbon atom which results in the creation of a stable compound. Examples of such heteroaryl groups include, but are not limited to: acridinyl, benzimidazolyl, benzindolyl, benzisoxazinyl, benzo[4,6]imidazo[1,2-a]pyridinyl, benzofuranyl, benzonaphthofuranyl, benzothiadiazolyl, benzothiazolyl, benzothiophenyl, benzotriazolyl, benzothiopyranyl, benzoxazinyl, benzoxazolyl, benzothiazolyl, β-carbolinyl, carbazolyl, cinnolinyl, dibenzofuranyl, furanyl, imidazolyl, imidazopyridinyl, imidazothiazolyl, indazolyl, indolizinyl, indolyl, isobenzothienyl, isoindolinyl, isoquinolinyl, isothiazolidinyl, isothiazolyl, naphthyridinyl, octahydroindolyl, octahydroisoindolyl, oxazolidinonyl, oxazolidinyl, oxazolopyridinyl, oxazolyl, oxiranyl, perimidinyl, phenanthridinyl, phenathrolinyl, phenarsazinyl, phenazinyl, phenothiazinyl, phenoxazinyl, phthalazinyl, pteridinyl, purinyl, pyrazinyl, pyrazolyl, pyridazinyl, pyridinyl, pyridopyridinyl, pyrimidinyl, pyrrolyl; quinazolinyl, quinolinyl, quinoxalinyl, tetrazolyl, thiadiazolyl, thiazolyl, thiophenyl, triazinyl and triazolyl.

"Heterocyclylalkyl" refers to a group of the formula —$R_aR_e$ wherein $R_a$ is an alkyl group as defined above and $R_e$ is a heterocyclyl group as defined herein. The alkyl group and the heterocyclyl group may be optionally substituted as defined herein.

"Heterocyclylalkoxy" refers to a group of the formula —$OR_aR_e$ wherein —$R_aR_e$ is a heterocyclylalkyl group as defined above. The alkyl group and the heterocyclyl group may be optionally substituted as defined herein.

"Optionally substituted alkyl", "optionally substituted alkenyl" and "optionally substituted alkynyl" refer to alkyl groups, alkenyl groups and alkynyl groups, respectively, that may be optionally substituted by one or more substituents independently selected from the group consisting of nitro, halo, azido, cyano, cycloalkyl, heteroaryl, heterocyclyl, —$OR^x$, —$N(R^y)(R^z)$, —$SR^x$, —$C(J)R^x$, —$C(J)OR^x$, —$C(J)N(R^y)(R^z)$, —$C(J)SR^x$, —$S(O)_tR^w$ (where t is 1 or 2), —$OC(J)R^x$, —$OC(J)OR^x$, —$OC(J)N(R^y)(R^z)$, —$OC(J)SR^x$, —$N(R^x)C(J)R^x$, $N(R^x)C(J)R^x$, —$N(R^x)C(J)N(R^y)(R^z)$, —$N(R^x)C(J)SR^x$, —$Si(R^w)_3$, —$N(R^x)S(O)_2R^w$, —$N(R^x)S(O)_2N(R^y)(R^z)$, —$S(O)_2N(R^y)(R^z)$, —$P(O)(R^v)_2$, —$OP(O)(R^v)_2$, —$C(J)N(R^x)S(O)_2R^w$, —$C(J)N(R^x)N(R^x)S(O)_2R^w$, —$C(R^x)=N(OR^x)$, and —$C(R^x)=NN(R^y)(R^z)$, wherein:

$R^x$ is hydrogen, alkyl, alkenyl, alkynyl, cycloalkyl, cycloalkylalkyl, heterocyclyl, heterocyclylalkyl, aryl, aralkyl, heteroaryl, or heteroaralkyl;

$R^y$ and $R^z$ are each independently hydrogen, alkyl, alkenyl, alkynyl, cycloalkyl, cycloalkylalkyl, heterocyclyl, heterocyclylalkyl, aryl; aralkyl, heteroaryl, or heteroaralkyl; or $R^y$ and $R^z$, together with the nitrogen atom to which they are attached, form a heterocyclyl or heteroaryl;

$R^w$ is alkyl, alkenyl, alkynyl, cycloalkyl, cycloalkylalkyl, heterocyclyl, heterocyclylalkyl, aryl, aralkyl, heteroaryl, or heteroaralkyl;

$R^v$ is alkyl, alkenyl, alkynyl, cycloalkyl, cycloalkylalkyl, heterocyclyl, heterocyclylalkyl, aryl, aralkyl, heteroaryl, heteroaralkyl, hydroxy, —$OR^x$ or —$N(R^y)(R^z)$; and J is O, $NR^x$ or S.

Unless stated otherwise specifically described in the specification, it is understood that the substitution can occur on any carbon of the alkyl, alkenyl or alkynyl group.

"Optionally substituted aryl", "optionally substituted cycloalkyl", "optionally substituted heteroaryl" and "optionally substituted heterocyclyl" refers to aryl, cycloalkyl, heteroaryl and heterocyclyl groups, respectively, that are optionally substituted by one or more substituents selected from the group consisting of nitro, halo, haloalkyl, haloalkenyl, azido, cyano, oxo, thioxo, imino, alkyl, alkenyl, alkynyl, cycloalkyl, cycloalkylalkyl, heterocyclyl, heterocyclylalkyl, heteroaryl, heteroaralkyl, —$R^vOR^x$, —$R^vN(R^y)(R^z)$, —$R^vSR^x$, —$R^vC(J)R^x$, —$R^vC(J)OR^x$, —$R^vC(J)N(R^y)(R^z)$, —$R^vC(J)SR^x$, —$R^vS(O)_tR^w$ (where t is 1 or 2), —$R^vOC(J)R^x$, —$R^vOC(J)OR^x$, —$R^vOC(J)N(R^y)(R^z)$, —$R^vOC(J)SR^x$, —$R^vN(R^x)C(J)R^x$, —$R^vN(R^x)C(J)OR^x$, —$R^vN(R^x)C(J)N(R^y)(R^z)$, —$R^vN(R^x)C(J)SR^x$, —$R^vSi(R^w)_3$, —$R^vN(R^x)S(O)_2R^w$, —$R^vN(R^x)S(O)_2N(R^y)(R^z)$, —$R^vS(O)_2N(R^y)(R^z)$, —$R^vP(O)(R^y)_2$, —$R^vOP(O)(R^y)_2$, —$R^vC(J)N(R^x)S(O)_2R^w$, —$R^vC(J)N(R^x)N(R^x)S(O)_2R^w$, —$R^vC(R^x)=N(OR^x)$ and —$R^vC(R^x)=NN(R^y)(R^z)$, wherein:

each $R^v$ is independently alkylene or a direct bond;

each $R^v$ is independently alkyl, alkenyl, alkynyl, cycloalkyl, cycloalkylalkyl, heterocyclyl, heterocyclylalkyl, aryl, aralkyl, heteroaryl, heteroaralkyl, hydroxy, —$OR^x$ or —$N(R^y)(R^z)$;

$R^w$ is alkyl, alkenyl, alkynyl, cycloalkyl, cycloalkylalkyl, heterocyclyl, heterocyclylalkyl, aryl, aralkyl, heteroaryl, or heteroaralkyl;

each $R^x$ is independently hydrogen, alkyl, alkenyl, alkynyl, cycloalkyl, cycloalkylalkyl, heterocyclyl, heterocyclylalkyl, aryl, aralkyl, heteroaryl, or heteroaralkyl;

$R^y$ and $R^z$ are each independently hydrogen, alkyl, alkenyl, alkynyl, cycloalkyl, cycloalkylalkyl, heterocyclyl, heterocyclylalkyl, aryl, aralkyl, heteroaryl, or heteroaralkyl;

$R^y$ and $R^z$, together with the nitrogen atom to which they are attached, form a heterocycle or heteroaryl; and J is O, $NR^x$ or S.

Unless stated otherwise specifically described in the specification, it is understood that the substitution can occur on any atom of the cycloalkyl, heterocyclyl, aryl or heteroaryl group.

"Oxo" refers to =O.

Compounds for use herein, namely, the nucleoside analogs as well as the compounds of formula (I) and its subgenus and specific embodiments, include those compounds and their pharmaceutically acceptable derivatives. As used herein, "pharmaceutically acceptable derivatives" of a compound include salts, esters, enol ethers, enol esters, acetals, ketals, orthoesters, hemiacetals, hemiketals, acids, bases, solvates, and/or prodrugs thereof. Such derivatives may be readily prepared by those of skill in this art using known methods for such derivatization. The compounds produced may be administered to animals or humans without substantial toxic effects and either are pharmaceutically active or are prodrugs.

"Salt" means any acid and/or base addition salt of a compound provided herein is a pharmaceutically acceptable salt thereof. The pharmaceutically acceptable salt means a salt of a compound provided herein which is, within the scope of sound medical judgment, suitable for use in contact with the tissues of humans and lower animals without undue toxicity, irritation, allergic response, and the like, commensurate with a reasonable benefit/risk ratio, generally water or oil-soluble or dispersible, and effective for their intended use. Where applicable and compatible with the chemical properties of the nicotinic desensitizer, the term includes pharmaceutically-acceptable acid addition salts and pharmaceutically-acceptable base addition salts. Lists of suitable salts are found in, e.g., S. M. Birge et al., *J. Pharm. Sci.*, 1977, 66, pp. 1-19. Pharmaceutically acceptable salts include, but are not limited to, amine salts, such as but not limited to N,N'-dibenzylethylenediamine, chloroprocaine, choline, ammonia, diethanolamine and other hydroxyalkylamines, ethylenediamine, N-methylglucamine, procaine, N-benzylphenethylamine, 1-para-chlorobenzyl-2-pyrrolidin-1'-ylmethyl-benzimidazole, diethylamine and other alkylamines, piperazine and tris(hydroxymethyl)aminomethane; alkali metal salts, such as but not limited to lithium, potassium and sodium; alkali earth metal salts, such as but not limited to barium, calcium and magnesium; transition metal salts, such as but not limited to zinc; and other metal salts, such as but not limited to sodium hydrogen phosphate and disodium phosphate; and also including, but not limited to, salts of mineral acids, such as but not limited to hydrochlorides and sulfates; and salts of organic acids, such as but not limited to acetates, lactates, malates, tartrates, citrates, ascorbates, succinates, butyrates, valerates and fumarates.

"Ester" means any ester of a compound of the present invention in which any of the —COOH functions of the molecule is replaced by a —COOR function, in which the R moiety of the ester is any carbon-containing group which forms a stable ester moiety, including but not limited to alkyl, alkenyl, alkynyl, cycloalkyl, cycloalkylalkyl, aryl, arylalkyl, heterocyclyl, heterocyclylalkyl and substituted derivatives thereof. The term "ester" includes but is not limited to pharmaceutically acceptable esters thereof. Pharmaceutically acceptable esters include, but are not limited to, alkyl, alkenyl, alkynyl, aryl, heteroaryl, aralkyl, heteroaralkyl, cycloalkyl and heterocyclyl esters of acidic groups, including, but not limited to, carboxylic acids, phosphoric acids, phosphinic acids, sulfonic acids, sulfinic acids and boronic acids.

Pharmaceutically acceptable enol ethers include, but are not limited to, derivatives of formula C=C(OR) where R is hydrogen, alkyl, alkenyl, alkynyl, aryl, heteroaryl, aralkyl, heteroaralkyl, cycloalkyl or heterocyclyl. Pharmaceutically acceptable enol esters include, but are not limited to, derivatives of formula C=C(OC(O)R) where R is hydrogen, alkyl, alkenyl, alkynyl, aryl, heteroaryl, aralkyl, heteroaralkyl, cycloalkyl or heterocyclyl.

"Prodrug" is a compound that, upon in vivo administration, is metabolized by one or more steps or processes or otherwise converted to the biologically, pharmaceutically or therapeutically active form of the compound. To produce a prodrug, the pharmaceutically active compound is modified such that the active compound will be regenerated by metabolic processes. The prodrug may be designed to alter the metabolic stability or the transport characteristics of a drug, to mask side effects or toxicity, to improve the flavor of a drug or to alter other characteristics or properties of a drug. By virtue of knowledge of pharmacodynamic processes and drug metabolism in vivo, those of skill in this art, once a pharmaceutically active compound is known, can design prodrugs of the compound (see, e.g., Nogrady (2005) *Medicinal Chemistry A Biochemical Approach*, Oxford University Press, New York).

As used herein, "substantially pure" means sufficiently homogeneous to appear free of readily detectable impurities as determined by standard methods of analysis, such as thin layer chromatography (TLC), gel electrophoresis, high performance liquid chromatography (HPLC) and mass spectrometry (MS), used by those of skill in the art to assess such purity, or sufficiently pure such that further purification would not detectably alter the physical and chemical properties, such as enzymatic and biological activities, of the substance. Methods for purification of the compounds to produce substantially chemically pure compounds are known to those of skill in the art. A substantially chemically pure compound may, however, be a mixture of stereoisomers. In such instances, further purification might increase the specific activity of the compound.

Unless specifically stated otherwise, where a compound may assume alternative tautomeric, regioisomeric and/or stereoisomeric forms, all alternative isomers are intended to be encompassed within the scope of the claimed subject matter. For example, where a compound is described as having one of two tautomeric forms, it is intended that the both tautomers be encompassed herein.

Thus, the compounds provided herein may be enantiomerically pure, or be stereoisomeric or diastereomeric mixtures.

It is to be understood that the compounds provided herein may contain chiral centers. Such chiral centers may be of either the (R) or (S) configuration, or may be a mixture thereof. It is to be understood that the chiral centers of the compounds provided herein may undergo epimerization in vivo. As such, one of skill in the art will recognize that administration of a compound in its (R) form is equivalent, for compounds that undergo epimerization in vivo, to administration of the compound in its (S) form.

Optically active (+) and (−), (R)- and (S)-, or (D)- and (L)-isomers may be prepared using chiral synthons or chiral reagents, or resolved using conventional techniques, such as reverse phase HPLC.

As used herein, the term "enantiomerically pure" or "pure enantiomer" denotes that the compound comprises more than 75% by weight, more than 80% by weight, more than 85% by weight, more than 90% by weight, more than 91% by weight, more than 92% by weight, more than 93% by weight, more than 94% by weight, more than 95% by weight, more than 96% by weight, more than 97% by weight, more than 98% by weight, more than 98.5% by weight, more than 99% by weight, more than 99.2% by weight, more than 99.5% by weight, more than 99.6% by weight, more than 99.7% by weight, more than 99.8% by weight or more than 99.9% by weight, of the enantiomer.

Where the number of any given substituent is not specified (e.g., haloalkyl), there may be one or more substituents present. For example, "haloalkyl" may include one or more of the same or different halogens.

In the description herein, if there is any discrepancy between a chemical name and chemical structure, the structure preferably controls.

As used herein, the abbreviations for any protective groups, amino acids and other compounds, are, unless indicated otherwise, in accord with their common usage, recognized abbreviations, or the IUPAC-IUB Commission on Biochemical Nomenclature (see, Biochem. 1972, 11:942-944).

The above-described imidazolothiazole compounds of formula (I) can be synthesized via methods known to one skilled in the art. Certain specific procedures for obtaining imidazolothiazole compounds are described in International Application No. PCT/US2007/006613, entitled "Imidazolothiazole Compounds for the Treatment of Disease" and published as WO 2007/109120, the content of which is herein incorporated by reference in its entirety for all purposes.

B. COMPOUNDS OF FORMULA (I)

In certain embodiments, provided herein are imidazolothiazole compounds of formula (I), or salts, solvates, esters and/or prodrugs thereof, that can be used in combination with a nucleoside analog, an anthracycline or a topoisomerase inhibitor as described herein for treating proliferative diseases. In certain embodiments, provided herein are imidazolothiazole compounds of formula (I), or salts, solvates, esters and/or prodrugs thereof, that can be used in combination with the nucleoside analogs as described herein for treating hematological neoplastic diseases.

In one embodiment of formula (I), $X^2$ is —O—.
In another embodiment of formula (I), X is —S—.
In another embodiment of formula (I), two of the three $R^0$ are hydrogen; and the other $R^0$ is

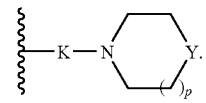

In one embodiment, Y is —O—. In another embodiment, K is —O(CH$_2$)$_q$—, wherein the oxygen atom is attached to the phenyl ring of the fused-tricyclic core. In another embodiment, p is an integer of 1. In another embodiment, q is an integer of 2.

In another embodiment of formula (I), $R^2$ is hydrogen.
In another embodiment of formula (I), $R^3$ is hydrogen.
In another embodiment of formula (I), one of $R^{10}$ is hydrogen, and the other $R^{10}$ is optionally substituted alkyl.

In one embodiment of formula (I), the compound can be represented by structural formula (Ia):

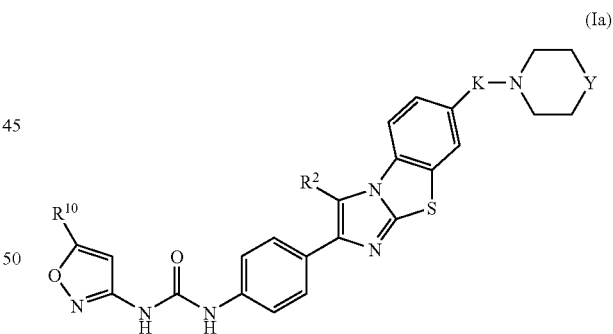

wherein
K is —O(CH$_2$)$_q$—, —(CH$_2$)$_q$O—, —(CH$_2$)$_q$- or —(CH$_2$)$_q$O(CH$_2$)$_q$—;
each q is independently 1 to 4;
Y is —O—, —S—, or —N(R$^{14}$)—;
$R^2$ is independently hydrogen, halo, optionally substituted alkyl, or —OR$^{12}$;
$R^{10}$ is hydrogen, halo, optionally substituted alkyl, or optionally substituted cycloalkyl; and
$R^{12}$ is hydrogen or optionally substituted alkyl.
In another embodiment of formula (I), $R^3$ is hydrogen.
In specific embodiments, the compound of structural formula (I) is selected from the group consisting of 3-(2-{4-[3-(5-tert-Butyl-isoxazol-3-yl)-ureido]-phenyl}-benzo[d]imidazo[2,1-b]thiazol-7-yl)-N-(2-morpholin-4-yl-ethyl)-propionamide;

3-(2-{4-[3-(5-tert-Butyl-isoxazol-3-yl)-ureido]-phenyl}-benzo[d]imidazo[2,1-b]thiazol-7-yl)-N-(2-piperidin-1-yl-ethyl)-propionamide;

3-(2-{4-[3-(5-tert-Butyl-isoxazol-3-yl)-ureido]-phenyl}-benzo[d]imidazo[2,1-b]thiazol-7-yl)-N-(2-pyrrolidin-1-yl-ethyl)-propionamide;

1-(5-tert-Butyl-isoxazol-3-yl)-3-{4-[7-(4-methyl-piperazin-1-yl)-benzo[d]imidazo[2,1-b]thiazol-2-yl]-phenyl}-urea;

1-(5-tert-Butyl-isoxazol-3-yl)-3-(4-{7-[2-(4-methyl-piperazin-1-yl)-ethoxy]-benzo[d]imidazo[2,1-b]thiazol-2-yl}-phenyl)-urea;

1-(5-tert-Butyl-isoxazol-3-yl)-3-{4-[7-(2-piperidin-1-yl-ethoxy)-benzo[d]imidazo[2,1-b]thiazol-2-yl]-phenyl}-urea;

1-(5-tert-Butyl-isoxazol-3-yl)-3-{4-[7-(3-morpholin-4-yl-propoxy)-benzo[d]imidazo[2,1-b]thiazol-2-yl]-phenyl}-urea;

1-(5-tert-Butyl-isoxazol-3-yl)-3-(4-{7-[3-(4-methyl-piperazin-1-yl)-propoxy]-benzo[d]imidazo[2,1-b]thiazol-2-yl}-phenyl)-urea;

1-(5-tert-Butyl-isoxazol-3-yl)-3-(4-{7-[3-(4-methanesulfonyl-piperazin-1-yl)-propoxy]-benzo[d]imidazo[2,1-b]thiazol-2-yl}-phenyl)-urea;

N-(5-tert-Butyl-isoxazol-3-yl)-N'-(4-{7-[3-(4-ethyl-piperazin-1-yl)propyl]imidazo[2,1-b][1,3)benzothiazol-2-yl}phenyl)urea;

1-(5-tert-Butyl-isoxazol-3-yl)-3-{4-[7-(3-morpholin-4-yl-3-oxo-propyl)-benzo[d]imidazo[2,1-b]thiazol-2-yl]-phenyl}-urea;

3-(5-tert-Butyl-isoxazol-3-yl)-1-methyl-1-{4-[7-(3-morpholin-4-yl-propyl)-benzo[d]imidazo[2,1-b]thiazol-2-yl]-phenyl}-urea;

1-(5-tert-Butyl-isoxazol-3-yl)-3-{4-[7-(3-morpholin-4-yl-propyl)-benzo[d]imidazo[2,1-b]thiazol-2-yl]-phenyl}-urea;

N-(5-tert-Butyl-isoxazol-3-yl)-N'-{4-[7-(2-morpholin-4-yl-ethoxy)imidazo[2,1-b][1,3]benzothiazol-2-yl]phenyl}urea;

1-(5-tert-Butyl-isoxazol-3-yl)-3-[4-(7-morpholin-4-yl-benzo[d]imidazo[2,1-b]thiazol-2-yl)-phenyl]-urea;

N-(5-tert-Butyl-isoxazol-3-yl)-N'-{4-[7-(3-piperidin-1-yl-propyl)imidazo[2,1-b][1,3]benzothiazol-2-yl]phenyl}urea;

N-(5-tert-butyl-isoxazol-3-yl)-N'-{4-[5-(2-morpholin-4-yl-ethoxy)imidazo[2,1-b][1,3]benzothiazol-2-yl]phenyl}urea;

2-(2-{4-[3-(5-tert-Butyl-isoxazol-3-yl)-ureido]-phenyl}-benzo[d]imidazo[2,1-b]thiazol-7-yl)-N-(2-morpholin-4-yl-ethyl)-acetamide;

2-(2-{4-[3-(5-tert-Butyl-isoxazol-3-yl)-ureido]-phenyl}-benzo[d]imidazo[2,1-b]thiazol-7-yl)-N-(2-piperidin-1-yl-ethyl)-acetamide;

2-(2-{4-[3-(5-tert-Butyl-isoxazol-3-yl)-ureido]-phenyl}-benzo[d]imidazo[2,1-b]thiazol-7-yl)-N-(2-pyrrolidin-1-yl-ethyl)-acetamide;

1-(5-tert-Butyl-isoxazol-3-yl)-3-(4-{7-[2-(4-ethyl-piperazin-1-yl)-2-oxo-ethyl]-benzo[d]imidazo[2,1-b]thiazol-2-yl}-phenyl)-urea and 1-(5-tert-Butyl-isoxazol-3-yl)-3-[4-(7-morpholin-4-ylmethyl-imidazo[2,1-b][1,3]benzothiazol-2-yl)-phenyl]-urea;

1-(5-tert-Butyl-isoxazol-3-yl)-3-{4-[7-(4-ethyl-piperazin-1-ylmethyl)-benzo[d]imidazo[2,1-b]thiazol-2-yl]-phenyl}-urea;

1-(5-tert-Butyl-isoxazol-3-yl)-3-[4-(7-piperidin-1-ylmethyl-benzo[d]imidazo[2,1-b]thiazol-2-yl)-phenyl]-urea;

1-(5-tert-Butyl-isoxazol-3-yl)-3-{4-[7-(2-morpholin-4-yl-2-oxo-ethyl)-benzo[d]imidazo[2,1-b]thiazol-2-yl]-phenyl}-urea;

1-(5-tert-Butyl-isoxazol-3-yl)-3-{4-[7-(2-morpholin-4-yl-ethyl)-imidazo[2,1-b][1,3]benzothiazol-2-yl]-phenyl}-urea;

1-(5-tert-Butyl-isoxazol-3-yl)-3-{4-[7-(2-piperidin-1-yl-ethyl)-imidazo[2,1-b][1,3]benzothiazol-2-yl]-phenyl}-urea;

1-(5-tert-Butyl-isoxazol-3-yl)-3-(4-{7-[2-(4-ethyl-piperazin-1-yl)-ethyl]-imidazo[2,1-b][1,3]benzothiazol-2-yl}-phenyl)-urea;

N-(5-tert-Butyl-isoxazol-3-yl)-N'-{4-[6-(2-morpholin-4-yl-ethoxy)imidazo[2,1-b][1,3]benzothiazol-2-yl]phenyl}urea;

2-{4-[3-(5-tert-butyl-isoxazol-3-yl)-ureido]-phenyl}-benzo[d]imidazo[2,1-b]thiazole-7-carboxylic acid (2-morpholin-4-yl-ethyl)-amide;

2-{4-[3-(5-tert-butyl-isoxazol-3-yl)-ureido]-phenyl}-benzo[d]imidazo[2,1-b]thiazole-7-carboxylic acid (2-piperidin-1-yl-ethyl)-amide;

2-{4-[3-(5-tert-butyl-isoxazol-3-yl)-ureido]-phenyl}-benzo[d]imidazo[2,1-b]thiazole-7-carboxylic acid (2-pyrrolidin-1-yl-ethyl)-amide;

2-{4-[3-(5-tert-butyl-isoxazol-3-yl)-ureido]-phenyl}-benzo[d]imidazo[2,1-b]thiazole-7-carboxylic acid (2-diethylamino-ethyl)-amide;

1-(5-tert-butyl-isoxazol-3-yl)-3-{4-[7-(4-ethyl-piperazine-1-carbonyl)-benzo[d]imidazo[2,1-b]thiazol-2-yl]-phenyl}-urea;

1-(5-tert-butyl-isoxazol-3-yl)-3-{4-[7-piperazine-1-carbonyl)-benzo[d]imidazo[2,1-b]thiazol-2-yl]-phenyl}-urea; and 1-(5-tert-butyl-isoxazol-3-yl)-3-{4-[7-(4-methyl-piperazine-1-carbonyl)-benzo[d]imidazo[2,1-b]thiazol-2-yl]-phenyl}-urea.

1-(5-tert-Butyl-isoxazol-3-yl)-3-[4-(7-hydroxy-benzo[d]imidazo[2,1-b]thiazol-2-yl)-phenyl]-urea;

1-(5-tert-Butyl-isoxazol-3-yl)-3-[4-(7-methoxy-benzo[d]imidazo[2,1-b]thiazol-2-yl)-phenyl]-urea;

1-(5-tert-Butyl-isoxazol-3-yl)-3-{4-[7-(2-diethylamino-ethoxy)-benzo[d]imidazo[2,1-b]thiazol-2-yl]-phenyl}-urea;

ethyl{2-[4-({[(5-tert-Butylisoxazol-3-yl)amino]carbonyl}amino)phenyl]imidazo[2,1-b][1,3]benzothiazol-7-yl}acetate;

3-{2-[4-({[(5-tert-Butylisoxazol-3-yl)amino]carbonyl}amino)phenyl]imidazo[2,1-b][1,3]benzothiazol-7-yl}acetic acid;

pyrrolidine-2-carboxylic acid 2-{4-[3-(5-tert-butyl-isoxazol-3-yl)-ureido]-phenyl}-benzo[d]imidazo[2,1-b]thiazol-7-yl ester;

ethyl 3-{2-[4-({[(5-tert-Butylisoxazol-3-yl)amino]carbonyl}amino)phenyl]imidazo[2,1-b][1,3]benzothiazol-7-yl}propanoate;

3-{2-[4-({[(5-tert-Butylisoxazol-3-yl)amino]carbonyl}amino)phenyl]imidazo[2,1-b][1,3]benzothiazol-7-yl}propanoic acid 3-(2-{4-[3-(5-tert-Butyl-isoxazol-3-yl)-ureido]-phenyl}-benzo[d]imidazo[2,1-b]thiazol-7-yl)-N,N-diethyl-propionamide;

2-(2-{4-[3-(5-tert-Butyl-isoxazol-3-yl)-ureido]-phenyl}-benzo[d]imidazo[2,1-b]thiazol-7-yl)-N-(2-diethylamino-ethyl)-acetamide;

3-(2-{4-[3-(5-tert-Butyl-isoxazol-3-yl)-ureido]-phenyl}-benzo[d]imidazo[2,1-b]thiazol-7-yl)-N-(2-diethylamino-ethyl)-propionamide;

2-Amino-3-methyl-butyric acid 2-{4-[3-(5-tert-butyl-isoxazol-3-yl)-ureido]-phenyl}-benzo[d]imidazo[2,1-b]thiazol-7-yl ester;

2-{4-[3-(5-tert-Butyl-isoxazol-3-yl)-ureido]-phenyl}-benzo[d]imidazo[2,1-b]thiazole-7-carboxylic acid ethyl ester; and 2-{4-[3-(5-tert-Butyl-isoxazol-3-yl)-ureido]-phenyl}-benzo[d]imidazo[2,1-b]thiazole-7-carboxylic acid.

In certain embodiments, the compound suitable for use in the methods provided herein is N-(5-tert-butyl-isoxazol-3-yl)-N'-{4-[7-(2-morpholin-4-yl-ethoxy)imidazo[2,1-b][1,3]benzothiazol-2-yl]phenyl}urea, also known as AC220, having the structure of Formula A:

colate, hemisulfate, heptanoate, hexanoate, hydrochloride, hydrobromide, hydroiodide, 2-hydroxyethanesulfonate, lactate, maleate, malonate, methanesulfonate (mesylate), 2-naphthalenesulfonate (napsylate), nicotinate, nitrate, oxalate, palmoate, pectinate, persulfate, 3-phenylpropionate, phosphate, picrate, pivalate, propionate, salicylate, succinate, sulfate, tartrate, thiocyanate, tosylate, or undecanoate salts.

In one embodiment, the pharmaceutically acceptable salt is a hydrochloride, hydrobromide, sulfate, mesylate, esylate, edisylate, besylate, tosylate, or napsylate salt of AC220. In another embodiment, the pharmaceutically acceptable salt is a hydrochloride salt of AC220. In yet another embodiment, the pharmaceutically acceptable salt is a hydrobromide of AC220. In yet another embodiment, the pharmaceutically acceptable salt is a sulfate of AC220. In yet another embodiment, the pharmaceutically acceptable salt is a mesylate of

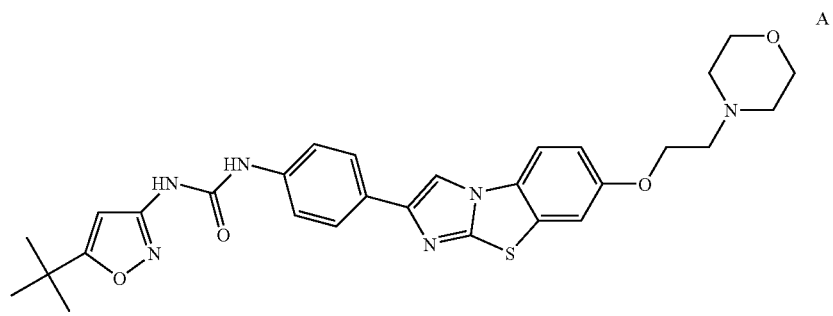 [SMILES: CC(C)(C)c1cc(NC(=O)Nc2ccc(-c3cn4c(n3)sc3cc(OCCN5CCOCC5)ccc34)cc2)no1]

or a pharmaceutically acceptable prodrug, salt, solvate or hydrate thereof.

In certain embodiments, AC220 can be prepared according to the methods described in U.S. Pat. Pub. No. 2007/0232604, the entirety of which is incorporated by reference herein. In certain embodiments, AC220 can be prepared according to the methods described in provisional patent application No. 61/258,550, the entirety of which is incorporated by reference herein. The compound can be also synthesized according to other methods apparent to those of skill in the art based upon the teaching herein.

In one embodiment, the compound used in the methods provided herein is a free base of AC220, or a pharmaceutically acceptable solvate thereof. In one embodiment, the free base is a solid. In another embodiment, the free base is a solid in an amorphous form. In yet another embodiment, the free base is a solid in a crystalline form. AC220 in solid forms can be prepared according to the method described in U.S. Pat. Pub. No. 2009/0123418, the entirety of which is incorporated by reference herein; or using other methods known in the art.

In another embodiment, the free base is a pharmaceutically acceptable solvate. In one embodiment, the free base is a hydrate. In another embodiment, the pharmaceutically acceptable solvent is a methanol solvate. The methanol solvate of AC220 can be prepared according to the method described in U.S. Pat. Pub. No. 2009/0123418; or using other methods known in the art.

In yet another embodiment, the compound used in the methods provided herein is a pharmaceutically acceptable salt of AC220, which includes, but is not limited to, acetate, adipate, alginate, aspartate, benzoate, benzenesulfonate (besylate), bisulfate, butyrate, citrate, camphorate, camphorsulfonate, cyclopentanepropionate, digluconate, dodecylsulfate, 1,2-ethanedisulfonate (edisylate), ethanesulfonate (esylate), formate, fumarate, glucoheptanoate, glycerophosphate, gly- AC220. In yet another embodiment, the pharmaceutically acceptable salt is an esylate of AC220. In yet another embodiment, the pharmaceutically acceptable salt is an edisylate of AC220. In yet another embodiment, the pharmaceutically acceptable salt is a besylate of AC220. In yet another embodiment, the pharmaceutically acceptable salt is a tosylate of AC220. In still another embodiment, the pharmaceutically acceptable salt is a napsylate of AC220. The pharmaceutically acceptable salt of AC220 can be prepared according to the method described in U.S. Pat. Pub. No. 2009/0123418; entirety of incorporated herein by reference in its entirety. The pharmaceutically acceptable salt of AC220 can also be prepared using other methods known in the art.

As used herein, AC220 is intended to encompass all possible stereoisomers, unless a particular stereochemistry is specified. Where structural isomers of AC220 are interconvertible via a low energy barrier, AC220 may exist as a single tautomer or a mixture of tautomers. This can take the form of proton tautomerism in the compound that contains, e.g., a urea group; or so-called valence tautomerism in the compound that contain an aromatic moiety.

The compound provided herein may also be provided as a prodrug, which is a functional derivative of the compound of formula (I) and is readily convertible into the parent compound in vivo. Prodrugs are often useful because, in some situations, they may be easier to administer than the parent compound. They may, for instance, be bioavailable by oral administration whereas the parent compound is not. The prodrug may also have enhanced solubility in pharmaceutical compositions over the parent compound. A prodrug may be converted into the parent drug by various mechanisms, including enzymatic processes and metabolic hydrolysis. See Harper, *Progress in Drug Research* 1962, 4, 221-294; Morozowich et al. in "Design of Biopharmaceutical Properties through Prodrugs and Analogs," Roche Ed., APHA Acad.

Pharm. Sci. 1977; "Bioreversible Carriers in Drug in Drug Design, Theory and Application," Roche Ed., APHA Acad. Pharm. Sci. 1987; "Design of Prodrugs," Bundgaard, Elsevier, 1985; Wang et al., *Curr. Pharm. Design* 1999, 5, 265-287; Pauletti et al., *Adv. Drug. Delivery Rev.* 1997, 27, 235-256; Mizen et al., *Pharm. Biotech.* 1998, 11, 345-365; Gaignault et al., *Pract. Med. Chem.* 1996, 671-696; Asgharnejad in "Transport Processes in Pharmaceutical Systems," Amidon et al., Ed., Marcell Dekker, 185-218, 2000; Balant et al., *Eur. J. Drug Metab. Pharmacokinet.* 1990, 15, 143-53; Balimane and Sinko, *Adv. Drug Delivery Rev.* 1999, 39, 183-209; Browne, *Clin. Neuropharmacol.* 1997, 20, 1-12; Bundgaard, *Arch. Pharm. Chem.* 1979, 86, 1-39; Bundgaard, *Controlled Drug Delivery* 1987, 17, 179-96; Bundgaard, *Adv. Drug Delivery Rev.* 1992, 8, 1-38; Fleisher et al., *Adv. Drug Delivery Rev.* 1996, 19, 115-130; Fleisher et al., *Methods Enzymol.* 1985, 112, 360-381; Farquhar et al., *J. Pharm. Sci.* 1983, 72, 324-325; Freeman et al., *J. Chem. Soc., Chem. Commun.* 1991, 875-877; Friis and Bundgaard, *Eur. J. Pharm. Sci.* 1996, 4, 49-59; Gangwar et al., *Des. Biopharm. Prop. Prodrugs Analogs,* 1977, 409-421; Nathwani and Wood, *Drugs* 1993, 45, 866-94; Sinhababu and Thakker, *Adv. Drug Delivery Rev.* 1996, 19, 241-273; Stella et al., *Drugs* 1985, 29, 455-73; Tan et al., *Adv. Drug Delivery Rev.* 1999, 39, 117-151; Taylor, *Adv. Drug Delivery Rev.* 1996, 19, 131-148; Valentino and Borchardt, *Drug Discovery Today* 1997, 2, 148-155; Wiebe and Knaus, *Adv. Drug Delivery Rev.* 1999, 39, 63-80; and Waller et al., *Br. J. Clin. Pharmac.* 1989, 28, 497-507.

C. SECOND AGENTS

In the methods and compositions provided herein, a compound of formula (I), AC220 or a pharmaceutically acceptable salt, prodrug, solvate or hydrate thereof can be used with or combined with one or more second active agents. Without being limited by any theory, it is believed that certain combinations work synergistically in the treatment of cancers. The methods also encompass the use of a compound of formula (I), AC220 or a pharmaceutically acceptable salt, prodrug, solvate or hydrate thereof in a manner to alleviate, reduce or avoid adverse effects associated with certain second active agents. Also provided are methods, wherein the second active agents are used in the manner to alleviate, reduce or avoid adverse or unwanted effects associated with a compound of formula (I), AC220 or a pharmaceutically acceptable salt, prodrug, solvate or hydrate thereof.

One or more second active ingredients or agents can be used together with a compound of formula (I) or AC220 or a pharmaceutically acceptable prodrug, salt, solvate or hydrate thereof in the methods and compositions provided herein.

In certain embodiments, the second agent is a nucleoside or analog thereof. The term "nucleoside analog" denotes an organic compound containing a nucleobase bound to a carbohydrate ring via a nitrogen atom of the nucleobase. In one embodiment, the nucleobase is a nitrogenous base. In another embodiment, the carbohydrate ring is a sugar ring. The nucleoside analog optionally contains a phosphate moiety.

Examples of the nitrogenous base include, but are not limited to purine and their derivatives, such as adenine, guanine, and hypoxanthine, and pyrimidine and their derivatives, such as cytosine, uracil, thymine, and 4-amino-triazin-2(1H)-one (an aza derivative of cytosine). In certain embodiments, the nucleoside analog is a neoplastic cell antimetaboite, i.e., a compound that interferes with the biological functions of neoplastic cells. For example, the nucleoside analog may interfere with DNA methylation, DNA synthesis, and other functions related to cell division.

In certain embodiments, the nucleoside analog is a compound having formula (II):

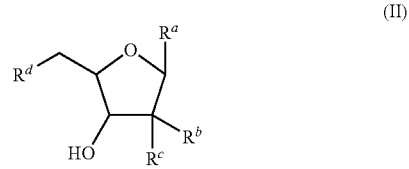

wherein $R^a$, $R^b$, $R^c$ and $R^d$ are selected from (i), (ii) and (iii) as follows:
(i) $R^a$ is:

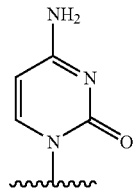

$R^b$ is hydroxy, and $R^c$ and $R^d$ are fluoro;
(ii) $R^a$ is

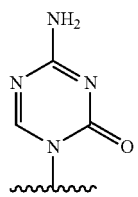 [SMILES: *n1cnc(N)nc1=O]

$R^b$ is hydroxy, and one of $R^c$ and $R^d$ is hydrogen and the other of $R^c$ and $R^d$ is hydrogen or hydroxy; and
(iii) $R^a$ is

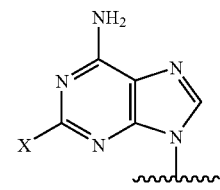

wherein X is fluoro or chloro,
$R^b$ is —OP(O)(OH)$_2$ or hydroxy, and one of $R^c$ and $R^d$ is hydrogen and the other of $R^c$ and $R^d$ is hydrogen, fluoro or hydroxy.

In one embodiment, the nucleoside analog is a DNA synthesis inhibitor. In another embodiment, the nucleoside analog is a DNA methylation inhibitor, also known as a demethylation agent. In one embodiment, the nucleoside analog comprises a phosphate moiety. For example, the nucleoside analog can be fludarabine phosphate. In another embodiment, the nucleoside analog does not comprise a phosphate moiety. For example, the nucleoside analog can be selected from the group consisting of decitabine, azacitidine (also known as 5-aza-cytidine, Aza-C, 5-Aza-C, and VIDAZA®), clofarabine (also known as Clolar®), cladribine (also known as 2CdA and Leustatin®), cytarabine (also known as cytosine arabinoside, AraC, CYTOSAR-U®, Tarabine PFS, and Depocyt®), decitabine, fludarabine, gemcitabine (also known as Gemzar®) and a combination thereof.

In one embodiment, the nucleoside analog is an epigenetic agent. By "epigenetic agent", it is meant a compound that can regulate key cell cycle control genes and tumor suppressor genes. For example, the epigenetic agent may silence key cell cycle control genes and tumor suppressor genes through DNA methylation and/or histone deacetylation, which are two of the epigenetic regulators of gene expression. Example of the epigenetic agent includes, but is not limited to azacitidine.

The above-described nucleoside analog can be synthesized via methods known to one skilled in the art or obtained through commercial sources.

In certain embodiments, the second active agent is selected from an anthracycline and a topoisomerase inhibitor. In one embodiment, the topoisomerase inhibitor is selected from amsacrine, etoposide, etoposide phosphate, and teniposide. In one embodiment, the topoisomerase inhibitor is etoposide.

The above-described topoisomerase inhibitors can be synthesized via methods known to one skilled in the art or obtained through commercial sources.

In one embodiment, the anthracycline is selected from daunorubicin, doxorubicin, epirubicin, idarubicin, mitoxantrone, amrubicin and valrubicin. In one embodiment, the anthracycline is daunorubicin. In certain embodiments, the compound of formula (I) or AC220 or a pharmaceutically acceptable prodrug, salt, solvate or hydrate thereof is administered in combination with cytarabine and daunorubicin.

The above-described anthracyclines can be synthesized via methods known to one skilled in the art or obtained through commercial sources.

In the combination therapy provided herein, AC220 and the second agent can be administered simultaneously or sequentially with AC220. In certain embodiments, AC220 and the second agent selected from a nucleoside analog, an anthracycline and a topoisomerase inhibitor are used in combination methods that may also include the use of one or more other therapies including, but not limited to, treatment with a therapeutic antibody that specifically binds to a cancer antigen, hematopoietic growth factor, cytokine, other anti-cancer agent, antibiotic, cox-2 inhibitor, immunomodulatory agent, immunosuppressive agent, corticosteroid or a pharmacologically active mutant or derivative thereof, anti-cancer agents, radiation therapy, anti-emetics and the like.

In certain embodiments, use of a second active agent in combination with a compound of formula (I) may be modified or delayed during or shortly following administration of a compound of formula (I) as deemed appropriate by the practitioner of skill in the art. In certain embodiments, subjects being administered a compound of formula (I) in combination with the second agents may receive supportive care including antiemetics, when appropriate.

In certain embodiments, use of a second active agent in combination with AC220 may be modified or delayed during or shortly following administration of AC220 as deemed appropriate by the practitioner of skill in the art. In certain embodiments, subjects being administered AC220 in combination with the second agents may receive supportive care including antiemetics, when appropriate.

D. METHODS OF TREATMENT AND PREVENTION

In one embodiment, provided herein is a method for treating a proliferative disease in a mammal, which comprises administering to the mammal having the proliferative disease a therapeutically effective amount of a compound of formula (I), or a pharmaceutically acceptable prodrug, salt, solvate or hydrate thereof in combination with a therapeutically effective amount of a second active agent selected from a nucleoside analog, an anthracycline and a topoisomerase inhibitor, or a combination thereof.

In one embodiment, the compound having structural formula (I), or a salt, solvate, ester and/or prodrug thereof, is administered at a dose from about 12 mg/day to about 500 mg/day. In one embodiment, the compound having structural formula (I), or a salt, solvate, ester and/or prodrug thereof, is administered at a dose from about 30 mg/day to about 500 mg/day. In one embodiment, the nucleoside analog is administered at a dose from about 5 mg/m$^2$ to about 3 g/m$^2$. In one embodiment, the nucleoside analog is administered at a dose from about 5 mg/m$^2$ to about 150 mg/m$^2$. For example, azacitidine may be administered at a dose from about 50 mg/m$^2$/day to about 100 mg/m$^2$/day, or about 75 mg/m$^2$/day; clofarabine may be administered at a dose from about 11.25 mg/m$^2$/day to about 70 mg/m$^2$/day, or about 40 mg/m$^2$/day to about 52 mg/m$^2$/day; cytarabine may be administered intrathecally at a dose from about 5 mg/m$^2$ to about 75 mg/m$^2$ once per day or once every four days with about 30 mg/m$^2$ every four days, or intravenously from about 5 mg/m$^2$/day to about 3 g/m$^2$/day with from about 100 mg/m$^2$/day to about 200 mg/m$^2$/day; decitabine may be administered at a dose from about 33 mg/m$^2$/day to about 45 mg/m$^2$/day or about 45 mg/m$^2$/day; and fludarabine may be administered at a dose from about 15 mg/m$^2$/day to about 40 mg/m$^2$/day, or about 25 mg/m$^2$/day.

The administered dose may be expressed in units of mg/m$^2$/day in which a patient's body surface area (BSA) may be calculated in m$^2$ using various available formulae using the patient's height and weight. The administered dose may alternatively be expressed in units of mg/day which does not take into consideration the patient's BSA. One of skill in the art can convert from one unit to another based on a patient's height and weight.

In certain embodiments, the therapeutically effective amount of AC220 is a range from about 12 to about 1,000 mg per day, from about 12 to about 500 mg per day, from about 12 to about 450 mg per day, from about 12 to about 300 mg per day, from about 12 to about 200 mg per day, from about 12 to about 100 mg per day, from about 12 to about 90 mg per day, from about 12 to about 80 mg per day, from about 12 to about 70 mg per day, from about 15 to about 65 mg per day, or from about 20 to about 60 mg per day. In one embodiment, the therapeutically effective amount of AC220 is from about 12 to about 1,000 mg per day. In another embodiment, the therapeutically effective amount of AC220 is from about 12 to about 500 mg per day. In yet another embodiment, the therapeutically effective amount of AC220 is from about 12 to about 450 mg per day. In yet another embodiment, the therapeutically effective amount of AC220 is from about 12 to about 400 mg per day. In yet another embodiment, the therapeutically effective amount of AC220 is from about 12 to about 300 mg per day. In yet another embodiment, the therapeutically effective amount of AC220 is from about 12 to about 200 mg per day. In yet another embodiment, the therapeutically effective amount of AC220 is from about 12 to about 150 mg per day. In yet another embodiment, the therapeutically effective amount of AC220 is from about 12 to about 100 mg per day. In yet another embodiment, the therapeutically effective amount of AC220 is from about 12 to about 90 mg per day. In yet another embodiment, the therapeutically effective amount of AC220 is from about 12 to about 80 mg per day. In yet another embodiment, the therapeutically effective amount of AC220 is from about 12 to about 70 mg per day. In yet another embodiment, the therapeutically effective amount of AC220 is from about 15 to about 65 mg per day. In still another embodiment, the therapeutically effective amount of AC220 is from about 20 to about 60 mg per day.

In certain embodiments, the therapeutically effective amount of AC220 is about 12, about 18, about 20, about 25, about 27, about 30, about 35, about 40, about 45, about 50, about 55, about 60, about 90, about 100, about 135, about 150, about 200, about 300, or about 450 mg per day. In certain embodiments, the therapeutically effective amount of AC220 in a combination regimen is about 12, about 18, about 20, about 25, about 27, about 30, about 35, about 40, about 45, about 50, about 55, about 60, about 75, about 90, about 100, about 125, about 135, about 150, about 175, about 200, about 225, about 250, about 300, about 450 or about 500 mg per day. In one embodiment, the therapeutically effective amount of AC220 is about 12 mg per day. In another embodiment, the therapeutically effective amount of AC220 is about 18 mg per day. In yet another embodiment, the therapeutically effective amount of AC220 is about 20 mg per day. In yet another embodiment, the therapeutically effective amount of AC220 is about 25 mg per day. In yet another embodiment, the therapeutically effective amount of AC220 is about 27 mg per day. In yet another embodiment, the therapeutically effective amount of AC220 is about 30 mg per day. In yet another embodiment, the therapeutically effective amount of AC220 is about 35 mg per day. In yet another embodiment, the therapeutically effective amount of AC220 is about 40 mg per day. In yet another embodiment, the therapeutically effective amount of AC220 is about 45 mg per day. In yet another embodiment, the therapeutically effective amount of AC220 is about 50 mg per day. In yet another embodiment, the therapeutically effective amount of AC220 is about 55 mg per day. In yet another embodiment, the therapeutically effective amount of AC220 is about 60 mg per day. In yet another embodiment, the therapeutically effective amount of AC220 is about 75 mg per day. In yet another embodiment, the therapeutically effective amount of AC220 is about 90 mg per day. In yet another embodiment, the therapeutically effective amount of AC220 is about 100 mg per day. In yet another embodiment, the therapeutically effective amount of AC220 is about 125 mg per day. In yet another embodiment, the therapeutically effective amount of AC220 is about 135 mg per day. In yet another embodiment, the therapeutically effective amount of AC220 is about 150 mg per day. In yet another embodiment, the therapeutically effective amount of AC220 is about 175 mg per day. In yet another embodiment, the therapeutically effective amount of AC220 is about 200 mg per day. In yet another embodiment, the therapeutically effective amount of AC220 is about 225 mg per day. In yet another embodiment, the therapeutically effective amount of AC220 is about 250 mg per day. In yet another embodiment, the therapeutically effective amount of AC220 is about 275 mg per day. In still another embodiment, the therapeutically effective amount of AC220 is about 300 mg per day. In yet another embodiment, the therapeutically effective amount of AC220 is about 350 mg per day. In still another embodiment, the therapeutically effective amount of AC220 is about 450 mg per day.

In certain embodiments, the therapeutically effective amount of AC220 is a range from about 0.2 to about 20 mg/kg/day, from about 0.2 to about 15 mg/kg/day, from about 0.2 to about 10 mg/kg/day, from about 0.2 to about 9 mg/kg/day, from about 0.2 to about 8 mg/kg/day, from about 0.2 to about 7 mg/kg/day, from about 0.2 to about 6 mg/kg/day, from about 0.2 to about 5 mg/kg/day, from about 0.2 to about 5 mg/kg/day, from about 0.2 to about 5 mg/kg/day, from about 0.2 to about 4 mg/kg/day, from about 0.2 to about 3 mg/kg/day, from about 0.2 to about 2 mg/kg/day, from about 0.2 to about 1 mg/kg/day, or from about 0.24 mg/kg/day to about 9 mg/kg/day.

In one embodiment, the therapeutically effective amount of AC220 is from about 0.2 to about 20 mg/kg/day. In another embodiment, the therapeutically effective amount is from about 0.2 to about 15 mg/kg/day. In yet another embodiment, the therapeutically effective amount is from about 0.2 to about 10 mg/kg/day. In yet another embodiment, the therapeutically effective amount is from about 0.2 to about 9 mg/kg/day. In yet another embodiment, the therapeutically effective amount is from about 0.2 to about 8 mg/kg/day. In yet another embodiment, the therapeutically effective amount is from about 0.2 to about 7 mg/kg/day. In yet another embodiment, the therapeutically effective amount is from about 0.2 to about 6 mg/kg/day. In yet another embodiment, the therapeutically effective amount is from about 0.2 to about 5 mg/kg/day. In yet another embodiment, the therapeutically effective amount is from about 0.2 to about 5 mg/kg/day. In yet another embodiment, the therapeutically effective amount is from about 0.2 to about 4 mg/kg/day. In yet another embodiment, the therapeutically effective amount is from about 0.2 to about 3 mg/kg/day. In yet another embodiment, the therapeutically effective amount is from about 0.2 to about 2 mg/kg/day. In yet another embodiment, the therapeutically effective amount is from about 0.2 to about 1 mg/kg/day. In still another embodiment, the therapeutically effective amount is from about 0.24 to about 9 mg/kg/day.

The administered dose can also be expressed in units other than as mg/kg/day. For example, doses for parenteral administration can be expressed as mg/m$^2$/day. One of ordinary skill in the art would readily know how to convert doses from mg/kg/day to mg/m$^2$/day to given either the height or weight of a subject or both (see, www.fda.gov/cder/cancer/animalframe.htm). For example, a dose of 1 mg/kg/day for a 65 kg human is approximately equal to 38 mg/m$^2$/day.

In certain embodiments, compound I is administered in an amount sufficient to provide a plasma concentration of the compound at steady state, ranging from about 0.0.02 to about 100 µM, from about 0.1 to about 10 µM, from about 0.3 to about 10 µM, from about 0.9 to about 5 µM, from about 1 to about 4 µM, from about 1 to about 3 µM or from about 1.5 to about 3 µM. In one embodiment, the amount of the compound administered is sufficient to provide a maximum plasma concentration of the compound of about 0.02 to about 100 µM. In another embodiment, the amount of the compound administered is sufficient to provide a maximum plasma concentration of the compound of about 0.1 to about 10 µM. In yet another embodiment, the amount of the compound administered is sufficient to provide a maximum plasma concentration of the compound of about 0.3 to about 10 µM. In yet another embodiment, the amount of the compound administered is sufficient to provide a maximum plasma concentration of the compound of about 0.9 to about 5 µM. In yet another embodiment, the amount of the compound administered is sufficient to provide a maximum plasma concentration of the compound of about 1 to about 4 µM. In yet another embodiment, the amount of the compound administered is sufficient to provide a maximum plasma concentration of the compound of about 1 to about 3 µM. In yet another embodiment, the amount of the compound administered is sufficient to provide a maximum plasma concentration of the compound of about 1.5 to about 3 µM. As used herein, the term "plasma concentration at steady state" is the concentration reached after a period of administration of a compound. Once steady state is reached, there are minor peaks and troughs on the time dependent curve of the plasma concentration of the compound.

In yet another embodiment, compound I is administered in an amount sufficient to provide a maximum plasma concentration (peak concentration) of the compound, ranging from about 0.0.02 to about 100 μM, from about 0.1 to about 10 μM, from about 0.3 to about 10 μM, from about 0.9 to about 5 μM, from about 1 to about 4 μM, from about 1 to about 3 μM or from about 1.5 to about 3 μM. In one embodiment, the amount of the compound administered is sufficient to provide a maximum plasma concentration of the compound of about 0.02 to about 100 μM. In another embodiment, the amount of the compound administered is sufficient to provide a maximum plasma concentration of the compound of about 0.1 to about 10 μM. In yet another embodiment, the amount of the compound administered is sufficient to provide a maximum plasma concentration of the compound of about 0.3 to about 10 μM. In yet another embodiment, the amount of the compound administered is sufficient to provide a maximum plasma concentration of the compound of about 0.9 to about 5 μM. In yet another embodiment, the amount of the compound administered is sufficient to provide a maximum plasma concentration of the compound of about 1 to about 4 μM. In yet another embodiment, the amount of the compound administered is sufficient to provide a maximum plasma concentration of the compound of about 1 to about 3 μM. In yet another embodiment, the amount of the compound administered is sufficient to provide a maximum plasma concentration of the compound of about 1.5 to about 3 μM.

In yet another embodiment, compound I is administered in an amount sufficient to provide a minimum plasma concentration (trough concentration) of the compound, ranging from about 0.02 to about 10 μM, from about 0.1 to about 10 μM, from about 0.3 to about 10 μM, from about 0.6 to about 5 μM, about 0.6 to about 3 μM, from about 0.9 to about 3 μM, or from about 1.5 to about 3 μM, when more than one doses are administered. In one embodiment, the amount of the compound administered is sufficient to provide a minimum plasma concentration of the compound of about 0.02 to about 10 μM. In another embodiment, the amount of the compound administered is sufficient to provide a minimum plasma concentration of the compound of about 0.1 to about 10 μM. In yet another embodiment, the amount of the compound administered is sufficient to provide a minimum plasma concentration of the compound of about 0.3 to about 10 μM. In yet another embodiment, the amount of the compound administered is sufficient to provide a minimum plasma concentration of the compound of about 0.6 to about 5 μM. In yet another embodiment, the amount of the compound administered is sufficient to provide a minimum plasma concentration of the compound of about 0.6 to about 3 μM. In yet another embodiment, the amount of the compound administered is sufficient to provide a minimum plasma concentration of the compound of about 0.9 to about 3 μM. In yet another embodiment, the amount of the compound administered is sufficient to provide a minimum plasma concentration of the compound of about 1.5 to about 3 μM.

In still another embodiment, compound I is administered in an amount sufficient to provide an area under the curve (AUC) of the compound, ranging from about 100 to about 50,000 ng*hr/mL, from about 1000 to about 50,000 ng*hr/mL, from about 1500 to about 40,000 ng*hr/mL from about 2,000 to about 35,000 ng*hr/mL, from about 2000 to about 35,000 ng*hr/mL, from about 9,000 to about 35,000 ng*hr/mL, or from about 10,000 to about 25,000 ng*hr/mL.

Depending on the disease to be treated and the subject's condition, AC220 or a pharmaceutically acceptable salt, solvate, hydrate, or prodrug thereof can be administered by oral, parenteral (e.g., intramuscular, intraperitoneal, intravenous, CIV, intracisternal injection or infusion, subcutaneous injection, or implant), inhalation, nasal, vaginal, rectal, sublingual, or topical (e.g., transdermal or local) routes of administration. AC220 or a pharmaceutically acceptable salt, solvate, hydrate, or prodrug thereof may be formulated, alone or together, in suitable dosage unit with pharmaceutically acceptable excipients, carriers, adjuvants and vehicles, appropriate for each route of administration.

In one embodiment, AC220 or a pharmaceutically acceptable salt, solvate, hydrate, or prodrug thereof can be delivered as a single dose such as, e.g., a single bolus injection, or oral tablets or pills; or over time such as, e.g., continuous infusion over time or divided bolus doses over time.

In one embodiment, AC220 or a pharmaceutically acceptable salt, solvate, hydrate, or prodrug thereof can be administered once daily (QD), or divided into multiple daily doses such as twice daily (BID), three times daily (TID), and four times daily (QID). In addition, the administration can be continuous, i.e., every day, or intermittently. The term "intermittent" or "intermittently" as used herein is intended to mean stopping and starting at either regular or irregular intervals. For example, intermittent administration of the compound is administration for one to six days per week, administration in cycles (e.g., daily administration for two to eight consecutive weeks, then a rest period with no administration for up to one week), or administration on alternate days.

In certain embodiments, the frequency of administration of AC220 is in the range of about a daily dose to about a monthly dose. In certain embodiments, the administration of AC220 is once a day, twice a day, three times a day, four times a day, once every other day, twice a week, once every week, once every two weeks, once every three weeks, or once every four weeks. In one embodiment, AC220 provided herein is administered once a day. In another embodiment, AC220 provided herein is administered twice a day. In yet another embodiment, AC220 provided herein is administered three times a day. In still another embodiment, AC220 provided herein is administered four times a day.

In certain embodiments, AC220 is administered for 7 days in a 21 day cycle. In certain embodiments, AC220 is administered for 7 days in a 28 day cycle. In certain embodiments, AC220 is administered for 14 days in a 28 day cycle. In certain embodiments, AC220 is administered for 28 days in a 28 day cycle.

In certain embodiments, AC220, or a pharmaceutically acceptable prodrug, salt, solvate or hydrate thereof is administered once per day for about 1 week, 2 weeks, 3 weeks, about 4 weeks, about 6 weeks, about 9 weeks, about 12 weeks, about 15 weeks, about 18 weeks, about 21 weeks, or about 26 weeks. In certain embodiments, AC220 is administered intermittently. In certain embodiments, AC220 is administered intermittently in the amount of from about 40 to 450 mg per day. In certain embodiments, AC220 is administered continuously. In certain embodiments, AC220 is administered continuously in the amount ranging from about 12 mg to 1000 mg per day. In certain embodiments, AC220 is administered continuously in the amount ranging from about 12 mg to 2000 mg per day, or from about 27 mg to 1000 mg per day. In certain embodiments, AC220 is administered continuously in the amount ranging from about 200 mg to 1000 mg per day. In certain embodiments, AC220 is administered continuously in the amount ranging from about 200 mg to 675 mg per day. In certain embodiments, AC220 is administered continuously in the amount ranging from about 200 mg to 450 mg per day. In certain embodiments, AC220 is administered continuously for 28 days. In certain embodiments, AC220 is administered continuously in the amount of about 200 mg. In certain embodiments, AC220 is administered continuously in the amount of about 450 mg. In certain embodiments, AC220 is administered continuously in the amount of about 675 mg. In certain embodiments, AC220 is administered continuously in the amount of about 1000 mg.

In one embodiment, AC220, or a pharmaceutically acceptable prodrug, salt, solvate or hydrate thereof, is administered daily in a single or divided doses for one week, two weeks, three weeks, four weeks, five weeks, six weeks, eight weeks, ten weeks, fifteen weeks, or twenty weeks, followed by a rest period of about 1 day to about ten weeks. For example, the methods contemplate using cycling of one week, two weeks, three weeks, four weeks, five weeks, six weeks, eight weeks, ten weeks, fifteen weeks, or twenty weeks. In another embodiment, AC220, or a pharmaceutically acceptable prodrug, salt, solvate or hydrate thereof, is administered daily in a single or divided doses for one week, two weeks, three weeks, four weeks, five weeks, or six weeks with a rest period of 1, 3, 5, 7, 9, 12, 14, 16, 18, 20, 22, 24, 26, 28, 29, or 30 days. In some embodiments, the rest period is 14 days. In some embodiments, the rest period is 28 days. In one embodiment, the rest period is a period that is sufficient for bone marrow recovery. The frequency, number and length of dosing cycles can be increased or decreased.

In certain embodiments, the route of administration of AC220 is independent of the route of administration of a second therapy. In one embodiment, AC220 is administered orally. In another embodiment, AC220 is administered intravenously. Thus, in accordance with these embodiments, AC220 is administered orally or intravenously, and the second therapy can be administered orally, parenterally, intraperitoneally, intravenously, intraarterially, transdermally, sublingually, intramuscularly, rectally, transbuccally, intranasally, liposomally, via inhalation, vaginally, intraocularly, via local delivery by catheter or stent, subcutaneously, intraadiposally, intraarticularly, intrathecally, or in a slow release dosage form. In one embodiment, AC220 and a second therapy are administered by the same mode of administration, orally or by IV. In another embodiment, AC220 is administered by one mode of administration, e.g., by IV, whereas the second agent is administered by another mode of administration, e.g., orally.

In certain embodiments, the methods provided herein are for treatment of a human.

In one embodiment, the proliferative disease is a tumor. In another embodiment, the proliferative disease is a solid tumor. In another embodiment, the proliferative disease is cancer. In another embodiment, the disease is a hematological neoplasm.

In certain embodiments, the cancer treatable with the methods provided herein includes, but is not limited to, (1) leukemias, including, but not limited to, acute leukemia, acute lymphocytic leukemia, acute myelocytic leukemias such as myeloblastic, promyelocytic, myelomonocytic, monocytic, erythroleukemia leukemias and myelodysplastic syndrome or a symptom thereof (such as anemia, thrombocytopenia, neutropenia, bicytopenia or pancytopenia), refractory anemia (RA), RA with ringed sideroblasts (RARS), RA with excess blasts (RAEB), RAEB in transformation (RAEB-T), preleukemia, and chronic myelomonocytic leukemia (CMML), (2) chronic leukemias, including, but not limited to, chronic myelocytic (granulocytic) leukemia, chronic lymphocytic leukemia, and hairy cell leukemia; (3) polycythemia vera; (4) lymphomas, including, but not limited to, Hodgkin's disease and non-Hodgkin's disease; (5) multiple myelomas, including, but not limited to, smoldering multiple myeloma, nonsecretory myeloma, osteosclerotic myeloma, plasma cell leukemia, solitary plasmacytoma, and extramedullary plasmacytoma; (6) Waldenström's macroglobulinemia; (7) monoclonal gammopathy of undetermined significance; (8) benign monoclonal gammopathy; (9) heavy chain disease; (10) bone and connective tissue sarcomas, including, but not limited to, bone sarcoma, osteosarcoma, chondrosarcoma, Ewing's sarcoma, malignant giant cell tumor, fibrosarcoma of bone, chordoma, periosteal sarcoma, soft-tissue sarcomas, angiosarcoma (hemangiosarcoma), fibrosarcoma, Kaposi's sarcoma, leiomyosarcoma, liposarcoma, lymphangiosarcoma, metastatic cancers, neurilemmoma, rhabdomyosarcoma, and synovial sarcoma; (11) brain tumors, including, but not limited to, glioma, astrocytoma, brain stem glioma, ependymoma, oligodendroglioma, nonglial tumor, acoustic neurinoma, craniopharyngioma, medulloblastoma, meningioma, pineocytoma, pineoblastoma, and primary brain lymphoma; (12) breast cancer, including, but not limited to, adenocarcinoma, lobular (small cell) carcinoma, intraductal carcinoma, medullary breast cancer, mucinous breast cancer, tubular breast cancer, papillary breast cancer, primary cancers, Paget's disease, and inflammatory breast cancer; (13) adrenal cancer, including, but not limited to, pheochromocytom and adrenocortical carcinoma; (14) thyroid cancer, including, but not limited to, papillary or follicular thyroid cancer, medullary thyroid cancer, and anaplastic thyroid cancer; (15) pancreatic cancer, including, but not limited to, insulinoma, gastrinoma, glucagonoma, vipoma, somatostatin-secreting tumor, and carcinoid or islet cell tumor; (16) pituitary cancer, including, but limited to, Cushing's disease, prolactin-secreting tumor, acromegaly, and diabetes insipius; (17) eye cancer, including, but not limited, to ocular melanoma such as iris melanoma, choroidal melanoma, and cilliary body melanoma, and retinoblastoma; (18) vaginal cancer, including, but not limited to, squamous cell carcinoma, adenocarcinoma, and melanoma; (19) vulvar cancer, including, but not limited to, squamous cell carcinoma, melanoma, adenocarcinoma, basal cell carcinoma, sarcoma, and Paget's disease; (20) cervical cancers, including, but not limited to, squamous cell carcinoma, and adenocarcinoma; (21) uterine cancer, including, but not limited to, endometrial carcinoma and uterine sarcoma; (22) ovarian cancer, including, but not limited to, ovarian epithelial carcinoma, borderline tumor, germ cell tumor, and stromal tumor; (23) esophageal cancer, including, but not limited to, squamous cancer, adenocarcinoma, adenoid cystic carcinoma, mucoepidermoid carcinoma, adenosquamous carcinoma, sarcoma, melanoma, plasmacytoma, verrucous carcinoma, and oat cell (small cell) carcinoma; (24) stomach cancer, including, but not limited to, adenocarcinoma, fungating (polypoid), ulcerating, superficial spreading, diffusely spreading, malignant lymphoma, liposarcoma, fibrosarcoma, and carcinosarcoma; (25) colon cancer; (26) rectal cancer; (27) liver cancer, including, but not limited to, hepatocellular carcinoma and hepatoblastoma; (28) gallbladder cancer, including, but not limited to, adenocarcinoma; (29) cholangiocarcinomas, including, but not limited to, pappillary, nodular, and diffuse; (30) lung cancer, including, but not limited to, non-small cell lung cancer, squamous cell carcinoma (epidermoid carcinoma), adenocarcinoma, large-cell carcinoma, and small-cell lung cancer; (31) testicular cancer, including, but not limited to, germinal tumor, seminoma, anaplastic, classic (typical), spermatocytic, nonseminoma, embryonal carcinoma, teratoma carcinoma, and choriocarcinoma (yolk-sac tumor); (32) prostate cancer, including, but not limited to, adenocarcinoma, leiomyosarcoma, and rhabdomyosarcoma; (33) penal cancer; (34) oral cancer, including, but not limited to, squamous cell carcinoma; (35) basal cancer; (36) salivary gland cancer, including, but not limited to, adenocarcinoma, mucoepidermoid carcinoma, and adenoidcystic carcinoma; (37) pharynx cancer, including, but not limited to, squamous cell cancer and verrucous; (38) skin cancer, including, but not limited to, basal cell carcinoma, squamous cell carcinoma and melanoma, superficial spreading melanoma, nodular melanoma, lentigo malignant melanoma, and acral lentiginous melanoma; (39) kidney cancer, including, but not limited to, renal cell cancer, adenocarcinoma, hypernephroma, fibrosarcoma, and transitional cell cancer (renal pelvis and/or uterer); (40) Wilms' tumor; (41) bladder cancer, including, but not limited to, transitional cell carcinoma, squamous cell cancer, adenocarcinoma, and carcinosarcoma; and other cancer, including, not limited to, myxosarcoma, osteogenic sarcoma, endotheliosarcoma, lymphangio-endotheliosarcoma, mesothelioma, synovioma, hemangioblastoma, epithelial carcinoma, cystadenocarcinoma, bronchogenic carcinoma, sweat gland carcinoma, sebaceous gland carcinoma, papillary carcinoma, and papillary adenocarcinomas (See Fishman et al., 1985, *Medicine*, 2d Ed., J.B. Lippincott Co., Philadelphia and Murphy et al., 1997, *Informed Decisions: The Complete Book of Cancer Diagnosis, Treatment, and Recovery*, Viking Penguin, Penguin Books U.S.A., Inc., United States of America).

In certain embodiments, the cancer that is treatable with the methods provided herein includes, but is not limited to, bladder cancer, breast cancer, cervical cancer, colon cancer (e.g., colorectal cancer), endometrial cancer, gastric cancer, glioma (e.g., glioblastoma), head and neck cancer, liver cancer, non-small cell lung cancer, ovarian cancer, pancreatic cancer, and prostate cancer.

In certain embodiments, the cancer is a metastatic cancer, including, but not limited to, bladder cancer, breast cancer, cervical cancer, colon cancer (e.g., colorectal cancer), esophageal cancer, head and neck cancer, liver cancer, lung cancer (e.g., small cell and non-small cell lung cancers), melanoma, myeloma, neuroblastoma, ovarian cancer, pancreatic cancer, prostate cancer, renal cancer, sarcoma (e.g., osteosarcoma), skin cancer (e.g., squamous cell carcinoma), stomach cancer, testicular cancer, thyroid cancer, and uterine cancer. In one embodiment, the metastatic cancer is breast or prostate cancer. In another embodiment, the metastatic cancer is breast cancer. In yet another embodiment, the metastatic cancer is prostate cancer.

In one embodiment, the leukemia is chronic lymphocytic leukemia, chronic myelocytic leukemia, acute lymphoblastic leukemia, acute myelogenous leukemia, and acute myeloblastic leukemia.

In another embodiment, the leukemia is acute leukemia. In one embodiment, the acute leukemia is acute myelogenous leukemia (AML). In one embodiment, acute myelogenous leukemia is undifferentiated AML (M0), myeloblastic leukemia (M1), myeloblastic leukemia (M2), promyelocytic leukemia (M3 or M3 variant [M3V]), myelomonocytic leukemia (M4 or M4 variant with eosinophilia [M4E]), monocytic leukemia (M5), erythroleukemia (M6), or megakaryoblastic leukemia (M7). In another embodiment, the acute myelogenous leukemia is undifferentiated AML (M0). In yet another embodiment, the acute myelogenous leukemia is myeloblastic leukemia (M1). In yet another embodiment, the acute myelogenous leukemia is myeloblastic leukemia (M2). In yet another embodiment, the acute myelogenous leukemia is promyelocytic leukemia (M3 or M3 variant [M3V]). In yet another embodiment, the acute myelogenous leukemia is myelomonocytic leukemia (M4 or M4 variant with eosinophilia [M4E]). In yet another embodiment, the acute myelogenous leukemia is monocytic leukemia (M5). In yet another embodiment, the acute myelogenous leukemia is erythroleukemia (M6). In yet another embodiment, the acute myelogenous leukemia is megakaryoblastic leukemia (M7). In yet another embodiment, the acute myelogenous leukemia is promyelocytic leukemia. In yet another embodiment, the leukemia is attributable to a FLT3 internal tandem duplication (ITD) mutation. In yet another embodiment, the leukemia is attributable to a FLT3 point mutation. In still another embodiment, the FLT3 point mutation is a point mutation at amino acid D835.

In another embodiment, the acute leukemia is acute lymphocytic leukemia (ALL). In one embodiment, the acute lymphocytic leukemia is leukemia that originates in the blast cells of the bone marrow (B-cells), thymus (T-cells), or lymph nodes. The acute lymphocytic leukemia is categorized according to the French-American-British (FAB) Morphological Classification Scheme as L1—Mature-appearing lymphoblasts (T-cells or pre-B-cells), L2—Immature and pleomorphic (variously shaped) lymphoblasts (T-cells or pre-B-cells), and L3—Lymphoblasts (B-cells; Burkitt's cells). In another embodiment, the acute lymphocytic leukemia originates in the blast cells of the bone marrow (B-cells). In yet another embodiment, the acute lymphocytic leukemia originates in the thymus (T-cells). In yet another embodiment, the acute lymphocytic leukemia originates in the lymph nodes. In yet another embodiment, the acute lymphocytic leukemia is L1 type characterized by mature-appearing lymphoblasts (T-cells or pre-B-cells). In yet another embodiment, the acute lymphocytic leukemia is L2 type characterized by immature and pleomorphic (variously shaped) lymphoblasts (T-cells or pre-B-cells). In yet another embodiment, the acute lymphocytic leukemia is L3 type characterized by lymphoblasts (B-cells; Burkitt's cells).

In yet another embodiment, the leukemia is T-cell leukemia. In one embodiment, the T-cell leukemia is peripheral T-cell leukemia, T-cell lymphoblastic leukemia, cutaneous T-cell leukemia, and adult T-cell leukemia. In another embodiment, the T-cell leukemia is peripheral T-cell leukemia. In yet another embodiment, the T-cell leukemia is T-cell lymphoblastic leukemia. In yet another embodiment, the T-cell leukemia is cutaneous T-cell leukemia. In still another embodiment, the T-cell leukemia is adult T-cell leukemia.

In yet another embodiment, the leukemia is Philadelphia positive. In one embodiment, the Philadelphia positive leukemia is Philadelphia positive AML, including, but not limited to, undifferentiated AML (M0), myeloblastic leukemia (M1), myeloblastic leukemia (M2), promyelocytic leukemia (M3 or M3 variant [M3V]), myelomonocytic leukemia (M4 or M4 variant with eosinophilia [M4E]), monocytic leukemia (M5), erythroleukemia (M6), or megakaryoblastic leukemia (M7). In another embodiment, the Philadelphia positive leukemia is Philadelphia positive ALL.

In still another embodiment, the leukemia is drug resistant. In one embodiment, the subject has developed drug resistance to the anticancer therapy. In another embodiment, the subject has developed drug resistance to a FLT3 kinase inhibitor. In yet another embodiment, the subject has been treated with PKC 412, MLN 578, CEP-701, CT 53518, CT-53608, CT-52923, D-64406, D-65476, AGL-2033, AG1295, AG1296, KN-1022, PKC-412, SU5416, SU5614, SU11248, L-00021649, or CHIR-258. In still another embodiment, the subject has a constitutively activating FLT3 mutant.

In certain embodiments, the mammal to be treated with one of the methods provided herein has not been treated with anticancer therapy prior to the administration of AC220, or a pharmaceutically acceptable prodrug, salt, hydrate or solvate thereof. In certain embodiments, the mammal to be treated with one of the methods provided herein has been treated with anticancer therapy prior to the administration of AC220, or a pharmaceutically acceptable prodrug, salt, hydrate or solvate thereof.

The methods provided herein encompass treating a subject regardless of patient's age, although some diseases or disorders are more common in certain age groups. Further provided herein is a method for treating a subject who has undergone surgery in an attempt to treat the disease or condition at issue, as well as the one who have not. Because the subjects with cancer have heterogeneous clinical manifestations and varying clinical outcomes, the treatment given to a particular subject may vary, depending on his/her prognosis. The skilled clinician will be able to readily determine without undue experimentation, specific secondary agents, types of surgery, and types of non-drug based standard therapy that can be effectively used to treat an individual subject with cancer.

In another embodiment, provided herein is a method of inhibiting the growth of a cell, comprising contacting the cell with an effective amount of an anthracycline and AC220 or a pharmaceutically acceptable salt, solvate, hydrate, or prodrug thereof. In one embodiment, the anthracycline is daunorubicin. In another embodiment, provided herein is a method of inhibiting the growth of a cell, comprising contacting the cell with an effective amount of a topoisomerase inhibitor and AC220 or a pharmaceutically acceptable salt, solvate, hydrate, or prodrug thereof. In one embodiment, the topoisomerase inhibitor is etoposide. In another embodiment, provided herein is a method of inhibiting the growth of a cell, comprising contacting the cell with an effective amount of a nucleoside analog and AC220 or a pharmaceutically acceptable salt, solvate, hydrate, or prodrug thereof.

In certain embodiments, the cell is a mammalian cell. In certain embodiments, the mammal is a human cell. In certain embodiments, the cell is a tumor cell. In certain embodiments, the cell is mammalian tumor cell. In certain embodiments, the cell is a human tumor cell. In certain embodiments, the cell is a cancerous cell. In certain embodiments, the cell is mammalian cancerous cell. In certain embodiments, the cell is a human cancerous cell. In certain embodiments, the tumor cell expresses the FLT3 ITD mutation. In certain embodiments, the tumor cell overexpresses FLT3 protein.

In certain embodiments, the cancerous cell that can be treated with the methods provided herein includes, but is not limited to, cells of bladder cancer; breast cancer; cervical cancer; colon cancer (e.g., colorectal cancer); endometrial cancer; esophageal cancer; gastric cancer; glioma (e.g., glioblastoma); head and neck cancer; liver cancer, lung cancer (e.g., small cell and non-small cell lung cancers); melanoma; myeloma; neuroblastoma; ovarian cancer; pancreatic cancer; prostate cancer; renal cancer; sarcoma (e.g., osteosarcoma); skin cancer (e.g., squamous cell carcinoma); stomach cancer; testicular cancer; thyroid cancer; uterine cancer; leukemia, including acute myeloid leukemia (AML), acute promyelocytic leukemia, acute myeloblastic leukemia, acute monoblastic leukemia, acute monocytic leukemia, acute erythroid leukemia, acute megakaryoblastic leukemia, acute basophilic leukemia, acute panmyelosis, myeloid sarcoma, chronic myeloid leukemia (CML), acute lymophoblastic leukemia (ALL) and myelodysplastic syndromes (MDS), and lymphoma, including B-cell lymphoma, chronic lymphocytic leukemia, Burkitt's lymphoma, B-cell prolymphocytic leukemia, T-cell lymphoma, T-cell prolymphocytic leukemia, T-cell large granular lymphocytic leukemia, natural killer (NK) cell lymphoma, aggressive natural killer cell leukemia, Hodgkin lymphoma and nonHodgkin lymphoma.

In certain embodiments, the cancerous cell is a cell of bladder cancer, breast cancer, cervical cancer, colon cancer (e.g., colorectal cancer), endometrial cancer, gastric cancer, glioma (e.g., glioblastoma), head and neck cancer, liver cancer, non-small cell lung cancer, ovarian cancer, pancreatic cancer, or prostate cancer.

In certain embodiments, the cell is treated by contacting the cell with AC220 or a pharmaceutically acceptable salt, solvate, hydrate, or prodrug thereof; prior to contacting the cell with the topoisomerase inhibitor or anthracycline. In certain embodiments, the cell is treated by contacting the cell with AC220 or a pharmaceutically acceptable salt, solvate, hydrate, or prodrug thereof; prior to contacting the cell with the nucleoside analog. In certain embodiments, the cell is treated with the compound provided herein, about 2 days, about 1 day, about 12 hrs, about 6 hrs, about 4 hrs, about 2 hrs, about 60 min, about 30 min, or about 10 min before contacting the cell with the nucleoside analog, topoisomerase inhibitor or anthracycline.

In certain embodiments, the cell is treated by contacting the cell with AC220 or a pharmaceutically acceptable salt, solvate, hydrate, or prodrug thereof; concurrently by contacting the cell with an anthracycline. In certain embodiments, the cell is treated by contacting the cell with AC220 or a pharmaceutically acceptable salt, solvate, hydrate, or prodrug thereof; concurrently by contacting the cell with a topoisomerase inhibitor. In certain embodiments, the cell is treated by contacting the cell with AC220 or a pharmaceutically acceptable salt, solvate, hydrate, or prodrug thereof; concurrently by contacting the cell with a nucleoside analog.

In certain embodiments, the cell is treated by contacting the cell with AC220 or a pharmaceutically acceptable salt, solvate, hydrate, or prodrug thereof; after contacting the cell with an anthracycline. In certain embodiments, the cell is treated by contacting the cell with AC220 or a pharmaceutically acceptable salt, solvate, hydrate, or prodrug thereof; after contacting the cell with a nucleoside analog. In certain embodiments, the cell is treated by contacting the cell with AC220 or a pharmaceutically acceptable salt, solvate, hydrate, or prodrug thereof; after contacting the cell with a topoisomerase inhibitor. In certain embodiments, the cell is treated with AC220 provided herein, about 2 days, about 1 day, about 12 hrs, about 6 hrs, about 4 hrs, about 2 hrs, about 60 min, about 30 min, or about 10 min after contacting the cell with the nucleoside analog, topoisomerase inhibitor or anthracycline. In one embodiment, the nucleoside analog is AZA, cytarabine of clofarabine. In one embodiment, the anthracycline is daunorubicin. In one embodiment, the topoisomerase inhibitor is etoposide.

The inhibition of cell growth can be gauged by, e.g., counting the number of cells contacted with compounds of interest, comparing the cell proliferation with otherwise identical cells not contacted with the compounds, or determining the size of the tumor that encompasses the cells. The number of cells, as well as the size of the cells, can be readily assessed using any method known in the art (e.g., trypan blue exclusion and cell counting, measuring incorporation of $^3$H-thymidine into nascent DNA in a cell). Cell viability may also be measured using a fluorometric assay measuring, for example, CellTiter-Blue™.

E. Combination Dosing of AC220 and Second Agents

In certain embodiments, the methods provided herein comprise administering the compound of structural formula (I), or a salt, solvate, ester and/or prodrug thereof, in combination with one or more second active agents for cancer treatment. In one embodiment, the second agent is selected from azacitidine (AZA), cytarabine (Ara-C or AraC), idarubicin, mitoxatrone, clofarabine, cladribine, daunorubicin and etoposide, or a combination thereof. In one embodiment, the second agent is GDC-0941. The second agents provided herein can be administered either prior to, concurrently with, or subsequent to administration of the compound of structural formula (I), or a salt, solvate, ester and/or prodrug thereof. In some embodiments, the second agent can be administered subcutaneously or intravenously. In certain embodiments, the second agent is administered subcutaneously. In certain embodiments, the second agent is administered intravenously.

In certain embodiments, the methods provided herein comprise administering AC220 and/or a pharmaceutically acceptable salt, prodrug, solvate or hydrate thereof in combination with one or more second active agents selected from cytarabine, daunorubicin and etoposide.

In certain embodiments, the methods provided herein comprise administering AC220 and/or a pharmaceutically acceptable salt, prodrug, solvate or hydrate thereof in combination with one or more second active agents selected from daunorubicin and etoposide. In certain embodiments, the methods provided herein comprise administering AC220 and/or a pharmaceutically acceptable salt, prodrug, solvate or hydrate thereof in combination with one or more second active agents selected from cytarabine and daunorubicin.

In certain embodiments, the combination regimen can be administered repetitively if necessary, for example, until the patient experiences stable disease or regression, or until the patient experiences disease progression or unacceptable toxicity. For example, stable disease for solid tumors generally means that the perpendicular diameter of measurable lesions has not increased by 25% or more from the last measurement. Response Evaluation Criteria in Solid Tumors (RECIST) Guidelines, *Journal of the National Cancer Institute* 2000, 92, 205-216. Stable disease or lack thereof is determined by methods known in the art such as evaluation of patient symptoms, physical examination, visualization of the tumor that has been imaged using X-ray, CAT, PET, or MRI scan and other commonly accepted evaluation modalities.

In certain embodiments, the combination regimen is administered to the subject over an extended period of time, ranging from 1 day to about 12 months, from 2 days to about 6 months, from 3 days to about 5 months, from 3 days to about 4 months, from 3 days to about 12 weeks, from 3 days to about 10 weeks, from 3 days to about 8 weeks, from 3 days to about 6 weeks, from 3 days to about 5 weeks, from 3 days to about 4 weeks, from 3 days to about 3 weeks, from 3 days to about 2 weeks, or from 3 days to about 10 days.

In certain embodiments, the combination regimen is administered in a 21 day cycle. In certain embodiments, the combination regimen is administered in a 28 day cycle. In certain embodiments, the combination regimen is administered in a monthly cycle.

In certain embodiments, the combination regimen is cyclically administered to the subject. Cycling therapy involves the administration of the combination regimen provided herein for a period of time, followed by a rest for a period of time, and repeating this sequential administration. Cycling therapy can reduce the development of resistance to one or more of the therapies, avoid or reduce the side effects of one of the therapies, and/or improves the efficacy of the treatment.

Consequently, in one embodiment, the combination regimen provided herein is administered daily for one week, two weeks, three weeks, four weeks, five weeks, six weeks, eight weeks, ten weeks, fifteen weeks, or twenty weeks, followed by a rest period of about 1 day to about ten weeks. For example, the methods contemplate using cycling of one week, two weeks, three weeks, four weeks, five weeks, six weeks, eight weeks, ten weeks, fifteen weeks, or twenty weeks. In another embodiment, the combination regimen provided herein is administered daily for one week, two weeks, three weeks, four weeks, five weeks, or six weeks with a rest period of 1, 3, 5, 7, 9, 12, 14, 16, 18, 20, 22, 24, 26, 28, 29 or 30 days. In certain embodiments, the rest period is 14 days. In certain embodiments, the rest period is 28 days. In one embodiment, the rest period is a period that is sufficient for bone marrow recovery. The frequency, number and length of dosing cycles can be increased or decreased.

As used herein, the term "combination regimen" includes the use of more than one therapies (e.g., one or more prophylactic and/or therapeutic agents). However, the use of the term "combination regimen" does not restrict the order in which therapies (e.g., prophylactic and/or therapeutic agents) are administered to the subject. A first therapy (e.g., AC220) can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy (e.g., a prophylactic or therapeutic agent such as the anthracycline or topoisomerase inhibitor described herein) to the subject. Triple therapy is also contemplated herein (e.g., cytarabine or thioguanine as a third therapy).

In certain embodiments, AC220; or a pharmaceutically acceptable salt, solvate, hydrate, or prodrug thereof; is administered to the subject prior to the administration of a nucleoside analog. In certain embodiments, AC220; or a pharmaceutically acceptable salt, solvate, hydrate, or prodrug thereof is administered to the subject about 7 days, about 5 days, about 3 days, 2 days, about 1 day, about 12 hrs, about 6 hrs, about 4 hrs, about 2 hrs, about 60 min, about 30 min, about 10 min before the administration of a nucleoside analog. In certain embodiments, AC220; or a pharmaceutically acceptable salt, solvate, hydrate, or prodrug thereof is administered to the subject about 2 days before the administration of nucleoside analog. In certain embodiments, AC220; or a pharmaceutically acceptable salt, solvate, hydrate, or prodrug thereof is administered to the subject about 1 day before the administration of a nucleoside analog. In certain embodiments, AC220; or a pharmaceutically acceptable salt, solvate, hydrate, or prodrug thereof is administered to the subject in the same day as the administration of a nucleoside analog.

In certain embodiments, AC220; or a pharmaceutically acceptable salt, solvate, hydrate, or prodrug thereof; is administered to the subject prior to the administration of a topoisomerase inhibitor. In certain embodiments, AC220; or a pharmaceutically acceptable salt, solvate, hydrate, or prodrug thereof is administered to the subject about 7 days, about 5 days, about 3 days, 2 days, about 1 day, about 12 hrs, about 6 hrs, about 4 hrs, about 2 hrs, about 60 min, about 30 min, about 10 min before the administration of a topoisomerase inhibitor. In certain embodiments, AC220; or a pharmaceutically acceptable salt, solvate, hydrate, or prodrug thereof is administered to the subject about 2 days before the administration of a topoisomerase inhibitor. In certain embodiments, AC220; or a pharmaceutically acceptable salt, solvate, hydrate, or prodrug thereof is administered to the subject about 1 day before the administration of a topoisomerase inhibitor. In certain embodiments, AC220; or a pharmaceutically acceptable salt, solvate, hydrate, or prodrug thereof is administered to the subject in the same day as the administration of a topoisomerase inhibitor.

In certain embodiments, AC220; or a pharmaceutically acceptable salt, solvate, hydrate, or prodrug thereof; is administered to the subject prior to the administration of an anthracycline. In certain embodiments, AC220; or a pharmaceutically acceptable salt, solvate, hydrate, or prodrug thereof is administered to the subject about 7 days, about 5 days, about 3 days, about 2 days, about 1 day, about 12 hrs, about 6 hrs, about 4 hrs, about 2 hrs, about 60 min, about 30 min, about 10 min before the administration of an anthracycline. In certain embodiments, AC220; or a pharmaceutically acceptable salt, solvate, hydrate, or prodrug thereof is administered to the subject about 2 days before the administration of an anthracycline. In certain embodiments, AC220; or a pharmaceutically acceptable salt, solvate, hydrate, or prodrug thereof is administered to the subject about 1 day before the administration of an anthracycline.

In certain embodiments, AC220; or a pharmaceutically acceptable salt, solvate, hydrate, or prodrug thereof; is administered to the subject after the administration of a nucleoside analog. In certain embodiments, AC220; or a pharmaceutically acceptable salt, solvate, hydrate, or prodrug thereof is administered to the subject about 7 days, about 5 days, about 3 days, 2 days, about 1 day, about 12 hrs, about 6 hrs, about 4 hrs, about 2 hrs, about 60 min, about 30 min, about 10 min after the administration of a nucleoside analog. In certain embodiments, AC220; or a pharmaceutically acceptable salt, solvate, hydrate, or prodrug thereof is administered to the subject about 2 days after the administration of nucleoside analog. In certain embodiments, AC220; or a pharmaceutically acceptable salt, solvate, hydrate, or prodrug thereof is administered to the subject about 1 day after the administration of a nucleoside analog.

In certain embodiments, AC220; or a pharmaceutically acceptable salt, solvate, hydrate, or prodrug thereof; is administered to the subject after the administration of a topoisomerase inhibitor. In certain embodiments, AC220; or a pharmaceutically acceptable salt, solvate, hydrate, or prodrug thereof is administered to the subject about 7 days, about 5 days, about 3 days, 2 days, about 1 day, about 12 hrs, about 6 hrs, about 4 hrs, about 2 hrs, about 60 min, about 30 min, about 10 min after the administration of a topoisomerase inhibitor. In certain embodiments, AC220; or a pharmaceutically acceptable salt, solvate, hydrate, or prodrug thereof is administered to the subject about 2 days after the administration of a topoisomerase inhibitor. In certain embodiments, AC220; or a pharmaceutically acceptable salt, solvate, hydrate, or prodrug thereof is administered to the subject about 1 day after the administration of a topoisomerase inhibitor.

In certain embodiments, AC220; or a pharmaceutically acceptable salt, solvate, hydrate, or prodrug thereof; is administered to the subject after the administration of an anthracycline. In certain embodiments, AC220; or a pharmaceutically acceptable salt, solvate, hydrate, or prodrug thereof is administered to the subject about 7 days, about 5 days, about 3 days, about 2 days, about 1 day, about 12 hrs, about 6 hrs, about 4 hrs, about 2 hrs, about 60 min, about 30 min, about 10 min after the administration of an anthracycline. In certain embodiments, AC220; or a pharmaceutically acceptable salt, solvate, hydrate, or prodrug thereof is administered to the subject about 2 days after the administration of an anthracycline. In certain embodiments, AC220; or a pharmaceutically acceptable salt, solvate, hydrate, or prodrug thereof is administered to the subject about 1 day after the administration of an anthracycline.

In certain embodiments, AC220 or a pharmaceutically acceptable salt, solvate, hydrate, or prodrug thereof is administered to the subject concurrently with the administration of a nucleoside analog, a topoisomerase inhibitor or an anthracycline.

In each embodiment provided herein, the method may further comprise a diagnostic step for determining the expression level of FLT3 protein on the cells of the tumor. In one embodiment, the diagnostic step is carried out prior to the administration of the combination regimen provided herein. If the subject has a tumor with overexpressed FLT3, the combination regimen provided herein is then administered. In another embodiment, the diagnostic step is carried out during the course of the treatment.

In each embodiment provided herein, the method may further comprise a diagnostic step for determining the expression level of FLT3 protein on the cells of the tumor. In one embodiment, the diagnostic step is carried out prior to the administration of the compounds. In another embodiment, the diagnostic step is carried out during the course of the treatment.

In each embodiment provided herein, the method may further comprise a diagnostic step for measuring the levels of phosphorylated FLT3 protein on the cells of the tumor or blast cells. In one embodiment, the diagnostic step is carried out prior to the administration of the compounds. In another embodiment, the diagnostic step is carried out during the course of the treatment.

In each embodiment provided herein, the method may further comprise a diagnostic step for determining the presence of the FLT3 ITD mutation in the cells of the tumor or blast cells. In one embodiment, the diagnostic step is carried out prior to the administration of the compounds. In another embodiment, the diagnostic step is carried out during the course of the treatment.

The methods provided herein may further comprise administering other therapeutic agents useful in the treatment and/or prevention of a disease described herein.

In certain embodiments, each method provided herein may independently further comprise the step of administering an additional therapeutic agent. The additional therapeutic agents that may be used in combination with the combination regimen herein include, but are not limited to, surgery, endocrine therapy, biologic response modifiers (e.g., interferons, interleukins, and tumor necrosis factor (TNF)), hyperthermia and cryotherapy, agents to attenuate any adverse effects (e.g., antiemetics), and other approved chemotherapeutic drugs, including, but not limited to, anti-metabolites (e.g., 5-fluorouracil, methotrexate, fludarabine), antimicrotubule agents (e.g., vinca alkaloids such as vincristine, vinblastine; taxanes such as paclitaxel, docetaxel), alkylating agents (e.g., cyclophosphamide, melphalan, carmustine, nitrosoureas such as bischloroethylnitrosurea and hydroxyurea), platinum agents (e.g. cisplatin, carboplatin, oxaliplatin, JM-216, CI-973), anthracyclines (e.g., doxrubicin), antitumor antibiotics (e.g., mitomycin, idarubicin, adriamycin, daunorubicin), topoisomerase inhibitors (e.g., etoposide, camptothecins) or any other cytotoxic agents, (estramustine phosphate, prednimustine), hormones or hormone agonists, antagonists, partial agonists or partial antagonists, kinase inhibitors, and radiation treatment. For a more comprehensive discussion of updated cancer therapies; See, http://www.nci.nih.gov/, a list of the FDA approved oncology drugs at http://www.fda.gov/ cder/cancer/druglistframe.htm, and The Merck Manual, Seventeenth Ed. 1999, the entire contents of which are hereby incorporated by reference.

In certain embodiments, the additional therapeutic agents that may be used in combination with the combination regimen herein include, but are not limited to, thioguanine, granulocyte colony stimulating factor (G-CSF), granulocyte-macrophage colony-stimulating factor (GM-CSF), gemtuzumab ozogamicin, vinblastine, gemcitabine, mitomycin, bevacizumab and etoposide.

The combination regimes provided herein can also be provided as an article of manufacture using packaging materials well known to those of skill in the art. See, e.g., U.S. Pat. Nos. 5,323,907; 5,052,558; and 5,033,252. Examples of pharmaceutical packaging materials include, but are not limited to, blister packs, bottles, tubes, inhalers, pumps, bags, vials, containers, syringes, and any packaging material suitable for a selected formulation and intended mode of administration and treatment.

i) Combination of AC220 and AZA

In one embodiment, a compound of formula (I), AC220 or a pharmaceutically acceptable prodrug, salt, solvate or hydrate thereof is orally administered in combination with the subcutaneous or intravenous administration of AZA, using any one of dose levels −3, −2, −1 or 0 selected from one of Tables 1A to 1G below:

TABLE 1A

| | |
|---|---|
| Dose level −3 | 50 mg/m$^2$/day of AZA for 7 days and 135 mg/day of a compound of formula (I) or AC220 for 14 days, in one treatment cycle |
| Dose level −2 | 50 mg/m$^2$/day of AZA for 7 days and 200 mg/day of a compound of formula (I) or AC220 for 14 days, in one treatment cycle |
| Dose level −1 | 75 mg/m$^2$/day of AZA for 7 days and 300 mg/day of a compound of formula (I) or AC220 for 14 days, in one treatment cycle |
| Dose level 0 | 75 mg/m$^2$/day of AZA for 7 days and 450 mg/day of a compound of formula (I) or AC220 for 14 days, in one treatment cycle |

TABLE 1B

| | |
|---|---|
| Dose level −3 | 50 mg/m$^2$/day of AZA for 7 days and 90 mg/day of a compound of formula (I) or AC220 for 14 days, in one treatment cycle |
| Dose level −2 | 50 mg/m$^2$/day of AZA for 7 days and 135 mg/day of a compound of formula (I) or AC220 for 14 days, in one treatment cycle |
| Dose level −1 | 75 mg/m$^2$/day of AZA for 7 days and 200 mg/day of a compound of formula (I) or AC220 for 14 days, in one treatment cycle |
| Dose level 0 | 75 mg/m$^2$/day of AZA for 7 days and 300 mg/day of a compound of formula (I) or AC220 for 14 days, in one treatment cycle |

TABLE 1C

| | |
|---|---|
| Dose level −3 | 50 mg/m$^2$/day of AZA for 7 days and 135 mg/day of a compound of formula (I) or AC220 for 28 days, in one treatment cycle |
| Dose level −2 | 50 mg/m$^2$/day of AZA for 7 days and 200 mg/day of a compound of formula (I) or AC220 for 28 days, in one treatment cycle |
| Dose level −1 | 75 mg/m$^2$/day of AZA for 7 days and 300 mg/day of a compound of formula (I) or AC220 for 28 days, in one treatment cycle |
| Dose level 0 | 75 mg/m$^2$/day of AZA for 7 days and 450 mg/day of a compound of formula (I) or AC220 for 28 days, in one treatment cycle |

TABLE 1D

| | |
|---|---|
| Dose level −3 | 50 mg/m$^2$/day of AZA for 7 days and 90 mg/day of a compound of formula (I) or AC220 for 28 days, in one treatment cycle |
| Dose level −2 | 50 mg/m$^2$/day of AZA for 7 days and 135 mg/day of a compound of formula (I) or AC220 for 28 days, in one treatment cycle |
| Dose level −1 | 75 mg/m$^2$/day of AZA for 7 days and 200 mg/day of a compound of formula (I) or AC220 for 28 days, in one treatment cycle |
| Dose level 0 | 75 mg/m$^2$/day of AZA for 7 days and 300 mg/day of a compound of formula (I) or AC220 for 28 days, in one treatment cycle |

TABLE 1E

| | |
|---|---|
| Dose level −3 | 50 mg/m$^2$/day of AZA for 7 days and 60 mg/day of a compound of formula (I) or AC220 for 28 days, in one treatment cycle |
| Dose level −2 | 50 mg/m$^2$/day of AZA for 7 days and 90 mg/day of a compound of formula (I) or AC220 for 28 days, in one treatment cycle |
| Dose level −1 | 75 mg/m$^2$/day of AZA for 7 days and 135 mg/day of a compound of formula (I) or AC220 for 28 days, in one treatment cycle |
| Dose level 0 | 75 mg/m$^2$/day of AZA for 7 days and 200 mg/day of a compound of formula (I) or AC220 for 28 days, in one treatment cycle |

TABLE 1F

| | |
|---|---|
| Dose level −3 | 50 mg/m$^2$/day of AZA for 7 days and 60 mg/day of a compound of formula (I) or AC220 for 28 days, in one treatment cycle |
| Dose level −2 | 50 mg/m$^2$/day of AZA for 7 days and 90 mg/day of a compound of formula (I) or AC220 for 28 days, in one treatment cycle |
| Dose level −1 | 50 mg/m$^2$/day of AZA for 7 days and 135 mg/day of a compound of formula (I) or AC220 for 28 days, in one treatment cycle |
| Dose level 0 | 50 mg/m$^2$/day of AZA for 7 days and 200 mg/day of a compound of formula (I) or AC220 for 28 days, in one treatment cycle |

TABLE 1G

| | |
|---|---|
| Dose level −3 | 75 mg/m$^2$/day of AZA for 7 days and 60 mg/day of a compound of formula (I) or AC220 for 28 days, in one treatment cycle |
| Dose level −2 | 75 mg/m$^2$/day of AZA for 7 days and 90 mg/day of a compound of formula (I) or AC220 for 28 days, in one treatment cycle |
| Dose level −1 | 75 mg/m$^2$/day of AZA for 7 days and 135 mg/day of a compound of formula (I) or AC220 for 28 days, in one treatment cycle |
| Dose level 0 | 75 mg/m$^2$/day of AZA for 7 days and 200 mg/day of a compound of formula (I) or AC220 for 28 days, in one treatment cycle |

In one embodiment, for one treatment cycle, AZA is administered for 7 consecutive days before the administration of a compound of formula (I) or AC220 for 14 consecutive days. In another embodiment, for one treatment cycle, a compound of formula (I) is administered for 14 consecutive days before the administration of AZA for 7 consecutive days. In yet another embodiment, for one treatment cycle, AZA is administered for the first 7 consecutive days and a compound of formula (I) is administered for the first 14 consecutive days. In another embodiment, for one treatment cycle, AZA is administered for the first 7 consecutive days and a compound of formula (I) is administered for the first 28 consecutive days. In yet another embodiment, for one treatment cycle, a compound of formula (I) is administered for 28 consecutive days and AZA is administered for 7 consecutive days that overlap with a compound of formula (I) administration. In another embodiment, AZA is administered on days 1 through 7 and a compound of formula (I) is administered on days 1 through 14, of a treatment cycle. In another embodiment, AZA is administered on days 1 through 7 and a compound of formula (I) is administered on days 1 through 28, of a treatment cycle. In another embodiment, AZA is administered on days 1 to 7 and a compound of formula (I) is administered on days 8 through 21, of a treatment cycle. In yet another embodiment, a compound of formula (I) is administered on days 1 through 14 and AZA is administered on days 15 through 21, of a treatment cycle. In another embodiment, the treatment cycle is 28 days, 29 days, 30 days or 31 days. In another embodiment, the treatment cycle is any length of time from 4 weeks to 6 weeks long.

In another specific embodiment, for one treatment cycle, the present combination therapy comprises an oral administration of a compound of formula (I) using a regimen selected from the group consisting of:
- A. 60 mg/day of a compound of formula (I) or AC220 on days 1 to 14,
- B. 60 mg/day of a compound of formula (I) or AC220 on days 1 to 28,
- C. 90 mg/day of a compound of formula (I) or AC220 on days 1 to 14,
- D. 90 mg/day of a compound of formula (I) or AC220 on days 1 to 28,
- E. 135 mg/day of a compound of formula (I) or AC220 on days 1 to 14,
- F. 135 mg/day of a compound of formula (I) or AC220 on days 1 to 28,
- G. 200 mg/day of a compound of formula (I) or AC220 on days 1 to 14,
- H. 200 mg/day of a compound of formula (I) or AC220 on days 1 to 28,
- I. 300 mg/day of a compound of formula (I) or AC220 on days 1 to 14,
- J. 300 mg/day of a compound of formula (I) or AC220 on days 1 to 28,
- K. 450 mg/day of a compound of formula (I) or AC220 on days 1 to 14, and
- L. 450 mg/day of a compound of formula (I) or AC220 on days 1 to 28;

and a subcutaneous or intravenous administration of AZA using a regimen selected from the group consisting of:
- I. 100 mg/m$^2$/day for 5 days,
- II. 100 mg/m$^2$/day on days 1 to 5,
- III. 75 mg/m$^2$/day for 7 days,
- IV. 75 mg/m$^2$/day on days 1 to 7,
- V. 75 mg/m$^2$/day for 5 days,
- VI. 75 mg/m$^2$/day on days 1 to 5,
- VII. 75 mg/m$^2$/day for 5 days followed by 2 days rest, then followed by 2 additional days,
- VIII. 75 mg/m$^2$/day on days 1 to 5 followed by rest on days 6 and 7 followed by 75 mg/m$^2$/day on days 8 and 9,
- IX. 50 mg/m$^2$/day for 7 days,
- X. 50 mg/m$^2$/day on days 1 to 7,
- XI. 50 mg/m$^2$/day qod (every other day) for the first 14 days,
- XII. 50 mg/m$^2$/day on days 1, 3, 5, 7, 9, 11 and 13,
- XIII. 50 mg/m$^2$/day for 5 days,
- XIV. 50 mg/m$^2$/day on days 1 to 5,
- XV. 50 mg/m$^2$/day for 5 days followed by 2 days of rest, then followed by 5 additional days of 50 mg/m$^2$/day,
- XVI. 50 mg/m$^2$/day on days 1 to 5 followed by rest on days 6 and 7 followed by 50 mg/m$^2$/day on days 8-13,
- XVII. 50 mg/m$^2$/day for 5 days followed by 2 days of rest, then followed by 4 additional days of 50 mg/m$^2$/day,
- XVIII. 50 mg/m$^2$/day on days 1 to 5 followed by rest on days 6 and 7 followed by 50 mg/m$^2$/day on days 8-12,
- XIX. 37.5 mg/m$^2$/day for 7 days,
- XX. 37.5 mg/m$^2$/day on days 1 to 7,
- XXI. 8 mg/m$^2$/day for 5 days,
- XXII. 8 mg/m$^2$/day on days 1 to 5,
- XXIII. 75 mg/m$^2$/day for 5 days,
- XXIV. 75 mg/m$^2$/day for the first 5 consecutive days, wherein the combination regimen is administered simultaneously, concurrently, separately or sequentially.

In another specific embodiment, the combination regimen comprises an oral administration of a compound of formula (I) or AC220 using a regimen selected from the group consisting of:
- A. 60 mg/day of a compound of formula (I) or AC220 on days 1 to 14,
- B. 60 mg/day of a compound of formula (I) or AC220 on days 1 to 28,
- C. 90 mg/day of a compound of formula (I) or AC220 on days 1 to 14,
- D. 90 mg/day of a compound of formula (I) or AC220 on days 1 to 28,
- E. 135 mg/day of a compound of formula (I) or AC220 on days 1 to 14,
- F. 135 mg/day of a compound of formula (I) or AC220 on days 1 to 28,
- G. 200 mg/day of a compound of formula (I) or AC220 on days 1 to 14,
- H. 200 mg/day of a compound of formula (I) or AC220 on days 1 to 28,
- I. 300 mg/day of a compound of formula (I) or AC220 on days 1 to 14,
- J. 300 mg/day of a compound of formula (I) or AC220 on days 1 to 28,
- K. 450 mg/day of a compound of formula (I) or AC220 on days 1 to 14, and
- L. 450 mg/day of a compound of formula (I) or AC220 on days 1 to 28;

and an oral administration of AZA using a regimen selected from the group consisting of:
- aa. A dose calculated to deliver 100% of the subcutaneous exposure (AUC) on days 1 to 7,
- bb. 100 mg on days 1 to 7,
- cc. 120 mg on days 1 to 7,
- dd. 180 mg on days 1 to 7,
- ee. 240 mg on days 1 to 7,
- ff. 200 mg on days 1 to 7,
- gg. 300 mg on days 1 to 7,
- hh. 360 mg on days 1 to 7,
- ii. 420 mg on days 1 to 7,
- jj. 480 mg on days 1 to 7,
- kk. 540 mg on days 1 to 7,
- ll. 600 mg on days 1 to 7,
- mm. 660 mg on days 1 to 7,
- nn. 720 mg on days 1 to 7,
- oo. 780 mg on days 1 to 7,
- pp. 840 mg on days 1 to 7,
- qq. 900 mg on days 1 to 7,
- rr. 960 mg on days 1 to 7,
- ss. 1000 mg on days 1 to 7,
- tt. 1020 mg on days 1 to 7,
- uu. 1080 mg on days 1 to 7,
- vv. 1140 mg on days 1 to 7, and ww. 1200 mg on days 1 to 7;
wherein the combination regimen is administered simultaneously, concurrently, separately or sequentially.

In one embodiment, for one treatment cycle, AC220 is orally administered for 14 days, and AZA is administered subcutaneously or intravenously daily at 50 mg/m² or 75 mg/m², for the first 7 days.

ii) Combination of AC220 and Cytarabine

In another embodiment of the present method, the compound of structural formula (I) as described above, or a salt, solvate, ester and/or prodrug thereof comprises AC220, or a salt, solvate, ester and/or prodrug thereof; and the nucleoside analog comprises cytarabine.

In one embodiment, for one treatment cycle, the combination regimen comprises an oral administration of a compound of formula (I) or AC220 using a regimen selected from the group consisting of:
- A. 12 mg/day of a compound of formula (I) or AC220 for 14-32 days,
- B. 20 mg/day of a compound of formula (I) or AC220 for 14-32 days,
- C. 25 mg/day of a compound of formula (I) or AC220 for 14-32 days,
- D. 50 mg/day of a compound of formula (I) or AC220 for 14-32 days,
- E. 60 mg/day of a compound of formula (I) or AC220 for 14-32 days,
- F. 75 mg/day of a compound of formula (I) or AC220 for 14-32 days,
- G. 90 mg/day of a compound of formula (I) or AC220 for 14-32 days,
- H. 100 mg/day of a compound of formula (I) or AC220 for 14-32 days,
- I. 125 mg/day of a compound of formula (I) or AC220 for 14-32 days,
- J. 135 mg/day of a compound of formula (I) or AC220 for 14-32 days,
- K. 200 mg/day of a compound of formula (I) or AC220 for 14-32 days,
- L. 225 mg/day of a compound of formula (I) or AC220 for 14-32 days,
- M. 250 mg/day of a compound of formula (I) or AC220 for 14-32 days,
- N. 300 mg/day of a compound of formula (I) or AC220 for 14-32 days, and an intravenous or subcutaneous administration of cytarabine regimen selected from the group consisting of:
- i. 5 mg/m²/day of cytarabine for 7-25 days,
- ii. 5 mg/m²/day of cytarabine for 10-14 days,
- iii. 10 mg/m²/day of cytarabine for 7-14 days,
- iv. 10 mg/m²/day of cytarabine for 7 days,
- v. 10 mg/m²/day of cytarabine for 10 days,
- vi. 20 mg/m²/day of cytarabine for 7-25 days,
- vii. 20 mg/m²/day of cytarabine for 10-14 days,
- viii. 20 mg/m²/day of cytarabine for 10 days,
- ix. 20 mg/m²/day of cytarabine for 14 days,
- x. 20 mg/m²/day of cytarabine for 21 days,
- xi. 5-30 mg/m²/day of cytarabine for 1-4 weeks,
- xii. 100 mg/m²/day of cytarabine for 7 days,
- xiii. 150 mg/m²/day of cytarabine for 7 days,
- xiv. 200 mg/m²/day of cytarabine for 7 days,
- xv. 100-200 mg/m²/day of cytarabine for 7 days,
- xvi. 1 g/m²/day of cytarabine for 7 days,
- xvii. 1 g/m²/day of cytarabine for 5 days,
- xviii. 1 g/m²/day of cytarabine for 4 days,
- xix. 1 g/m²/day of cytarabine for 3 days,
- xx. 1 g/m²/day of cytarabine for 7 days,
- xxi. 1.5 g/m²/day of cytarabine for 4 days,
- xxii. 1.5 g/m²/day of cytarabine for 3 days,
- xxiii. 2 g/m²/day of cytarabine for 3 days,
- xxiv. 2 g/m²/day of cytarabine for 4 days,
- xxv. 2 g/m²/day of cytarabine for 5 days,
- xxvi. 2 g/m²/day of cytarabine for 6 days,
- xxvii. 2 g/m²/day of cytarabine for 12 doses every 12 hours,
- xxviii. 4 g/m²/day of cytarabine for 6 days,
- xxix. 3 g/m²/day of cytarabine for 3 days,
- xxx. 3 g/m²/day of cytarabine for 4 days,
- xxxi. 3 g/m²/day of cytarabine for 5 days,
- xxxii. 3 g/m²/day of cytarabine for 6 days,
- xxxiii. 3 g/m² of cytarabine for 12 doses every 12 hours,
- xxxiv. 3 g/m² of cytarabine for 8 doses every 12 hours,
- xxxv. 3 g/m²/day of cytarabine for 6 doses every 12 hours,
- xxxvi. 3 g/m² of cytarabine every 12 hours for days 1, 3 and 5,
- xxxvii. 3 g/m²/day of cytarabine for 12 doses every 12 hours,
- xxxviii. 1 g/m² of cytarabine every 12 hours for days 1, 3 and 5,
- xxxix. 6 g/m²/day of cytarabine for 6 days,
- xl. 20 mg/day of cytarabine for 10 days, and
- xli. 40 mg/day of cytarabine for 10 days, wherein the combination regimen is administered simultaneously, concurrently, separately or sequentially.

In one embodiment, for one treatment cycle, the combination regimen comprises an oral administration of a compound of formula (I) or AC220 using a regimen selected from the group consisting of:
- A. 60 mg/day of a compound of formula (I) or AC220 for 14 days,
- B. 60 mg/day of a compound of formula (I) or AC220 for 28 days,
- C. 60 mg/day of a compound of formula (I) or AC220 for 14-32 days,
- D. 90 mg/day of a compound of formula (I) or AC220 for 14 days,
- E. 90 mg/day of a compound of formula (I) or AC220 for 28 days,
- F. 90 mg/day of a compound of formula (I) or AC220 for 14-32 days,
- G. 135 mg/day of a compound of formula (I) or AC220 for 14 days,
- H. 135 mg/day of a compound of formula (I) or AC220 for 28 days,
- I. 135 mg/day of a compound of formula (I) or AC220 for 14-32 days,
- J. 200 mg/day of a compound of formula (I) or AC220 for 14 days,
- K. 200 mg/day of a compound of formula (I) or AC220 for 28 days,
- L. 200 mg/day of a compound of formula (I) or AC220 for 14-32 days,
- M. 300 mg/day of a compound of formula (I) or AC220 for 14 days,
- N. 300 mg/day of a compound of formula (I) or AC220 for 28 days,
- O. 300 mg/day of a compound of formula (I) or AC220 for 14-32 days,
- P. 450 mg/day of a compound of formula (I) or AC220 for 14 days,
- Q. 450 mg/day of a compound of formula (I) or AC220 for 28 days; and
- R. 450 mg/day of a compound of formula (I) or AC220 for 14-32 days, and an intravenous or subcutaneous administration of cytarabine regimen selected from the group consisting of:
- xlii. 5 mg/m²/day of cytarabine for 7-25 days,
- xliii. 5 mg/m²/day of cytarabine for 10-14 days,
- xliv. 10 mg/m²/day of cytarabine for 7-14 days,
- xlv. 10 mg/m²/day of cytarabine for 7 days,
- xlvi. 10 mg/m²/day of cytarabine for 10 days,
- xlvii. 20 mg/m²/day of cytarabine for 7-25 days,
- xlviii. 20 mg/m²/day of cytarabine for 10-14 days,
- xlix. 20 mg/m²/day of cytarabine for 10 days,
- l. 20 mg/m²/day of cytarabine for 14 days,
- li. 20 mg/m²/day of cytarabine for 21 days,
- lii. 5-30 mg/m²/day of cytarabine for 1-4 weeks,
- liii. 100 mg/m²/day of cytarabine for 7 days,
- liv. 150 mg/m²/day of cytarabine for 7 days,
- lv. 200 mg/m²/day of cytarabine for 7 days,
- lvi. 100-200 mg/m²/day of cytarabine for 7 days,
- lvii. 1 g/m²/day of cytarabine for 7 days,
- lviii. 1 g/m²/day of cytarabine for 5 days,
- lix. 1 g/m²/day of cytarabine for 4 days,
- lx. 1 g/m²/day of cytarabine for 3 days,
- lxi. 1 g/m²/day of cytarabine for 7 days,
- lxii. 1.5 g/m²/day of cytarabine for 4 days,
- lxiii. 1.5 g/m²/day of cytarabine for 3 days,
- lxiv. 2 g/m²/day of cytarabine for 3 days,
- lxv. 2 g/m²/day of cytarabine for 4 days,
- lxvi. 2 g/m²/day of cytarabine for 5 days,
- lxvii. 2 g/m²/day of cytarabine for 6 days,
- lxviii. 2 g/m²/day of cytarabine for 12 doses every 12 hours,
- lxix. 4 g/m²/day of cytarabine for 6 days,
- lxx. 3 g/m²/day of cytarabine for 3 days,
- lxxi. 3 g/m²/day of cytarabine for 4 days,
- lxxii. 3 g/m²/day of cytarabine for 5 days,
- lxxiii. 3 g/m²/day of cytarabine for 6 days,
- lxxiv. 3 g/m² of cytarabine for 12 doses every 12 hours,
- lxxv. 3 g/m² of cytarabine for 8 doses every 12 hours,
- lxxvi. 3 g/m²/day of cytarabine for 6 doses every 12 hours,
- lxxvii. 3 g/m² of cytarabine every 12 hours for days 1, 3 and 5,
- lxxviii. 3 g/m²/day of cytarabine for 12 doses every 12 hours,
- lxxix. 1 g/m² of cytarabine every 12 hours for days 1, 3 and 5,
- lxxx. 6 g/m²/day of cytarabine for 6 days,
- lxxxi. 20 mg/day of cytarabine for 10 days, and
- lxxxii. 40 mg/day of cytarabine for 10 days, wherein the combination regimen is administered simultaneously, concurrently, separately or sequentially.

In another embodiment, the combination regimen further comprises an intravenous administration of an anthracycline using a regimen selected from the following group:
- ia: 45 mg/m²/day of daunorubicin for 3 days,
- ib: 50 mg/m²/day of daunorubicin for 3 days,
- ic: 60 mg/m²/day of daunorubicin for 3 days,
- id: 45-60 mg/m²/day of daunorubicin for 3 days,
- ie: 70 mg/m²/day of daunorubicin for 3 days,
- if: 12 mg/m²/day of idarubicin for 3 days,
- ig: 8 mg/m²/day of idarubicin for 2 days, and
- ig: 12 mg/m²/day of mitoxantrone for 3 days;

wherein the combination regimen is administered simultaneously, concurrently, separately or sequentially.

In another embodiment, the combination regimen of a compound of formula (I) or AC220 and cytarabine further comprises an intravenous administration of etoposide using a regimen selected from the following group:
- i. 50-100 mg/m²/day of etoposide for five days;
- ii. 50-100 mg/m²/day etoposide for days 1 through 5;
- iii. 5-100 mg/m²/day etoposide for three days;
- iv. 5-100 mg/m²/day etoposide for three days;
- v. 50-100 mg/m²/day etoposide for days 1 through 5;
- vi. 35 mg/m²/day for etoposide four days;
- vii. 40 mg/m²/day for etoposide four days;
- viii. 45 mg/m²/day for etoposide four days;
- ix. 50 mg/m²/day for etoposide four days;
- x. 35 mg/m²/day for etoposide four days;
- xi. 40 mg/m²/day for etoposide four days;
- xii. 45 mg/m²/day for etoposide four days; and
- xiii. 50 mg/m²/day for etoposide four days;

wherein the combination regimen is administered simultaneously, concurrently, separately or sequentially. In another embodiment, the combination regimen of a compound of formula (I) or AC220 and cytarabine further comprises an intravenous administration of etoposide using a regimen selected from the following group:
- i. 50-150 mg/m²/day of etoposide for five days;
- ii. 50-150 mg/m²/day etoposide for days 1 through 5; and
- iii. 150 mg/m²/day of etoposide for five days;

wherein the combination regimen is administered simultaneously, concurrently, separately or sequentially.

In one embodiment, cytarabine is administered daily by 24-hour continuous infusion. In another embodiment, cytarabine is administered every 12 hours by intravenous infusion over 1 to 2 hours. In another embodiment, cytarabine is administered twice daily subcutaneously. In another embodiment, in one treatment cycle, cytarabine is administered every other day for a total of 3 days of administration. In another embodiment, in one treatment cycle, cytarabine is administered every other day for a total of 4 days of administration. In another embodiment, in one treatment cycle, cytarabine is administered on days 1, 3 and 5. In yet another embodiment, in one treatment cycle, cytarabine is administered on days 1, 3, 5 and 7.

In one embodiment, in one treatment cycle, cytarabine is administered for the first 7 consecutive days, an anthracycline is administered for 3 consecutive days overlapping with cytarabine administration and a compound of formula (I) or AC220 is administered for 14 consecutive days following the completion of the administration of cytarabine and the anthracycline. In another embodiment, in one treatment cycle, cytarabine is administered for the first 7 consecutive days, an anthracycline is administered for 3 consecutive days overlapping with cytarabine administration and a compound of formula (I) or AC220 is administered for 14 consecutive days, one week after the completion of the administration of cytarabine and the anthracycline. In another embodiment, in one treatment cycle, cytarabine is administered for the first 7 consecutive days, an anthracycline is administered for 3 consecutive days overlapping with cytarabine administration and a compound of formula (I) or AC220 is administered for 14 consecutive days, two weeks after the completion of the administration of cytarabine and the anthracycline. In another embodiment, in one treatment cycle, a compound of formula (I) or AC220 is administered for the first 14 consecutive days, cytarabine is administered for 7 consecutive days following the completion of a compound of formula (I) or AC220 administration and an anthracycline is administered for 3 days overlapping with cytarabine administration. In another embodiment, in one treatment cycle, a compound of formula (I) or AC220 is administered for the first 28 consecutive days, cytarabine is administered for 7 consecutive days following completion of 14 days of administration of a compound of formula (I) or AC220 administration and an anthracycline is administered for 3 days overlapping with cytarabine administration.

In another embodiment, in one treatment cycle, cytarabine is administered for the first 7 consecutive days, an anthracycline is administered for 3 consecutive days overlapping with cytarabine administration and a compound of formula (I) or AC220 is administered for the first 28 consecutive days. In another embodiment, in one treatment cycle, cytarabine is administered for the first 7 consecutive days, an anthracycline is administered for 3 consecutive days overlapping with cytarabine administration and a compound of formula (I) or AC220 is administered for the first 14 consecutive days. In another embodiment, in one treatment cycle, cytarabine is administered on days 1 through 7 and an anthracycline is administered on days 1 through 3 and a compound of formula (I) or AC220 is administered on days 1 through 14. In another embodiment, in one treatment cycle, cytarabine is administered on days 1 through 7 and an anthracycline is administered on days 1 through 3 and a compound of formula (I) or AC220 is administered on days 1 through 28. In one embodiment, in one treatment cycle, cytarabine is administered on days 1 through 7 and an anthracycline is administered on days 1 through 3 and a compound of formula (I) or AC220 is administered on days 4 through 17. In one embodiment, in one treatment cycle, cytarabine is administered on days 1 through 7 and an anthracycline is administered on days 1 through 3 and a compound of formula (I) or AC220 is administered on days 4 through 21. In another embodiment, in one treatment cycle, cytarabine is administered on days 1 through 7 and an anthracycline is administered on days 1 through 3 and a compound of formula (I) or AC220 is administered on days 4 through 28. In one embodiment, in one treatment cycle, cytarabine is administered on days 1 through 7 and an anthracycline is administered on days 1 through 3 and a compound of formula (I) or AC220 is administered on days 4 through 28. In one embodiment, in one treatment cycle, cytarabine is administered on days 1 through 7 and an anthracycline is administered on days 1 through 3 and a compound of formula (I) or AC220 is administered on days 4 through 35. In one embodiment, in one treatment cycle, cytarabine is administered on days 1, 3, and 5, and a compound of formula (I) or AC220 is administered on days 6 through 28.

In another embodiment, in one treatment cycle, cytarabine is administered on days 1 through 7 and an anthracycline is administered on days 1 through 3 and a compound of formula (I) or AC220 is administered on days 8 through 21. In another embodiment, cytarabine is administered on days 1 through 7 and an anthracycline is administered on days 1 through 3 and a compound of formula (I) or AC220 is administered on days 1 through 7 and 15 through 21. In one embodiment, the cytarabine is administered intravenously at 100 mg/m$^2$/day or 200 mg/m$^2$/day. In one embodiment, the anthracycline is daunorubicin. In another embodiment, the daunorubicin is administered intravenously at 60 mg/m$^2$/day. In yet another embodiment, a compound of formula (I) or AC220 is orally administered at dose of 12 mg/m$^2$/day, 20 mg/m$^2$/day, 25 mg/m$^2$/day, 40 mg/m$^2$/day, 50 mg/m$^2$/day, 60 mg/m$^2$/day, 75 mg/m$^2$/day, 90 mg/m$^2$/day, 100 mg/m$^2$/day, 125 mg/m$^2$/day, 135 mg/m$^2$/day, 150 mg/m$^2$/day, or 200 mg/m$^2$/day.

In another embodiment, for one treatment cycle, a compound of formula (I) or AC220 is orally administered at 60 mg/day on days 1 through 14 and cytarabine is administered intravenously at 100 mg/m$^2$/day on days 1 through 7 and daunorubicin is administered intravenously at 60 mg/m$^2$/day on days 1 through 3. In another embodiment, for one treatment cycle, a compound of formula (I) is orally administered at 60 mg/day on days 1 through 28 and cytarabine is administered intravenously at 100 mg/m$^2$/day on days 1 through 7 and daunorubicin is administered intravenously at 60 mg/m$^2$/day on days 1 through 3. In yet another embodiment, for one treatment cycle, a compound of formula (I) is orally administered at 60 mg/day on days 1 through 7 and days 15 through 21 and cytarabine is administered intravenously at 100 mg/m$^2$/day on days 1 through 7 and daunorubicin is administered intravenously at 60 mg/m$^2$/day on days 1 through 3. In another embodiment, for one treatment cycle, a compound of formula (I) or AC220 is orally administered at 60 mg/day on days 4 through 28 and cytarabine is administered intravenously at 100 mg/m$^2$/day on days 1 through 7 and daunorubicin is administered intravenously at 60 mg/m$^2$/day on days 1 through 3. In another embodiment, for one treatment cycle, a compound of formula (I) or AC220 is orally administered at 60 mg/day on days 8 through 21 and cytarabine is administered intravenously at 100 mg/m$^2$/day on days 1 through 7 and daunorubicin is administered intravenously at 60 mg/m$^2$/day on days 1 through 3. In another embodiment, for one treatment cycle, a compound of formula (I) or AC220 is orally administered at 60 mg/day on days 4 through 35 and cytarabine is administered intravenously at 100 mg/m$^2$/day on days 1 through 7 and daunorubicin is administered intravenously at 60 mg/m$^2$/day on days 1 through 3.

In another embodiment, for one treatment cycle, a compound of formula (I) or AC220 is orally administered at 90 mg/day on days 1 through 14 and cytarabine is administered intravenously at 100 mg/m$^2$/day on days 1 through 7 and daunorubicin is administered intravenously at 60 mg/m$^2$/day on days 1 through 3. In another embodiment, for one treatment cycle, a compound of formula (I) or AC220 is orally administered at 90 mg/day on days 1 through 28 and cytarabine is administered intravenously at 100 mg/m$^2$/day on days 1 through 7 and daunorubicin is administered intravenously at 60 mg/m$^2$/day on days 1 through 3. In yet another embodiment, for one treatment cycle, a compound of formula (I) or AC220 is orally administered at 90 mg/day on days 1 through 7 and days 15 through 21 and cytarabine is administered intravenously at 100 mg/m$^2$/day on days 1 through 7 and daunorubicin is administered intravenously at 60 mg/m$^2$/day on days 1 through 3. In one embodiment, for one treatment cycle, cytarabine is administered intravenously at 100 mg/m$^2$/day on days 1 through 7 and daunorubicin is administered intravenously at 60 mg/m$^2$/day on days 1 through 3 and a compound of formula (I) or AC220 is orally administered at 90 mg/day on days 4 through 35.

In another embodiment, for one treatment cycle, a compound of formula (I) or AC220 is orally administered at 135 mg/day on days 1 through 14 and cytarabine is administered intravenously at 100 mg/m$^2$/day on days 1 through 7 and daunorubicin is administered intravenously at 60 mg/m$^2$/day on days 1 through 3. In another embodiment, for one treatment cycle, a compound of formula (I) or AC220 is orally administered at 135 mg/day on days 1 through 28 and cytarabine is administered intravenously at 100 mg/m$^2$/day on days 1 through 7 and daunorubicin is administered intravenously at 60 mg/m$^2$/day on days 1 through 3. In yet another embodiment, for one treatment cycle, a compound of formula (I) or AC220 is orally administered at 135 mg/day on days 1 through 7 and days 15 through 21 and cytarabine is administered intravenously at 100 mg/m$^2$/day on days 1 through 7 and daunorubicin is administered intravenously at 60 mg/m$^2$/day on days 1 through 3. In one embodiment, for one treatment cycle, cytarabine is administered intravenously at 100 mg/m$^2$/day on days 1 through 7 and daunorubicin is administered intravenously at 60 mg/m$^2$/day on days 1 through 3 and a compound of formula (I) or AC220 is orally administered at 135 mg/day on days 4 through 35.

In another embodiment, for one treatment cycle, a compound of formula (I) or AC220 is orally administered at 200 mg/day on days 1 through 14 and cytarabine is administered intravenously at 100 mg/m²/day on days 1 through 7 and daunorubicin is administered intravenously at 60 mg/m²/day on days 1 through 3. In another embodiment, for one treatment cycle, a compound of formula (I) or AC220 is orally administered at 200 mg/day on days 1 through 28 and cytarabine is administered intravenously at 100 mg/m²/day on days 1 through 7 and daunorubicin is administered intravenously at 60 mg/m²/day on days 1 through 3. In yet another embodiment, for one treatment cycle, a compound of formula (I) or AC220 is orally administered at 200 mg/day on days 1 through 7 and days 15 through 21 and cytarabine is administered intravenously at 100 mg/m²/day on days 1 through 7 and daunorubicin is administered intravenously at 60 mg/m²/day on days 1 through 3. In one embodiment, for one treatment cycle, cytarabine is administered intravenously at 100 mg/m²/day on days 1 through 7 and daunorubicin is administered intravenously at 60 mg/m²/day on days 1 through 3 and a compound of formula (I) or AC220 is orally administered at 200 mg/day on days 4 through 35.

In one embodiment, for one treatment cycle, cytarabine is administered intravenously at 100 mg/m²/day on days 1 through 7 and daunorubicin is administered intravenously at 60 mg/m²/day on days 1 through 3 and a compound of formula (I) or AC220 is orally administered at 200 mg/day on days 8 through 21.

In one embodiment, for one treatment cycle, cytarabine is administered intravenously at 100 mg/m²/day on days 1 through 7 and daunorubicin is administered intravenously at 60 mg/m²/day on days 1 through 3 and AC220 is orally administered at 200 mg/day on days 4 through 28.

In one embodiment, for one treatment cycle, cytarabine is administered intravenously at 200 mg/m²/day on days 1 through 7 and daunorubicin is administered intravenously at 60 mg/m²/day on days 1 through 3 and a compound of formula (I) or AC220 is orally administered at 200 mg/day for about 14 up to about 32 days. In one embodiment, a compound of formula (I) or AC220 is orally administered at 200 mg/day on days 4 through 21. In one embodiment, a compound of formula (I) or AC220 is orally administered at 200 mg/day on days 4 through 28. In another embodiment, a compound of formula (I) or AC220 is orally administered at 200 mg/day on days 4 through 35. In another embodiment, a compound of formula (I) or AC220 is orally administered at 200 mg/day on days 8 through 21. In another embodiment, a compound of formula (I) or AC220 is orally administered at 200 mg/day on days 8 through 22.

In one embodiment, for one treatment cycle, cytarabine is administered intravenously at 200 mg/m²/day on days 1 through 7 and daunorubicin is administered intravenously at 60 mg/m²/day on days 1 through 3 and a compound of formula (I) or AC220 is orally administered at 135 mg/day for about 14 up to about 32 days. In one embodiment, a compound of formula (I) or AC220 is orally administered at 135 mg/day on days 4 through 21. In one embodiment, a compound of formula (I) or AC220 is orally administered at 135 mg/day on days 4 through 28. In another embodiment, a compound of formula (I) or AC220 is orally administered at 200 mg/day on days 4 through 35. In another embodiment, a compound of formula (I) or AC220 is orally administered at 135 mg/day on days 8 through 21. In another embodiment, a compound of formula (I) or AC220 is orally administered at 135 mg/day on days 8 through 22.

In one embodiment, for one treatment cycle, cytarabine is administered intravenously at 200 mg/m²/day on days 1 through 7 and daunorubicin is administered intravenously at 60 mg/m²/day on days 1 through 3 and a compound of formula (I) or AC220 is orally administered at 90 mg/day for about 14 up to about 32 days. In one embodiment, a compound of formula (I) or AC220 is orally administered at 90 mg/day on days 4 through 21. In one embodiment, a compound of formula (I) or AC220 is orally administered at 90 mg/day on days 4 through 28. In another embodiment, a compound of formula (I) or AC220 is orally administered at 90 mg/day on days 4 through 35. In another embodiment, a compound of formula (I) or AC220 is orally administered at 90 mg/day on days 8 through 21. In another embodiment, a compound of formula (I) or AC220 is orally administered at 90 mg/day on days 8 through 22.

In one embodiment, for one treatment cycle, cytarabine is administered intravenously at 200 mg/m²/day on days 1 through 7 and daunorubicin is administered intravenously at 60 mg/m²/day on days 1 through 3 and a compound of formula (I) or AC220 is orally administered at 60 mg/day for about 14 up to about 32 days. In one embodiment, a compound of formula (I) or AC220 is orally administered at 60 mg/day on days 4 through 21. In one embodiment, a compound of formula (I) or AC220 is orally administered at 60 mg/day on days 4 through 28. In another embodiment, a compound of formula (I) or AC220 is orally administered at 60 mg/day on days 4 through 35. In another embodiment, a compound of formula (I) or AC220 is orally administered at 60 mg/day on days 8 through 21. In another embodiment, a compound of formula (I) or AC220 is orally administered at 60 mg/day on days 8 through 22.

In one embodiment, AC220 is administered at a dose of 60 mg/m²/day, 90 mg/m²/day, 135 mg/m²/day, or 200 mg/m²/day.

In one embodiment, for one treatment cycle, cytarabine is administered intravenously at 3 g/m² over 3 hours for every 12 hours on days 1, 3 and 5, and a compound of formula (I) or AC220 is orally administered from about 14 days to about 32 days. In one embodiment, AC220 is administered on days 1 through 14. In one embodiment, AC220 is administered on days 1 through 28. In one embodiment, AC220 is administered on days 4 through 17. In one embodiment, AC220 is administered on days 4 through 21. In one embodiment, AC220 is administered on days 4 through 31. In one embodiment, AC220 is administered on days 4 through 35. In one embodiment, AC220 is administered on days 6 through 28. In one embodiment, AC220 is administered on days 6 through 33. In one embodiment, AC220 is administered on days 8 through 21. In one embodiment, for one treatment cycle, cytarabine is administered intravenously at 3 g/m² over 3 hours for every 12 hours on days 1, 3 and 5, and a compound of formula (I) or AC220 is orally administered on days 8 through 21. In one embodiment, AC220 is administered at a dose of 60 mg/m²/day, 90 mg/m²/day, 135 mg/m²/day, or 200 mg/m²/day. In one embodiment, AC220 is administered at a dose of 12 mg/m²/day, 20 mg/m²/day, 25 mg/m²/day, 40 mg/m²/day, 50 mg/m²/day, 60 mg/m²/day, 75 mg/m²/day, 90 mg/m²/day, 100 mg/m²/day, 125 mg/m²/day, 135 mg/m²/day, 150 mg/m²/day, or 200 mg/m²/day.

In one embodiment, for one treatment cycle, cytarabine is administered intravenously at 3 g/m² for every 12 hours on days 1, 3 and 5, and AC220 is orally administered at 200 mg/day on days 6 through 28.

In one embodiment, for one treatment cycle, cytarabine is administered intravenously at 1 g/m² for every 12 hours on days 1, 3 and 5, and AC220 is orally administered at 200 mg/day on days 6 through 28.

In one embodiment, for one treatment cycle, cytarabine is administered intravenously at 3 g/m²/day for 3 or 4 days and a compound of formula (I) or AC220 is orally administered at 90 mg/day for about 14 up to about 32 days. In one embodiment, the compound of formula (I) or AC220 is orally administered at 90 mg/day on days 4 through 28. In another embodiment, the compound of formula (I) or AC220 is orally administered at 90 mg/day on days 6 through 28. In another embodiment, the cytarabine is administered on days 1, 3 and 5. In another embodiment, the cytarabine is administered on days 1, 3, 5 and 7.

In one embodiment, for one treatment cycle, cytarabine is administered intravenously at 3 g/m$^2$/day for 3 or 4 days and a compound of formula (I) or AC220 is orally administered at 135 mg/day for about 14 up to about 32 days. In one embodiment, the compound of formula (I) or AC220 is orally administered at 135 mg/day on days 4 through 28. In another embodiment, the compound of formula (I) or AC220 is orally administered at 135 mg/day on days 6 through 28. In another embodiment, the cytarabine is administered on days 1, 3 and 5.

In another embodiment, the cytarabine is administered on days 1, 3, 5 and 7. In one specific embodiment, for one treatment cycle, cytarabine is administered intravenously at 3 g/m$^2$/day for 3 or 4 days and a compound of formula (I) or AC220 is orally administered at 200 mg/day for about 14 up to about 32 days. In one embodiment, the compound of formula (I) or AC220 is orally administered at 200 mg/day on days 4 through 28. In another embodiment, the compound of formula (I) or AC220 is orally administered at 200 mg/day on days 6 through 28. In another embodiment, the cytarabine is administered on days 1, 3 and 5. In another embodiment, the cytarabine is administered on days 1, 3, 5 and 7.

In one embodiment, for one treatment cycle, AC220 is orally administered for 14 days, idarubicin is administered intravenously at 12 mg/m$^2$ over 1 hour daily on days 1, 2, and 3, cytarabine is administered intravenously as continuous infusion at 1.5 g/m$^2$ over 24 hours daily on days 1 to 4, and solumedrol is administered at 50 mg or dexamethasone is administered intravenously at 10 mg daily for 3-4 days with cytarabine (days 1 to 4). In certain embodiments, AC220 is administered at a dose of 75 mg/m$^2$/day, 100 mg/m$^2$/day, 125 mg/m$^2$/day, or 150 mg/m$^2$/day.

In one embodiment, for one treatment cycle, cytarabine is administered intravenously at 1.5 g/m$^2$/day on days 1 through 4 and idarubicin is administered intravenously at 12 mg/m$^2$/day on days 1 through 3 and a compound of formula (I) or AC220 is orally administered at 90 mg/day for about 14 up to about 32 days. In one embodiment, a compound of formula (I) or AC220 is orally administered at 90 mg/day on days 1 through 14. In another embodiment, a compound of formula (I) or AC220 is orally administered at 90 mg/day on days 4 through 21. In another embodiment, a compound of formula (I) or AC220 is orally administered at 90 mg/day on days 4 through 28.

In one embodiment, for one treatment cycle, cytarabine is administered intravenously at 1.5 g/m$^2$/day on days 1 through 4 and idarubicin is administered intravenously at 12 mg/m$^2$/day on days 1 through 3 and a compound of formula (I) or AC220 is orally administered at 135 mg/day for about 14 up to about 32 days. In one embodiment, a compound of formula (I) or AC220 is orally administered at 135 mg/day on days 1 through 14. In another embodiment, a compound of formula (I) or AC220 is orally administered at 135 mg/day on days 4 through 21. In another embodiment, a compound of formula (I) or AC220 is orally administered at 135 mg/day on days 4 through 28.

In one embodiment, for one treatment cycle, cytarabine is administered intravenously at 1.5 g/m$^2$/day on days 1 through 4 and idarubicin is administered intravenously at 12 mg/m$^2$/day on days 1 through 3 and a compound of formula (I) or AC220 is orally administered at 200 mg/day for about 14 up to about 32 days. In one embodiment, a compound of formula (I) or AC220 is orally administered at 200 mg/day on days 1 through 14. In another embodiment, a compound of formula (I) or AC220 is orally administered at 200 mg/day on days 4 through 21. In another embodiment, a compound of formula (I) or AC220 is orally administered at 200 mg/day on days 4 through 28.

In one embodiment, for one treatment cycle, cytarabine is administered intravenously at 2 g/m$^2$/day for 6 days and a compound of formula (I) or AC220 is orally administered at 90 mg/day for about 14 up to about 32 days. In one embodiment, the compound of formula (I) or AC220 is orally administered at 90 mg/day on days 4 through 28. In another embodiment, the compound of formula (I) or AC220 is orally administered at 90 mg/day on days 6 through 28.

In one embodiment, for one treatment cycle, cytarabine is administered intravenously at 2 g/m$^2$/day for 6 days and a compound of formula (I) or AC220 is orally administered at 135 mg/day for about 14 up to about 32 days. In one embodiment, the compound of formula (I) or AC220 is orally administered at 135 mg/day on days 4 through 28. In another embodiment, the compound of formula (I) or AC220 is orally administered at 135 mg/day on days 6 through 28.

In one embodiment, for one treatment cycle, cytarabine is administered intravenously at 2 g/m$^2$/day for 6 days and a compound of formula (I) or AC220 is orally administered at 200 mg/day for about 14 up to about 32 days. In one embodiment, the compound of formula (I) or AC220 is orally administered at 200 mg/day on days 4 through 28. In another embodiment, the compound of formula (I) or AC220 is orally administered at 200 mg/day on days 6 through 28.

In one embodiment, for one treatment cycle, AC220 is orally administered daily for up to 4 weeks, idarubicin is administered intravenously at 8 mg/m$^2$ over 1 hour daily for 2 days, cytarabine is administered intravenously at 1.5 g/m$^2$ over 24 hours daily for 3 days, and solumedrol is administered at 50-100 mg or dexamethasone is administered intravenously at 10 mg daily for 3 days with cytarabine (days 1 to 3). In certain embodiments, AC220 is administered at a dose of 75 mg/m$^2$/day, 100 mg/m$^2$/day, 125 mg/m$^2$/day, or 150 mg/m$^2$/day.

In one embodiment, for one treatment cycle, cytarabine is administered intravenously at 0.75 g/m$^2$/day on days 1 through 3 and idarubicin is administered intravenously at 8 mg/m$^2$/day on days 1 and 2 and a compound of formula (I) or AC220 is orally administered at 90 mg/day for about 14 up to about 32 days. In one embodiment, a compound of formula (I) or AC220 is orally administered at 90 mg/day on days 1 through 14. In another embodiment, a compound of formula (I) or AC220 is orally administered at 90 mg/day on days 4 through 21. In another embodiment, a compound of formula (I) or AC220 is orally administered at 90 mg/day on days 4 through 28. In another embodiment, a compound of formula (I) or AC220 is orally administered at 90 mg/day on days 4 through 33.

In one embodiment, for one treatment cycle, cytarabine is administered intravenously at 0.75 g/m$^2$/day on days 1 through 3 and idarubicin is administered intravenously at 8 mg/m$^2$/day on days 1 and 2 and a compound of formula (I) or AC220 is orally administered at 135 mg/day for about 14 up to about 32 days. In one embodiment, a compound of formula (I) or AC220 is orally administered at 135 mg/day on days 1 through 14. In another embodiment, a compound of formula (I) or AC220 is orally administered at 135 mg/day on days 4 through 21. In another embodiment, a compound of formula (I) or AC220 is orally administered at 135 mg/day on days 4 through 28. In another embodiment, a compound of formula (I) or AC220 is orally administered at 135 mg/day on days 4 through 33.

In one embodiment, for one treatment cycle, cytarabine is administered intravenously at 0.75 g/m$^2$/day on days 1 through 3 and idarubicin is administered intravenously at 8 mg/m$^2$/day on days 1 and 2 and a compound of formula (I) or AC220 is orally administered at 200 mg/day for about 14 up to about 32 days. In one embodiment, a compound of formula (I) or AC220 is orally administered at 200 mg/day on days 1 through 14. In another embodiment, a compound of formula (I) or AC220 is orally administered at 200 mg/day on days 4 through 21. In another embodiment, a compound of formula (I) or AC220 is orally administered at 200 mg/day on days 4 through 28. In another embodiment, a compound of formula (I) or AC220 is orally administered at 200 mg/day on days 4 through 33.

In one embodiment, for one treatment cycle, idarubicin is administered intravenously at 12 mg/m$^2$ on days 1, 3, and 5, cytarabine is administered intravenously as continuous infusion at 100 mg/m$^2$ days 1 to 7, AC220 is orally administered at a dose of 200 mg/day on days 4-21. In one embodiment, the treatment cycle further comprises administering all-trans retinoic acid (ATRA) at a dose of 45 mg/m$^2$ on days 6-8 and 15 mg/m$^2$ on days 9-21.

In one embodiment, for one treatment cycle, cytarabine is administered intravenously at 3 g/m$^2$ for every 12 hours on days 1-3, and AC220 is orally administered at a dose of 200 mg/day on days 3-21. In one embodiment, the treatment cycle further comprises administering all-trans retinoic acid (ATRA) at a dose of 15 mg/m$^2$ on days 4-21.

In one embodiment, for one treatment cycle, etoposide is administered intravenously at 150 mg/m$^2$/day on days 1-5, cytarabine is administered intravenously at 1000 mg/m$^2$/day given every 12 hours on days 1 to 5, AC220 is orally administered daily on days 5-28, and methotrxate is administered intrathecally at a dose of 8 mg, 10 mg, 12 mg, or 15 mg on day 0. In one embodiment, AC220 is administered at a dose of 75 mg/m$^2$/day, 100 mg/m$^2$/day, 125 mg/m$^2$/day, or 150 mg/m$^2$/day.

In one embodiment, for one treatment cycle, etoposide is administered intravenously at 150 mg/m$^2$/day on days 1-5, cytarabine is administered intravenously at 1000 mg/m$^2$/day given every 12 hours on days 1 to 5, AC220 is orally administered daily on days 5-28, and cytarabine is administered intrathecally at a dose of 30 mg, 50 mg, or 70 mg on day 0.

iii) Combination of a Compound of Formula (I) or AC220 and Clofarabine

In one embodiment of the present method, the compound of structural formula (I) as described above, or a salt, solvate, ester and/or prodrug thereof comprises AC220; and the nucleoside analog comprises clofarabine.

In one embodiment, for one treatment cycle, the combination regimen comprises an oral administration of a compound of formula (I) or AC220 using a regimen selected from the group consisting of:
  A. 60 mg/day of a compound of formula (I) or AC220 for 14 days,
  B. 60 mg/day of a compound of formula (I) or AC220 for 28 days,
  C. 90 mg/day of a compound of formula (I) or AC220 for 14 days,
  D. 90 mg/day of a compound of formula (I) or AC220 for 28 days,
  E. 135 mg/day of a compound of formula (I) or AC220 for 14 days,
  F. 135 mg/day of a compound of formula (I) or AC220 for 28 days,
  G. 200 mg/day of a compound of formula (I) or AC220 for 14 days,
  H. 200 mg/day of a compound of formula (I) or AC220 for 28 days,
  I. 300 mg/day of a compound of formula (I) or AC220 for 14 days,
  J. 300 mg/day of a compound of formula (I) or AC220 for 28 days,
  K. 450 mg/day of a compound of formula (I) or AC220 for 14 days, and
  L. 450 mg/day of a compound of formula (I) or AC220 for 28 days;
and an intravenous administration of clofarabine regimen selected from the group consisting of:
  ii. 10 mg/m$^2$/day of clofarabine for 5 days,
  iia. 15 mg/m$^2$/day of clofarabine for 5 days,
  iib. 20 mg/m$^2$/day of clofarabine for 5 days,
  iic. 22.5 mg/m$^2$/day of clofarabine for 5 days,
  iid. 30 mg/m$^2$/day of clofarabine for 5 days,
  iie. 40 mg/m$^2$/day of clofarabine for 5 days, and
  iif. 52 mg/m$^2$/day of clofarabine for 5 days,
wherein the combination regimen is administered simultaneously, concurrently, separately or sequentially.

In another embodiment, the combination regimen further comprises an intravenous administration of cytarabine using a regimen selected from the following group:
  iiia. 1 g/m$^2$/day of cytarabine for 5 days
  iiib. 1 g/m$^2$/day of cytarabine for 7 days,
  iiic. 1.5 g/m$^2$/day of cytarabine for 3 days,
  iiid. 1.5 g/m$^2$/day of cytarabine for 5 days,
  iiie. 2 g/m$^2$/day of cytarabine for 3 days,
  iiif. 2 g/m$^2$/day of cytarabine for 4 days,
  iiig. 2 g/m$^2$/day of cytarabine for 5 days,
  iiih. 2 g/m$^2$/day of cytarabine for 6 days,
  iiii. 3 g/m$^2$/day of cytarabine for 3 days,
  iiij. 3 g/m$^2$/day of cytarabine for 4 days,
  iiik. 3 g/m$^2$/day of cytarabine for 5 days,
  iiil. 3 g/m$^2$/day of cytarabine for 6 days,
  iiim. 4 g/m$^2$/day of cytarabine for 3 days,
  iiin. 4 g/m$^2$/day of cytarabine for 4 days,
  iiio. 4 g/m$^2$/day of cytarabine for 5 days,
  iiip. 4 g/m$^2$/day of cytarabine for 6 days,
  iiiq. 6 g/m$^2$/day of cytarabine for 3 days,
  iiir. 6 g/m$^2$/day of cytarabine for 4 days,
  iiis. 6 g/m$^2$/day of cytarabine for 5 days, and
  iiit. 6 g/m$^2$/day of cytarabine for 6 days,
wherein the combination regimen is administered simultaneously, concurrently, separately or sequentially.

In another embodiment, the combination regimen comprising a compound of formula (I) or AC220 and clofarabine further comprises an intravenous administration of an anthracycline using a regimen selected from the following group:
  ia: 45 mg/m$^2$/day of daunorubicin for 3 days,
  ib: 50 mg/m$^2$/day of daunorubicin for 3 days,
  ic: 60 mg/m$^2$/day of daunorubicin for 3 days,
  id: 45-60 mg/m$^2$/day of daunorubicin for 3 days,
  ie: 70 mg/m$^2$/day of daunorubicin for 3 days,
  if: 12 mg/m$^2$/day of idarubicin for 3 days, and
  ig: 12 mg/m$^2$/day of mitoxantrone for 3 days;
wherein the combination regimen is administered simultaneously, concurrently, separately or sequentially.

In one embodiment, in one treatment cycle, clofarabine is administered intravenously at 40 mg/m$^2$/day for the first 5 consecutive days and a compound of formula (I) or AC220 is administered orally at 200 mg/day for 14 consecutive days following the completion of the administration of clofarabine. In one embodiment, in one treatment cycle, clofarabine is administered intravenously at 52 mg/m$^2$/day for the first 5 consecutive days and a compound of formula (I) or AC220 is administered orally at 200 mg/day for 14 consecutive days following the completion of the administration of clofarabine.

In another embodiment, in one treatment cycle, a compound of formula (I) or AC220 is administered orally at 200 mg/day for 14 consecutive days and clofarabine is administered intravenously at 40 mg/m$^2$/day for 5 consecutive days following the completion of the administration of a compound of formula (I) or AC220. In another embodiment, in one treatment cycle, a compound of formula (I) or AC220 is administered orally at 200 mg/day for 14 consecutive days and clofarabine is administered intravenously at 52 mg/m$^2$/day for 5 consecutive days following the completion of the administration of a compound of formula (I) or AC220.

In another embodiment, in one treatment cycle, clofarabine is administered invravenously at 40 mg/m$^2$/day for the first 5 consecutive days and a compound of formula (I) or AC220 is administered orally at 200 mg/day for the first 14 consecutive days. In another embodiment, in one treatment cycle, clofarabine is administered intravenously at 40 mg/m$^2$/day for the first 5 consecutive days and a compound of formula (I) or AC220 is administered orally at 200 mg/day for the first 28 consecutive days. In another embodiment, in one treatment cycle, clofarabine is administered intravenously at 52 mg/m$^2$/day for the first 5 consecutive days and a compound of formula (I) or AC220 is administered orally at 200 mg/day for the first 14 consecutive days. In another embodiment, in one treatment cycle, clofarabine is administered intravenously at 52 mg/m$^2$/day for the first 5 consecutive days and a compound of formula (I) or AC220 is administered orally at 200 mg/day for the first 28 consecutive days.

In one embodiment, for one treatment cycle, AC220 is orally administered for 14 days, and clofarabine is administered daily at 10 mg/m$^2$, 15 mg/m$^2$, 20 mg/m$^2$, 25 mg/m$^2$, or 30 mg/m$^2$, for the first 5 days.

iv) Combination of AC220 and Cladribine

In one embodiment of the present method, the compound of structural formula (I) as described above, or a salt, solvate, ester and/or prodrug thereof comprises AC220; and the nucleoside analog comprises cladribine.

In one embodiment, for one treatment cycle, the combination regimen comprises an oral administration of a compound of formula (I) or AC220 using a regimen selected from the group consisting of:
A. 60 mg/day of a compound of formula (I) or AC220 for 14 days,
B. 60 mg/day of a compound of formula (I) or AC220 for 28 days,
C. 90 mg/day of a compound of formula (I) or AC220 for 14 days,
D. 90 mg/day of a compound of formula (I) or AC220 for 28 days,
E. 135 mg/day of a compound of formula (I) or AC220 for 14 days,
F. 135 mg/day of a compound of formula (I) or AC220 for 28 days,
G. 200 mg/day of a compound of formula (I) or AC220 for 14 days,
H. 200 mg/day of a compound of formula (I) or AC220 for 28 days,
I. 300 mg/day of a compound of formula (I) or AC220 for 14 days,
J. 300 mg/day of a compound of formula (I) or AC220 for 28 days,
K. 450 mg/day of a compound of formula (I) or AC220 for 14 days, and
L. 450 mg/day of a compound of formula (I) or AC220 for 28 days;
and an intravenous administration of cladribine regimen selected from the group consisting of:
ii. 0.09 mg/kg/day of cladribine for 7 days,
iia. 12 mg/m$^2$/day of cladribine for 5 days,
iib. 0.15 mg/kg/day of cladribine for 5 days,
iic. 5.6 mg/m$^2$/day of cladribine for 5 days,
iid. 0.875 mg/kg/day of cladribine for 2 days,
iie. 0.875 mg/kg/day of cladribine for 4 days,
wherein the combination regimen is administered simultaneously, concurrently, separately or sequentially.

In one embodiment, cladribine is administered by subcutaneous injection at a dose of 1.5 mg/m$^2$ three times daily for 7 days.

In another embodiment, the combination regimen further comprises an intravenous administration of cytarabine using a regimen selected from the following group:
iiia. 1 g/m$^2$/day of cytarabine for 5 days
iiib. 1 g/m$^2$/day of cytarabine for 7 days,
iiic. 1.5 g/m$^2$/day of cytarabine for 3 days,
iiid. 1.5 g/m$^2$/day of cytarabine for 5 days,
iiie. 2 g/m$^2$/day of cytarabine for 3 days,
iiif. 2 g/m$^2$/day of cytarabine for 4 days,
iiig. 2 g/m$^2$/day of cytarabine for 5 days,
iiih. 2 g/m$^2$/day of cytarabine for 6 days,
iiii. 3 g/m$^2$/day of cytarabine for 3 days,
iiij. 3 g/m$^2$/day of cytarabine for 4 days,
iiik. 3 g/m$^2$/day of cytarabine for 5 days,
iiil. 3 g/m$^2$/day of cytarabine for 6 days,
iiim. 4 g/m$^2$/day of cytarabine for 3 days,
iiin. 4 g/m$^2$/day of cytarabine for 4 days,
iiio. 4 g/m$^2$/day of cytarabine for 5 days,
iiip. 4 g/m$^2$/day of cytarabine for 6 days,
iiiq. 6 g/m$^2$/day of cytarabine for 3 days,
iiir. 6 g/m$^2$/day of cytarabine for 4 days,
iiis. 6 g/m$^2$/day of cytarabine for 5 days, and
iiit. 6 g/m$^2$/day of cytarabine for 6 days,
wherein the combination regimen is administered simultaneously, concurrently, separately or sequentially.

In another embodiment, the combination regimen comprising a compound of formula (I) or AC220 and clofarabine further comprises administration of an anthracycline using a regimen known to one of skill in the art.

v) Combination of AC220 and Etoposide

In one embodiment, the second agent is etoposide and the dose of etoposide is about 10 mg/m$^2$ to about 150 mg/m$^2$, about 20 mg/m$^2$ to about 120 mg/m$^2$, or about 30 mg/m$^2$ to 100 mg/m$^2$. In another embodiment, the dose of etoposide is about 35 mg/m$^2$. In another embodiment, the dose of etoposide is about 50 mg/m$^2$. In another embodiment, the dose of etoposide is about 100 mg/m$^2$. In one embodiment, the dose of etoposide is about 50 to 100 mg/m$^2$ per day for 5 days. In one embodiment, the dose of etoposide is about 35 mg/m$^2$ per day for 4 days. In one embodiment, the dose of etoposide is about 50 mg/m$^2$ per day for 5 days. In one embodiment, the dose of etoposide is about 100 mg/m$^2$ per day on days 1, 3 and 5. In one embodiment, the administration of etoposide is once a day for 5 days, while the administration of AC220 occurs once a day for one week, two weeks, three weeks, four weeks or five weeks. In one embodiment, the administration of etoposide is once a day on days 1, 3 and 5, while the administration of AC220 occurs once a day for one week, two weeks, three weeks, four weeks or five weeks. In one embodiment, the administration of etoposide is once a day for 4 days, while the administration of AC220 occurs once a day for one week, two weeks, three weeks, four weeks or five weeks.

The administration of etoposide can be made by intravenous infusion, intravenous push, bolus injection or subcutaneous injection.

In one embodiment, for one treatment cycle, etoposide is administered for three, four or five days before the administration of AC220. In another embodiment, for one treatment cycle, etoposide is administered for three, four or five days that overlap with the administration of AC220.

In some embodiments, the methods of treating cancer comprise administering from about 60 mg/day AC220 and about 35 mg/m$^2$ of etoposide; about 90 mg/day AC220 and about 35 mg/m$^2$ of etoposide; about 135 mg/day AC220 and about 35 mg/m$^2$ of etoposide; about 200 mg/day AC220 and about 35 mg/m$^2$ of etoposide; or about 450 mg/day AC220 and about 35 mg/m$^2$ of etoposide.

In some embodiments, the methods of treating cancer comprise administering from about 60 mg/day AC220 and about 35 mg/m$^2$ of etoposide; about 90 mg/day AC220 and about 35 mg/m$^2$ of etoposide; about 135 mg/day AC220 and about 35 mg/m$^2$ of etoposide; about 200 mg/day AC220 and about 35 mg/m$^2$ of etoposide; or about 450 mg/day AC220 and about 35 mg/m$^2$ of etoposide.

In some embodiments, the methods of treating cancer comprise administering from about 60 mg/day AC220 and about 50 mg/m$^2$ of etoposide; about 90 mg/day AC220 and about 50 mg/m$^2$ of etoposide; about 135 mg/day AC220 and about 50 mg/m$^2$ of etoposide; about 200 mg/day AC220 and about 50 mg/m$^2$ of etoposide; or about 450 mg/day AC220 and about 50 mg/m$^2$ of etoposide.

In some embodiments, the methods of treating cancer comprise administering from about 60 mg/day AC220 and about 100 mg/m$^2$ of etoposide; about 90 mg/day AC220 and about 100 mg/m$^2$ of etoposide; about 135 mg/day AC220 and about 100 mg/m$^2$ of etoposide; about 200 mg/day AC220 and about 100 mg/m$^2$ of etoposide; or about 450 mg/day AC220 and about 100 mg/m$^2$ of etoposide.

In some embodiments, the methods of treating cancer comprise administering from about 60 mg/day AC220 and about 150 mg/m$^2$ of etoposide; about 90 mg/day AC220 and about 150 mg/m$^2$ of etoposide; about 135 mg/day AC220 and about 150 mg/m$^2$ of etoposide; about 200 mg/day AC220 and about 150 mg/m$^2$ of etoposide; or about 450 mg/day AC220 and about 150 mg/m$^2$ of etoposide.

In one embodiment, the combination regimen, for one treatment cycle, comprises an oral administration of AC220 using a regimen selected from:
A. 60 mg/day of a compound formula (I) or AC220 for 14 days,
B. 60 mg/day of a compound formula (I) or AC220 for 28 days,
C. 90 mg/day of a compound formula (I) or AC220 for 14 days,
D. 90 mg/day of a compound formula (I) or AC220 for 28 days,
E. 135 mg/day of a compound formula (I) or AC220 for 14 days,
F. 135 mg/day of a compound formula (I) or AC220 for 28 days,
G. 200 mg/day of a compound formula (I) or AC220 for 14 days,
H. 200 mg/day of a compound formula (I) or AC220 for 28 days,
I. 300 mg/day of a compound formula (I) or AC220 for 14 days,
J. 300 mg/day of a compound formula (I) or AC220 for 28 days,
K. 450 mg/day of a compound formula (I) or AC220 for 14 days, and
L. 450 mg/day of a compound formula (I) or AC220 for 28 days;
and an intravenous administration of etoposide using a regimen selected from the following group:
i. 50-100 mg/m$^2$/day of etoposide for five days;
ii. 50-100 mg/m$^2$/day etoposide for days 1 through 5;
iii. 5-100 mg/m$^2$/day etoposide for three days;
iv. 5-100 mg/m$^2$/day etoposide for three days;
v. 150 mg/m$^2$/day etoposide for days 1 through 5;
vi. 150 mg/m$^2$/day etoposide for 5 days;
vii. 35 mg/m$^2$/day for etoposide four days;
viii. 40 mg/m$^2$/day for etoposide four days;
ix. 45 mg/m$^2$/day for etoposide four days;
x. 50 mg/m$^2$/day for etoposide four days;
wherein the combination regimen is administered simultaneously, concurrently, separately or sequentially.

In another embodiment, the combination regimen, for one treatment cycle, comprises an oral administration of AC220 using a regimen selected from:
A. 25 mg/day of a compound formula (I) or AC220 for 14-32 days,
B. 25 mg/day of a compound formula (I) or AC220 for 23 days,
C. 50 mg/day of a compound formula (I) or AC220 for 14-32 days s,
D. 50 mg/day of a compound formula (I) or AC220 for 23 days,
E. 75 mg/day of a compound formula (I) or AC220 for 14-32 days,
F. 75 mg/day of a compound formula (I) or AC220 for 23 days,
G. 100 mg/day of a compound formula (I) or AC220 for 14-32 days,
H. 100 mg/day of a compound formula (I) or AC220 for 23 days,
I. 125 mg/day of a compound formula (I) or AC220 for 14-32 days,
J. 125 mg/day of a compound formula (I) or AC220 for 23 days,
K. 150 mg/day of a compound formula (I) or AC220 for 14-32 days,
L. 150 mg/day of a compound formula (I) or AC220 for 23 days;
M. 200 mg/day of a compound formula (I) or AC220 for 14-32 days,
N. 200 mg/day of a compound formula (I) or AC220 for 23 days;
and an intravenous administration of etoposide using a regimen selected from the following group:
i. 50-150 mg/m$^2$/day of etoposide for five days; and
ii. 150 mg/m$^2$/day of etoposide for five days;
and an intravenous administration of cytarabine using a regimen selected from the following group:
a. 1 g/m$^2$/day of cytarabine for 5 days
b. 1 g/m$^2$/day of cytarabine for 7 days,
c. 1.5 g/m$^2$/day of cytarabine for 3 days,
d. 1.5 g/m$^2$/day of cytarabine for 5 days,
e. 2 g/m$^2$/day of cytarabine for 3 days,
f. 2 g/m$^2$/day of cytarabine for 4 days,
g. 2 g/m$^2$/day of cytarabine for 5 days, and
h. 2 g/m$^2$/day of cytarabine for 6 days, wherein the combination regimen is administered simultaneously, concurrently, separately or sequentially. In one embodiment, cytarabine and etoposide are both administered on days 1 through 5 and AC220 is administered on days 5-28. In one embodiment, cytarabine and etoposide are both administered on days 1 through 5 and AC220 is administered on days 6-28. In one embodiment, cytarabine and etoposide are both administered on days 1 through 5 and AC220 is administered on days 6-19.

vi) Combination of AC220 and Daunorubicin

In one embodiment, the second agent is etoposide and the dose of daunorubicin is about 10 mg/m$^2$ to about 100 mg/m$^2$, about 10 mg/m$^2$ to about 60 mg/m$^2$, about 10 mg/m$^2$ to about 50 mg/m$^2$, about 20 mg/m$^2$ to about 50 mg/m$^2$, or about 20 mg/m$^2$, 45 mg/m$^2$. In another embodiment, the dose of daunorubicin is about 25 mg/m$^2$. In another embodiment, the dose of daunorubicin is about 30 mg/m$^2$. In another embodiment, the dose of daunorubicin is about 45 mg/m$^2$. In another embodiment, the dose of daunorubicin is about 60 mg/m$^2$. In one embodiment, the administration of daunorubicin is once a day on days 1, 2 and 3, while the administration of AC220 occurs once a day for one week, two weeks, three weeks, four weeks or five weeks. In one embodiment, the administration of daunorubicin is once a day on days 1, and 2, while the administration of AC220 occurs once a day for one week, two weeks, three weeks, four weeks or five weeks. In one embodiment, the administration of daunorubicin is once a day on day 1, while the administration of AC220 occurs once a day for one week, two weeks, three weeks, four weeks or five weeks. The administration of daunorubicin can be made by intravenous infusion, intravenous push, bolus injection or subcutaneous injection.

In one embodiment, for one treatment cycle, the anthracycline is administered for three days before the administration of AC220. In another embodiment, for one treatment cycle, the anthracycline is administered for three days that overlap with the administration of AC220. In another embodiment, for one treatment cycle, the anthracycline is administered for three days that following the administration of AC220.

In some embodiments, the methods of treating cancer comprise administering from about 60 mg/day AC220 and about 25 mg/m$^2$ of daunorubicin; about 90 mg/day AC220 and about 25 mg/m$^2$ of daunorubicin; about 135 mg/day AC220 and about 25 mg/m$^2$ of daunorubicin; about 200 mg/day AC220 and about 25 mg/m$^2$ of daunorubicin; or about 450 mg/day AC220 and about 25 mg/m$^2$ of daunorubicin.

In some embodiments, the methods of treating cancer comprise administering from about 60 mg/day AC220 and about 30 mg/m$^2$ of daunorubicin; about 90 mg/day AC220 and about 30 mg/m$^2$ of daunorubicin; about 135 mg/day AC220 and about 30 mg/m$^2$ of daunorubicin; about 200 mg/day AC220 and about 30 mg/m$^2$ of daunorubicin; or about 450 mg/day AC220 and about 30 mg/m$^2$ of daunorubicin.

In some embodiments, the methods of treating cancer comprise administering from about 60 mg/day AC220 and about 45 mg/m$^2$ of daunorubicin; about 90 mg/day AC220 and about 45 mg/m$^2$ of daunorubicin; about 135 mg/day AC220 and about 45 mg/m$^2$ of daunorubicin; about 200 mg/day AC220 and about 45 mg/m$^2$ of daunorubicin; or about 450 mg/day AC220 and about 45 mg/m$^2$ of daunorubicin.

In some embodiments, the methods of treating cancer comprise administering from about 60 mg/day AC220 and about 60 mg/m$^2$ of daunorubicin; about 90 mg/day AC220 and about 60 mg/m$^2$ of daunorubicin; about 135 mg/day AC220 and about 60 mg/m$^2$ of daunorubicin; about 200 mg/day AC220 and about 45 mg/m$^2$ of daunorubicin; or about 450 mg/day AC220 and about 60 mg/m$^2$ of daunorubicin.

In one embodiment, the combination regimen, for one treatment cycle, comprises an oral administration of AC220 using a regimen selected from:

A. 60 mg/day of a compound formula (I) or AC220 for 14 days,
B. 60 mg/day of a compound formula (I) or AC220 for 28 days,
C. 90 mg/day of a compound formula (I) or AC220 for 14 days,
D. 90 mg/day of a compound formula (I) or AC220 for 28 days,
E. 135 mg/day of a compound formula (I) or AC220 for 14 days,
F. 135 mg/day of a compound formula (I) or AC220 for 28 days,
G. 200 mg/day of a compound formula (I) or AC220 for 14 days,
H. 200 mg/day of a compound formula (I) or AC220 for 28 days,
I. 300 mg/day of a compound formula (I) or AC220 for 14 days,
J. 300 mg/day of a compound formula (I) or AC220 for 28 days,
K. 450 mg/day of a compound formula (I) or AC220 for 14 days, and
L. 450 mg/day of a compound formula (I) or AC220 for 28 days;
and an intravenous administration of an anthracycline using a regimen selected from the following group:
i: 45 mg/m$^2$/day of daunorubicin for 3 days,
ii: 50 mg/m$^2$/day of daunorubicin for 3 days,
iii: 60 mg/m$^2$/day of daunorubicin for 3 days,
iv: 45-60 mg/m$^2$/day of daunorubicin for 3 days,
vi: 70 mg/m$^2$/day of daunorubicin for 3 days,
wherein the combination regimen is administered simultaneously, concurrently, separately or sequentially.

F. Exemplary Dosing Schedules of AC220 and Second Agents

In certain embodiments, AC220 and/or a pharmaceutically acceptable salt, prodrug, solvate or hydrate thereof and the second agents provided herein can be administered according to any schedule deemed suitable by a practitioner of skill in the art. Provided in this section are exemplary dosing schedules of AC220 and/or a pharmaceutically acceptable salt, prodrug, solvate or hydrate thereof in combination with the second agents that can be practiced in the methods provided herein.

In certain embodiments, AC220 and/or a pharmaceutically acceptable salt, prodrug, solvate or hydrate thereof and the second agents are administered in cycles. In certain embodiments, AC220 and/or a pharmaceutically acceptable salt, prodrug, solvate or hydrate thereof and the second agents are administered in at least one cycle. In certain embodiments, AC220 and/or a pharmaceutically acceptable salt, prodrug, solvate or hydrate thereof and the second agents are administered in at least two cycles. In certain embodiments, AC220 and/or a pharmaceutically acceptable salt, prodrug, solvate or hydrate thereof and the second agents are administered in at least three cycles. In certain embodiments, AC220 and/or a pharmaceutically acceptable salt, prodrug, solvate or hydrate thereof and the second agents are administered in at least four cycles. In certain embodiments each cycle is at least 28 days. In one embodiment, the second agent is etoposide. In one embodiment, the second agent is daunorubicin. In one embodiment, the second agent is idarubicin. In one embodiment, the second agent is cytarabine. In one embodiment, the second agent is AZA. In one embodiment, the second agent is clofarabine.

In certain embodiments, the initial dose of AC220 and/or a pharmaceutically acceptable salt, prodrug, solvate or hydrate thereof is administered before the administration of the second agent. In certain embodiments, the initial dose of AC220and/or a pharmaceutically acceptable salt, prodrug, solvate or hydrate thereof is administered immediately before the administration of the second agent. In certain embodiments, administration of the second agent is initiated 1, 2, 3, 4, 8, 12, 16, 24, or 32 hours or 1, 2, 3, 4, 5, 6, or 7 days following administration of AC220, for instance, 1, 2, 3, 4, 8, 12, 16, 24, or 32 hours or 1, 2, 3, 4, 5, 6, or 7 days following completion of the administration of AC220 and/or a pharmaceutically acceptable salt, prodrug, solvate or hydrate thereof.

In certain embodiments, the initial dose of AC220 and/or a pharmaceutically acceptable salt, prodrug, solvate or hydrate thereof is administered after the administration of the second agent. In certain embodiments, the initial dose of AC220 and/or a pharmaceutically acceptable salt, prodrug, solvate or hydrate thereof is administered immediately after the administration of the second agent. In certain embodiments, administration of AC220 and/or a pharmaceutically acceptable salt, prodrug, solvate or hydrate thereof is initiated 1, 2, 3, 4, 8, 12, 16, 24, or 32 hours or 1, 2, 3, 4, 5, 6, or 7 days following administration of the second agent, for instance, 1, 2, 3, 4, 8, 12, 16, 24, or 32 hours or 1, 2, 3, 4, 5, 6, or 7 days following completion of the administration of the second agent.

G. Patient Population

In certain embodiments, AC220 and/or a pharmaceutically acceptable salt, prodrug, solvate or hydrate thereof and the second agents provided herein can be administered to any cancer patient deemed suitable by a practitioner of skill in the art.

In one embodiment, the methods provided herein are for treatment of a patient who has relapsed or refractory to a prior cancer therapy. In certain embodiments, the patient is relapsed after a first, second, third or subsequent cancer therapy.

In certain embodiments, the patient is 60 years or older and relapsed after a first line cancer therapy. In certain embodiments, the patient is 18 years or older and is relapsed or refractory after a second line cancer therapy. In certain embodiments, the patient is 18 years or older and is relapsed or refractory after a third or subsequent line cancer therapy. In certain embodiments, the patient is 60 years or older and is refractory to a first line cancer therapy. In certain embodiments, the patient is 70 years or older and is previously untreated. In certain embodiments, the patient is 70 years or older and is ineligible and/or unlikely to benefit from cancer therapy.

In certain embodiments, the patients previously untreated who are ineligible and/or unlikely to benefit from cancer therapy include patients having at least one of the following adverse factors: prior MDS, unfavorable cytogenetics at diagnosis, ECOG (Eastern Cooperative Oncology Group) performance status 1, 2 or 3, or $\geq 75$ years of age.

In certain embodiments, the patient is
a) 60 years or older and relapsed after a first line cancer therapy,
b) 60 years or older and is refractory to a first line cancer therapy,
c) 18 years or older and is relapsed or refractory after a second line cancer therapy, or
d) 70 years or older and is previously untreated who is ineligible and/or unlikely to benefit from cancer therapy.

In certain embodiments, the patient is relapsed after a third-line cancer therapy or a salvage therapy.

In certain embodiments, the patient is 60, 65, 70, 75, 80, 85 or older and relapsed after a first line cancer therapy. In certain embodiments, the patient is 60, 65, 70, 75, 80, 85 or older and is refractory to a first line cancer therapy. In certain embodiments, the patient is 18, 20, 25, 30, 35, 40, 45, 50, 55, 60, 65, 70, 75, 80, 85 or older and relapsed after a second line cancer therapy. In certain embodiments, the patient is 70, 75, 80, 85 or older and is previously untreated who is ineligible and/or unlikely to benefit from cancer therapy.

In certain embodiments, the patients previously untreated who are ineligible and/or unlikely to benefit from chemotherapy include patients having at least one of the following adverse factors: prior MDS (myelodysplastic syndrome), unfavorable cytogenetics at diagnosis, ECOG (Eastern Cooperative Oncology Group) performance status 2, or $\geq 75$ years of age.

In some embodiments, the patient is treated based on the Eastern Cooperative Oncology Group (ECOG) performance status score of the patient for leukemia. ECOG performance status can be scored on a scale of 0 to 5, with 0 denoting asymptomatic; 1 denoting symptomatic but completely ambulant; 2 denoting symptomatic and <50% in bed during the day; 3 denoting symptomatic and >50% in bed, but not bed bound; 4 denoting bed bound; and 5 denoting death. In some embodiments, the patient has an ECOG performance status score of 0, 1, 2 or 3. In other embodiments, the patient has an ECOG performance status score of 0, 1 or 2. In other embodiments, the patient has an ECOG performance status score of 1 or 2. In some embodiments, the patient has an ECOG performance status score of 2 or 3. In other embodiments, the patient has an ECOG performance status score of 2.

In certain embodiments, the methods provided herein comprise administering the compound at least about 2, 3, 4, 5, 6, 7, 8, 9, 10, 11 or 12 hours after meal. In certain embodiments, the compound is administered about 1, 2, 3, 4, 5 or 6 hours before meal. In certain embodiments, the compound is administered at least about 2 hours after meal and about 1 hour or more before meal.

In certain embodiments, the methods provided herein encompass treating a subject regardless of patient's age, although some diseases or disorders are more common in certain age groups. Further provided herein is a method for treating a subject who has undergone surgery in an attempt to treat the disease or condition at issue, as well as the one who have not. Because the subjects with cancer have heterogeneous clinical manifestations and varying clinical outcomes, the treatment given to a particular subject may vary, depending on his/her prognosis. The skilled clinician will be able to readily determine without undue experimentation, specific secondary agents, types of surgery, and types of non-drug based standard therapy that can be effectively used to treat an individual subject with cancer.

In certain embodiments, the methods provided herein are used to treat heavily pretreated patients. A heavily pretreated patient is defined as a patient who has been treated previously with, for example, three or more than three courses of a cancer therapy. In certain embodiments, heavily pretreated patient has been treated with 3, 4, 5, 6, 7, 8, 9 or 10 cancer therapy treatment regimens. The heavily pretreated patient could be pretreated by any cancer therapy regime deemed suitable by one of skill in the art. In certain embodiments, the heavily pretreated patients had been previously treated with one or more FLT3 inhibitors, for example, CEP701, PKC412, MLN-518, sunitinib and sorafenib.

In certain embodiments, the methods provided herein are used to treat minimally pretreated patients. Patients, who have not been treated previously or have been treated but are not considered heavily pretreated, are minimally pretreated patients.

In certain embodiments, the patient is 65 years or younger with newly diagnosed AML or MDS.

In certain embodiments, the patient is 18 years or older with newly diagnosed AML exhibiting a FLT3-ITD mutation. In certain embodiments, the patient is 18 years or older with newly diagnosed AML exhibiting a FLT3-ITD stratified by NPM1 mutation.

In certain embodiments, the patient is 18 years or older with high-risk MDS, CMML or AML, who has failed prior therapy. In certain embodiments, the patient with MDS has failed prior therapy with a hypomethylating agent and/or with lenalidomide. In certain embodiments, the patient with AML has failed any prior induction therapy or have relapsed after prior therapy. In certain embodiments, the patient with MDS has received therapy with a hypomethylating agent and progressed to AML, regardless any prior therapy for AML. In certain embodiments, the patient has not received any prior therapy and is not a candidate to receive standard therapy.

In certain embodiments, the patient is 18 years or older with newly diagnosed CBF-AML.

In certain embodiments, the patient meets the following criteria:
1. diagnosed 1) AML (WHO classification definition of >/=20% blasts), or 2) intermediate-2 or high-risk MDS (defined by the IPSS classification);
2. aged 15 to 65 years;
3. patient has relapsed or refractory disease or secondary untreated disease, in certain embodiments, the patient has not had prior exposure to a FLT3 inhibitor;
4. ECOG performance status ≦2
5. Normal organ function In certain embodiments, the patient has not received any chemotherapy (except hydrea) for AML or MDS. In certain embodiments, the patient has received hypomethylating agents for prior MDS and transfusions, hematopoietic growth factors or vitamins.

In certain embodiments, the patient meets the following criteria:
1. Patient is at high risk of relapse, crtiteria for which are: a) FLT3 ITDs or D835 mutations, (b) complex karyotypes (at least 3 distinct abnormalities) (c) a CRp or CRi, (d) in 2nd or greater CR
2.) Patient is not a candidate for allogeneic HCT
3.) Patient is in CR, CRp, or CRi within 1 week prior to initiation of therapy
4.) Patient has serum bilirubin and creatinine each <2 mg/dl
5) Patient does not have QTc prolongation
6.) Patient (a) does not have other diseases that would limit the life expectancy to <1 year or preclude compliance with AC220 therapy, (b) does not have HIV infection and (c) has not previously received AC220.

In certain embodiments, the patient is 18 years or older and meets the following criteria:
1 Patient has MDS, CMML or AML, who have failed prior therapy.
   a. Patient with MDS has failed prior therapy with a hypomethylating agent and/or with lenalidomide.
   b. Patient with AML has failed any prior induction therapy or have relapsed after prior therapy.
   c. Patient with MDS has received therapy with a hypomethylating asgent and progress to AML.
   d. Patient has received no prior therapy and is not a candidate to receive standard therapy.
2. ECOG Performance Status ≦2
3. Adequate liver (bilirrubin ≦2 mg/dl) and renal (creatinine ≦2 mg/dl) function.

In certain embodiments, the patient is between 1 to 21 years of age. In certain embodiments, the patient is diagnosed with relapsed/refractory AML, ALL or acute leukemia of ambiguous lineage and meet the following criteria:
1. the patient has AML or leukemia with ambiguous lineage and has >5% blasts in the bone marrow;
2. the patient with ALL has an M3 marrow (marrow blasts >25%);
3. the patient with ALL has MLL gene rearrangement or hyperdiploid >50 chromosomes;
4. the patients with treatment related AML (t-AML) are eligible, provided they meet all other eligibility criteria.

H. Pharmaceutical Compositions

The methods provided herein use pharmaceutical compositions containing AC220 and/or a pharmaceutically acceptable prodrug, salt, solvate or hydrate thereof and pharmaceutically acceptable carriers, such as diluents or adjuvants, or in combination with a second agent. In certain embodiments, the second agent, for example, cytarabine, clofarabie, AZA, etoposide, idarubicin or daunorubicin, is administered as pharmaceutical compositions known in the art.

Exemplary pharmaceutical compositions of AC220, or a pharmaceutically acceptable prodrug, salt, solvate or hydrate thereof are described in U.S. Patent Application Pub. Nos. US 2007/0232604, US 2009/0123418, US 2009/0131426 and U.S. Provisional App. No. 61/243,977. In one embodiment, the pharmaceutical compositions comprise at least one nonrelease controlling excipients or carriers. In another embodiment, the pharmaceutical compositions comprise at least one release controlling and at least one nonrelease controlling excipients or carriers. In one embodiment, the pharmaceutical compositions provided herein are spray-dried compositions.

In another embodiment, the pharmaceutical compositions comprise AC220, or a pharmaceutically acceptable prodrug, salt, solvate or hydrate thereof, as an active ingredient, in combination with one or more pharmaceutically acceptable carriers, each of which is selected from the group consisting of hydroxypropyl-β-cyclodextrin, mannitol, sodium starch glycolate (EXPLOTAB®), citric acid, PEG400, PEG6000, polyvinylpyrrolidone (PVP), lauroyl polyoxylglycerides (GELUCIRE® 44/14, Gattefosse Corp., Paramus, N.J.), PLURONIC® F68, silicone dioxide, and water. PLURONIC® F68 (also known as Poloxamer 188) is a block copolymer of ethylene oxide and propylene oxide.

In another embodiment, the pharmaceutical compositions comprise AC220, or a pharmaceutically acceptable prodrug, salt, solvate or hydrate thereof, and hydroxypropyl-β-cyclodextrin (HPBCD). In certain embodiments, the HPBCD-containing composition is formulated as an aqueous solution, which is obtained by adding an aqueous HPBCD solution at a desired concentration to the appropriate amount of AC220, or a pharmaceutically acceptable prodrug, salt, solvate or hydrate thereof, to achieve a desired final concentration of the compound, including, but not limited to, final concentrations of about 1, about 2, about 3, about 5, about 10, about 15, about 50, or about 100 mg/mL. In one embodiment, the HPBCD composition contains about 5% HPBCD. In another embodiment, the HPBCD composition contains about 22% HPBCD. In certain embodiments, the pharmaceutical composition contains 2, 3, or 5 mg/mL of AC220, or a pharmaceutically acceptable prodrug, salt, solvate or hydrate thereof, in 5% HPBCD. In certain embodiments, the pharmaceutical composition contains 1, 3, or 10 mg/mL of a compound of AC220, or a pharmaceutically acceptable prodrug, salt, solvate or hydrate thereof, in 22% HPBCD. Exemplary pharmaceutical compositions are shown in Table 2.

TABLE 2

| Component | Formulation Ia (2 mg/mL Preparation) | Formulation Ib (5 mg/mL Preparation) |
| --- | --- | --- |
| AC220 in vial (mg) | 50 mg | 50 mg |
| HPBCD (5% stock, freshly prepared) | 25 mL | 10 mL |

In yet another embodiment, the pharmaceutical composition of AC220 is reconstituted with an aqueous solution that comprises one or more pharmaceutically acceptable carriers, prior to administration. In one embodiment, the pharmaceutical composition comprises AC220, or a pharmaceutically acceptable prodrug, salt, solvate or hydrate thereof. In another embodiment, the pharmaceutical composition comprises AC220 in a vial. In yet another embodiment, the pharmaceutical composition comprises from about 1 to about 200 mg, from about 10 to about 100 mg, or from about 10 to 60 mg, or 10 mg, 12 mg, 14 mg, 16 mg, 18 mg, 20 mg, 25 mg, 27 mg, 30 mg, 35 mg, 40 mg, 45 mg, 50 mg, 55 mg, or 60 mg of the compound, or a pharmaceutically acceptable prodrug, salt, solvate or hydrate thereof. In one embodiment, the aqueous solution used for reconstitution comprises HPBCD. In certain embodiments, the aqueous solution comprises 5% by weight of HPBCD. In certain embodiments, the aqueous solution comprises 22% by weight of HPBCD.

In yet another embodiment, the pharmaceutical composition comprises AC220, or a pharmaceutically acceptable prodrug, salt, solvate or hydrate thereof, in combination with PEG 400 and water. In certain embodiments, the ratio between PEG400 and water is 3 to 1.

In yet another embodiment, the pharmaceutical composition comprises AC220, or a pharmaceutically acceptable prodrug, salt, solvate or hydrate thereof, in combination with mannitol and EXPLOTAB®. In certain embodiments, the pharmaceutical composition is formulated as capsules. Exemplary pharmaceutical compositions are shown in Table 3.

TABLE 3

| Component | Formulation IIa | Formulation IIb |
| --- | --- | --- |
| AC220 | 75 mg | 25 mg |
| Mannitol | 282 mg | 332 mg |
| EXPLOTAB ® | 22.8 mg | 22.8 mg |

In yet another embodiment, the pharmaceutical composition comprises AC220, or a pharmaceutically acceptable prodrug, salt, solvate or hydrate thereof, in combination with mannitol, EXPLOTAB®, and citric acid. In certain embodiments, the pharmaceutical composition is formulated as capsules. In certain embodiments, AC220, or a pharmaceutically acceptable prodrug, salt, solvate or hydrate thereof, is micronized, e.g., using jet-mill. Exemplary pharmaceutical compositions are shown in Table 4.

TABLE 4

| Component | Formulation IIIa | Formulation IIIb |
| --- | --- | --- |
| AC220 | 75 mg | 25 mg |
| Mannitol | 206 mg | 309 mg |
| EXPLOTAB ® | 22.8 mg | 22.8 mg |
| Citric acid | 76 mg | 25 mg |

In yet another embodiment, the pharmaceutical composition comprises AC220, or a pharmaceutically acceptable prodrug, salt, solvate or hydrate thereof, in combination with PEG6000, mannitol, and EXPLOTAB®. In certain embodiments, the pharmaceutical composition is formulated as capsules. Exemplary pharmaceutical compositions are shown in Table 5.

TABLE 5

| Component | Formulation IVa | Formulation IVb |
| --- | --- | --- |
| AC220 | 50 mg | 30 mg |
| PEG6000 | 113 mg (31%) | 70.5 mg (18.8%) |
| Mannitol | 158 mg (43.3%) | 229.5 mg (61.2%) |
| EXPLOTAB ® | 44 (12%) | 45 mg (12%) |

In yet another embodiment, the pharmaceutical composition comprises AC220, or a pharmaceutically acceptable prodrug, salt, solvate or hydrate thereof, in combination with polyvinylpyrrolidone (PVP), mannitol, and EXPLOTAB®. In certain embodiments, the pharmaceutical composition is formulated as capsules. Exemplary pharmaceutical compositions are shown in Table 6.

TABLE 6

| Component | Formulation Va | Formulation Vb |
| --- | --- | --- |
| AC220 | 75 mg | 25 mg |
| Mannitol | 226 mg | 276 mg |
| PVP | 14 mg | 14 mg |
| EXPLOTAB ® | 35 mg | 35 mg |

In yet another embodiment, the pharmaceutical composition comprises AC220, or a pharmaceutically acceptable prodrug, salt, solvate or hydrate thereof, in combination with GELUCIRE®. In certain embodiments, the pharmaceutical composition is formulated as capsules. In certain embodiments, the pharmaceutical composition comprises a dihydrochloride of N-(5-tert-butyl-isoxazol-3-yl)-N'-{4-[7-(2-morpholin-4-yl-ethoxy)imidazo[2,1-b][1,3]benzothiazol-2-yl]phenyl}urea and GELUCIRE® 44/14. An exemplary pharmaceutical composition is shown in Table 7.

TABLE 7

| Component | Formulation VI |
| --- | --- |
| AC220 | 50 mg |
| GELUCIRE ® | 470 mg |

In yet another embodiment, the pharmaceutical composition comprises AC220, or a pharmaceutically acceptable prodrug, salt, solvate or hydrate thereof, in combination with GELUCIRE® and PEG6000. In certain embodiments, the pharmaceutical composition is formulated as capsules. In certain embodiments, the pharmaceutical composition comprises three parts by weight of GELUCIRE® and one parts by weight of PEG6000.

In yet another embodiment, the pharmaceutical composition comprises AC220, or a pharmaceutically acceptable prodrug, salt, solvate or hydrate thereof, in combination with mannitol, EXPLOTAB®, and PLURONIC® F68. In certain embodiments, the pharmaceutical composition is formulated as capsules. An exemplary pharmaceutical composition is shown in Table 8.

TABLE 8

| Component | Formulation VII |
|---|---|
| AC220 | 75 mg |
| Mannitol | 275.5 mg |
| EXPLOTAB ® | 22.8 mg |
| PLURONIC ® F68 | 11.4 mg |

In yet another embodiment, the pharmaceutical composition comprises AC220, or a pharmaceutically acceptable prodrug, salt, solvate or hydrate thereof, in combination with GELUCIRE®, PEG6000, silicone dioxide, mannitol, and EXPLOTAB®. In certain embodiments, the pharmaceutical composition is formulated as capsules. An exemplary pharmaceutical composition is shown in Table 9.

TABLE 9

| Component | Formulation VIII |
|---|---|
| AC220 | 60 mg |
| GELUCIRE ® | 37.5 mg |
| PEG 6000 | 112.5 mg |
| Silicone dioxide | 10 mg |
| Mannitol | 117.5 |
| EXPLOTAB ® | 37.5 mg |

In yet another embodiment, the pharmaceutical composition comprises AC220, or a pharmaceutically acceptable prodrug, salt, solvate or hydrate thereof, in combination with HPBCD, mannitol, and EXPLOTAB®. In certain embodiments, the pharmaceutical composition is formulated as capsules. An exemplary pharmaceutical composition is shown in Table 10.

TABLE 10

| Component | Formulation IX |
|---|---|
| AC220 | 70 mg |
| HPBCD | 140 mg |
| Mannitol | 119 mg |
| EXPLOTAB ® | 21 mg |

In still another embodiment, the pharmaceutical composition comprises AC220, or a pharmaceutically acceptable prodrug, salt, solvate or hydrate thereof, in combination with HPBCD. In certain embodiments, the pharmaceutical composition is formulated as lyophilized powder. In certain embodiments, AC220 used in the pharmaceutical composition is a cocrystal of AC220, or a pharmaceutically acceptable prodrug, salt, solvate or hydrate thereof, and HPBCD. As used here, the term "cocrystal" refers to a crystal containing two or more distinct molecular components within the crystal lattice (unit cell). An exemplary pharmaceutical composition is shown in Table 11.

TABLE 11

| Component | Formulation Xa | Formulation Xb | Formulation Xc |
|---|---|---|---|
| AC220 | 10 mg | 10 mg | 75 mg |
| HPBCD | 110 mg | 50 mg | 75 mg |

In one embodiment, provided herein is a spray-dried pharmaceutical composition which comprises AC220, or a pharmaceutically acceptable prodrug, salt, solvate or hydrate thereof, and HPBCD. In certain embodiments, the spray-dried composition is obtained by spray drying an aqueous solution of AC220, or a pharmaceutically acceptable prodrug, salt, solvate or hydrate thereof In certain embodiments, the aqueous solution is obtained by adding an aqueous HPBCD solution at a desired concentration to the appropriate amount of AC220, or a pharmaceutically acceptable prodrug, salt, solvate or hydrate thereof, to achieve a desired final concentration of the compound, including, but not limited to, final concentrations of about 1, about 2, about 3, about 5, about 10, about 15, about 30, about 40, about 50, about 75, or about 100 mg/mL. In one embodiment, the compositions provided herein comprise about 5% HPBCD. In another embodiment, the the compositions provided herein comprise about 22% HPBCD. In one embodiment, the compositions provided herein comprise about 20% HPBCD. In one embodiment, the compositions provided herein comprise about 40% HPBCD. In one embodiment, the compositions provided herein comprise about 50% HPBCD.

In certain embodiments, the compositions provided herein comprise 40 mg of AC220 dissolved for each mL of 40% HPBCD solution, for a total of 100 mg compound dissolved in a total of 2.5 mL 40% HPBCD solution. In certain embodiments, the compositions provided herein comprise 40 mg of AC220 dissolved for each mL of 40% HPBCD solution, for a total of 200 mg compound dissolved in a total of 5 mL 40% HPBCD solution.

In certain embodiments, the compositions provided herein comprise AC220 and HPBCD in a ratio of about 1:5, 1:7, 1:10, 1:13, 1:15, or 1:20 by weight. In certain embodiments, the compositions provided herein comprise AC220 and HPBCD in a ratio of about 1:10 by weight. In an exemplary embodiment, about 1.1 g spray-dried composition provided herein comprises about 100 mg of AC220 and about 1000 mg of HPBCD. In another exemplary embodiment, about 2.2 g spray-dried composition provided herein comprises about 200 mg of AC220 and about 2000 mg of HPBCD.

In certain embodiments, provided herein is a spray-dried pharmaceutical composition for reconstitution with an aqueous solution, prior to administration. In one embodiment, the spray-dried pharmaceutical composition in a vial. In one embodiment, the spray-dried compositions provided herein are reconstituted with water to provide an aqueous solution comprising about 1-10, 2-10, 3-10, 2-8, or 3-7 mg of the spray-dried composition per mL of water. In one embodiment, the spray-dried compositions provided herein are reconstituted with water to provide an aqueous solution comprising about 1, 2, 3, 4, 5, 6, 7, 8, 9 or 10 mg of the spray-dried composition per mL of water.

In certain embodiments, the pharmaceutical compositions are formulated in a dosage from about 1 to about 100 mg, or from about 1 to about 60 mg, or from about 10 to about 60 mg, from about 10 to about 40 mg, from about 10 to about 27 mg, or from about 10 to about 25 mg of AC220, or a pharmaceutically acceptable prodrug, salt, solvate or hydrate thereof.

In certain embodiments, AC220 used in the pharmaceutical compositions provided herein is in a solid form. Suitable solid forms include, but are not limited to, solid forms comprising the free base of AC220, and solid forms comprising salts of AC220, including, but not limited to, HCl salts, HBr salts, sulfate salts, mesylate salts, esylate salts, edisylate salts, besylate salts, tosylate salts, and napsylate salts. In certain embodiments, the HCl salts of AC220 include mono-HCl salts and bis-HCl salts. In certain embodiments, solid forms provided herein include polymorphs, solvates (including hydrates), and cocrystals comprising AC220 and/or salts thereof. In certain embodiments, the solid form is a cocrystal of AC220, or a pharmaceutically acceptable prodrug, salt, solvate or hydrate thereof, and HPBCD. In certain embodiments, AC220 used in the pharmaceutical compositions provided herein is a dihydrochloride salt of N-(5-tert-butyl-isoxazol-3-yl)-N'-{4-[7-(2-morpholin-4-yl-ethoxy)imidazo[2,1-b][1,3]benzothiazol-2-yl]phenyl}urea. Some of these solid forms are described in US 2009/0123418; incorporated herein by reference in its entirety.

The pharmaceutical compositions may be formulated in various dosage forms for oral, parenteral, and topical administration. The pharmaceutical compositions may also be formulated as modified release dosage forms, including delayed-, extended-, prolonged-, sustained-, pulsed-, controlled-, accelerated- and fast-, targeted-, programmed-release, and gastric retention dosage forms. These dosage forms can be prepared according to conventional methods and techniques known to those skilled in the art (see, *Remington: The Science and Practice of Pharmacy, supra; Modified-Release Drug Deliver Technology*, Rathbone et al., Eds., Drugs and the Pharmaceutical Science, Marcel Dekker, Inc.: New York, N.Y., 2003; Vol. 126).

In one embodiment, the pharmaceutical compositions are provided in a dosage form for oral administration. In another embodiment, the pharmaceutical compositions are provided in a dosage form for parenteral administration. In yet another embodiment, the pharmaceutical compositions are provided in a dosage form for topical administration.

The pharmaceutical compositions of AC220 may be provided in a unit-dosage form or multiple-dosage form. A unit-dosage form, as used herein, refers to a physically discrete unit suitable for administration to human and animal subjects, and packaged individually as is known in the art. Each unit-dose contains a predetermined quantity of the active ingredient(s) sufficient to produce the desired therapeutic effect, in association with the required pharmaceutical carriers or excipients. Examples of a unit-dosage form include an ampoule, syringe, and individually packaged tablet and capsule. A unit-dosage form may be administered in fractions or multiples thereof. A multiple-dosage form is a plurality of identical unit-dosage forms packaged in a single container to be administered in segregated unit-dosage form. Examples of a multiple-dosage form include a vial, bottle of tablets or capsules, or bottle of pints or gallons.

The pharmaceutical compositions of AC220 may be administered at once or multiple times at intervals of time. It is understood that the precise dosage and duration of treatment may vary with the age, weight, and condition of the patient being treated, and may be determined empirically using known testing protocols or by extrapolation from in vivo or in vitro test or diagnostic data. It is further understood that for any particular individual, specific dosage regimens should be adjusted over time according to the individual need and the professional judgment of the person administering or supervising the administration of the formulations.

A. Oral Administration

Further to these discussed above, the pharmaceutical compositions of AC220 may be provided in solid, semisolid, or liquid dosage forms for oral administration. As used herein, oral administration also includes buccal, lingual, and sublingual administration. Suitable oral dosage forms include, but are not limited to, tablets, capsules, pills, troches, lozenges, pastilles, cachets, pellets, medicated chewing gum, granules, bulk powders, effervescent or non-effervescent powders or granules, solutions, emulsions, suspensions, solutions, wafers, sprinkles, elixirs, and syrups. In addition to the active ingredient(s), the pharmaceutical compositions may contain one or more pharmaceutically acceptable carriers or excipients, including, but not limited to, binders, fillers, diluents, disintegrants, wetting agents, lubricants, glidants, coloring agents, dye-migration inhibitors, sweetening agents, and flavoring agents.

Binders or granulators impart cohesiveness to a tablet to ensure the tablet remaining intact after compression. Suitable binders or granulators include, but are not limited to, starches, such as corn starch, potato starch, and pre-gelatinized starch (e.g., STARCH 1500); gelatin; sugars, such as sucrose, glucose, dextrose, molasses, and lactose; natural and synthetic gums, such as acacia, alginic acid, alginates, extract of Irish moss, panwar gum, ghatti gum, mucilage of isabgol husks, carboxymethylcellulose, methylcellulose, polyvinylpyrrolidone (PVP), Veegum, larch arabogalactan, powdered tragacanth, and guar gum; celluloses, such as ethyl cellulose, cellulose acetate, carboxymethyl cellulose calcium, sodium carboxymethyl cellulose, methyl cellulose, hydroxyethylcellulose (HEC), hydroxypropylcellulose (HPC), hydroxypropyl methyl cellulose (HPMC); microcrystalline celluloses, such as AVICEL-PH-101, AVICEL-PH-103, AVICEL RC-581, AVICEL-PH-105 (FMC Corp., Marcus Hook, Pa.); and mixtures thereof. Suitable fillers include, but are not limited to, talc, calcium carbonate, microcrystalline cellulose, powdered cellulose, dextrates, kaolin, mannitol, silicic acid, sorbitol, starch, pre-gelatinized starch, and mixtures thereof. The binder or filler may be present from about 50 to about 99% by weight in the pharmaceutical compositions provided herein.

Suitable diluents include, but are not limited to, dicalcium phosphate, calcium sulfate, lactose, sorbitol, sucrose, inositol, cellulose, kaolin, mannitol, sodium chloride, dry starch, and powdered sugar. Certain diluents, such as mannitol, lactose, sorbitol, sucrose, and inositol, when present in sufficient quantity, can impart properties to some compressed tablets that permit disintegration in the mouth by chewing. Such compressed tablets can be used as chewable tablets.

Suitable disintegrants include, but are not limited to, agar; bentonite; celluloses, such as methylcellulose and carboxymethylcellulose; wood products; natural sponge; cation-exchange resins; alginic acid; gums, such as guar gum and Veegum HV; citrus pulp; cross-linked celluloses, such as croscarmellose; cross-linked polymers, such as crospovidone; cross-linked starches; calcium carbonate; microcrystalline cellulose, such as sodium starch glycolate; polacrilin potassium; starches, such as corn starch, potato starch, tapioca starch, and pre-gelatinized starch; clays; aligns; and mixtures thereof. The amount of a disintegrant in the pharmaceutical compositions provided herein varies upon the type of formulation, and is readily discernible to those of ordinary skill in the art. The pharmaceutical compositions provided herein may contain from about 0.5 to about 15% or from about 1 to about 5% by weight of a disintegrant.

Suitable lubricants include, but are not limited to, calcium stearate; magnesium stearate; mineral oil; light mineral oil;

glycerin; sorbitol; mannitol; glycols, such as glycerol behenate and polyethylene glycol (PEG) (e.g., PEG400 and PEG6000); stearic acid; sodium lauryl sulfate; talc; hydrogenated vegetable oil, including peanut oil, cottonseed oil, sunflower oil, sesame oil, olive oil, corn oil, and soybean oil; zinc stearate; ethyl oleate; ethyl laureate; agar; starch; lycopodium; silica (silicone dioxide) or silica gels, such as AEROSIL® 200 (W.R. Grace Co., Baltimore, Md.) and CAB-O-SIL® (Cabot Co. of Boston, Mass.); and mixtures thereof. The pharmaceutical compositions provided herein may contain about 0.1 to about 5% by weight of a lubricant.

Suitable glidants include colloidal silicon dioxide, CAB-O-SIL® (Cabot Co. of Boston, Mass.), and asbestos-free talc. Coloring agents include any of the approved, certified, water soluble FD&C dyes, and water insoluble FD&C dyes suspended on alumina hydrate, and color lakes and mixtures thereof. A color lake is the combination by adsorption of a water-soluble dye to a hydrous oxide of a heavy metal, resulting in an insoluble form of the dye. Flavoring agents include natural flavors extracted from plants, such as fruits, and synthetic blends of compounds which produce a pleasant taste sensation, such as peppermint and methyl salicylate. Sweetening agents include sucrose, lactose, mannitol, syrups, glycerin, and artificial sweeteners, such as saccharin and aspartame. Suitable emulsifying agents include gelatin, acacia, tragacanth, bentonite, and surfactants, such as polyoxyethylene sorbitan monooleate (e.g., TWEEN® 20), poloxamers (e.g., PLURONIC® F68), polyoxyethylene sorbitan monooleate 80 (e.g., TWEEN® 80), and triethanolamine oleate. Suspending and dispersing agents include sodium carboxymethylcellulose, pectin, tragacanth, Veegum, acacia, sodium carbomethylcellulose, hydroxypropyl methylcellulose, polyvinylpyrrolidone, and lauroyl polyoxylglycerides (e.g., GELUCIRE® 44/14). Preservatives include glycerin, methyl and propylparaben, benzoic add, sodium benzoate and alcohol. Wetting agents include propylene glycol monostearate, sorbitan monooleate, diethylene glycol monolaurate, and polyoxyethylene lauryl ether. Solvents include glycerin, sorbitol, ethyl alcohol, and syrup. Examples of non-aqueous liquids utilized in emulsions include mineral oil and cottonseed oil. Organic acids include citric and tartaric acid. Sources of carbon dioxide include sodium bicarbonate and sodium carbonate.

Suitable complexing agents include, but are not limited to, cyclodextrins, including α-cyclodextrin, β-cyclodextrin, hydroxypropyl-β-cyclodextrin, sulfobutylether-β-cyclodextrin, and sulfobutylether 7-β-cyclodextrin (CAPTISOL®, CyDex, Lenexa, Kans.).

It should be understood that many carriers and excipients may serve several functions, even within the same formulation.

The pharmaceutical compositions of AC220 may be provided as compressed tablets, tablet triturates, chewable lozenges, rapidly dissolving tablets, multiple compressed tablets, or enteric-coating tablets, sugar-coated, or film-coated tablets. Enteric-coated tablets are compressed tablets coated with substances that resist the action of stomach acid but dissolve or disintegrate in the intestine, thus protecting the active ingredients from the acidic environment of the stomach. Enteric-coatings include, but are not limited to, fatty acids, fats, phenyl salicylate, waxes, shellac, ammoniated shellac, and cellulose acetate phthalates. Sugar-coated tablets are compressed tablets surrounded by a sugar coating, which may be beneficial in covering up objectionable tastes or odors and in protecting the tablets from oxidation. Film-coated tablets are compressed tablets that are covered with a thin layer or film of a water-soluble material. Film coatings include, but are not limited to, hydroxyethylcellulose, sodium carboxymethylcellulose, polyethylene glycol 4000, and cellulose acetate phthalate. Film coating imparts the same general characteristics as sugar coating. Multiple compressed tablets are compressed tablets made by more than one compression cycle, including layered tablets, and press-coated or dry-coated tablets.

The tablet dosage forms may be prepared from the active ingredient in powdered, crystalline, or granular forms, alone or in combination with one or more carriers or excipients described herein, including binders, disintegrants, controlled-release polymers, lubricants, diluents, and/or colorants. Flavoring and sweetening agents are especially useful in the formation of chewable tablets and lozenges.

The pharmaceutical compositions of AC220 may be provided as soft or hard capsules, which can be made from gelatin, methylcellulose, starch, or calcium alginate. The hard gelatin capsule, also known as the dry-filled capsule (DFC), consists of two sections, one slipping over the other, thus completely enclosing the active ingredient. The soft elastic capsule (SEC) is a soft, globular shell, such as a gelatin shell, which is plasticized by the addition of glycerin, sorbitol, or a similar polyol. The soft gelatin shells may contain a preservative to prevent the growth of microorganisms. Suitable preservatives are those as described herein, including methyl- and propyl-parabens, and sorbic acid. The liquid, semisolid, and solid dosage forms provided herein may be encapsulated in a capsule. Suitable liquid and semisolid dosage forms include solutions and suspensions in propylene carbonate, vegetable oils, or triglycerides. Capsules containing such solutions can be prepared as described in U.S. Pat. Nos. 4,328,245; 4,409,239; and 4,410,545. The capsules may also be coated as known by those of skill in the art in order to modify or sustain dissolution of the active ingredient.

The pharmaceutical compositions of AC220 may be provided in liquid and semisolid dosage forms, including emulsions, solutions, suspensions, elixirs, and syrups. An emulsion is a two-phase system, in which one liquid is dispersed in the form of small globules throughout another liquid, which can be oil-in-water or water-in-oil. Emulsions may include a pharmaceutically acceptable non-aqueous liquid or solvent, emulsifying agent, and preservative. Suspensions may include a pharmaceutically acceptable suspending agent and preservative. Aqueous alcoholic solutions may include a pharmaceutically acceptable acetal, such as a di(lower alkyl) acetal of a lower alkyl aldehyde, e.g., acetaldehyde diethyl acetal; and a water-miscible solvent having one or more hydroxyl groups, such as propylene glycol and ethanol. Elixirs are clear, sweetened, and hydroalcoholic solutions. Syrups are concentrated aqueous solutions of a sugar, for example, sucrose, and may also contain a preservative. For a liquid dosage form, for example, a solution in a polyethylene glycol may be diluted with a sufficient quantity of a pharmaceutically acceptable liquid carrier, e.g., water, to be measured conveniently for administration.

Other useful liquid and semisolid dosage forms include, but are not limited to, those containing the active ingredient(s) provided herein, and a dialkylated mono- or poly-alkylene glycol, including, 1,2-dimethoxymethane, diglyme, triglyme, tetraglyme, polyethylene glycol-350-dimethyl ether, polyethylene glycol-550-dimethyl ether, polyethylene glycol-750-dimethyl ether, wherein 350, 550, and 750 refer to the approximate average molecular weight of the polyethylene glycol. These formulations may further comprise one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, bisulfite, sodium metabisulfite, thiodipropionic acid and its esters, and dithiocarbamates.

The pharmaceutical compositions of AC220 may be provided as non-effervescent or effervescent, granules and powders, to be reconstituted into a liquid dosage form. Pharmaceutically acceptable carriers and excipients used in the non-effervescent granules or powders may include diluents, sweeteners, and wetting agents. Pharmaceutically acceptable carriers and excipients used in the effervescent granules or powders may include organic acids and a source of carbon dioxide.

Coloring and flavoring agents can be used in all of the above dosage forms.

The pharmaceutical compositions of AC220 may be formulated as immediate or modified release dosage forms, including delayed-, sustained, pulsed-, controlled, targeted-, and programmed-release forms.

The pharmaceutical compositions of AC220 may be co-formulated with other active ingredients which do not impair the desired therapeutic action, or with substances that supplement the desired action. B. Parenteral Administration The pharmaceutical compositions of AC220 may be administered parenterally by injection, infusion, or implantation, for local or systemic administration. Parenteral administration, as used herein, include intravenous, intraarterial, intraperitoneal, intrathecal, intraventricular, intraurethral, intrasternal, intracranial, intramuscular, intrasynovial, and subcutaneous administration.

The pharmaceutical compositions of AC220 may be formulated in any dosage forms that are suitable for parenteral administration, including solutions, suspensions, emulsions, micelles, liposomes, microspheres, nanosystems, and solid forms suitable for solutions or suspensions in liquid prior to injection. Such dosage forms can be prepared according to conventional methods known to those skilled in the art of pharmaceutical science (see, Remington: The Science and Practice of Pharmacy, supra).

The pharmaceutical compositions of AC220 intended for parenteral administration may include one or more pharmaceutically acceptable carriers and excipients, including, but not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, cryoprotectants, lyoprotectants, thickening agents, pH adjusting agents, and inert gases.

Suitable aqueous vehicles include, but are not limited to, water, saline, physiological saline or phosphate buffered saline (PBS), sodium chloride injection, Ringers injection, isotonic dextrose injection, sterile water injection, dextrose and lactated Ringers injection. Non-aqueous vehicles include, but are not limited to, fixed oils of vegetable origin, castor oil, corn oil, cottonseed oil, olive oil, peanut oil, peppermint oil, safflower oil, sesame oil, soybean oil, hydrogenated vegetable oils, hydrogenated soybean oil, and medium-chain triglycerides of coconut oil, and palm seed oil. Water-miscible vehicles include, but are not limited to, ethanol, 1,3-butanediol, liquid polyethylene glycol (e.g., polyethylene glycol 300 and polyethylene glycol 400), propylene glycol, glycerin, N-methyl-2-pyrrolidone, N,N-dimethylacetamide, and dimethyl sulfoxide.

Suitable antimicrobial agents or preservatives include, but are not limited to, phenols, cresols, mercurials, benzyl alcohol, chlorobutanol, methyl and propyl p-hydroxybenzoates, thimerosal, benzalkonium chloride (e.g., benzethonium chloride), methyl- and propyl-parabens, and sorbic acid. Suitable isotonic agents include, but are not limited to, sodium chloride, glycerin, and dextrose. Suitable buffering agents include, but are not limited to, phosphate and citrate. Suitable antioxidants are those as described herein, including bisulfite and sodium metabisulfite. Suitable local anesthetics include, but are not limited to, procaine hydrochloride. Suitable suspending and dispersing agents are those as described herein, including sodium carboxymethylceluose, hydroxypropyl methylcellulose, and polyvinylpyrrolidone. Suitable emulsifying agents include those described herein, including polyoxyethylene sorbitan monolaurate, polyoxyethylene sorbitan monooleate 80, and triethanolamine oleate. Suitable sequestering or chelating agents include, but are not limited to EDTA. Suitable pH adjusting agents include, but are not limited to, sodium hydroxide, hydrochloric acid, citric acid, and lactic acid. Suitable complexing agents include, but are not limited to, cyclodextrins, including α-cyclodextrin, β-cyclodextrin, hydroxypropyl-β-cyclodextrin, sulfobutylether-β-cyclodextrin, and sulfobutylether 7-β-cyclodextrin (CAPTISOL®, CyDex, Lenexa, Kans.).

The pharmaceutical compositions of AC220 may be formulated for single or multiple dosage administration. The single dosage formulations are packaged in an ampoule, a vial, or a syringe. The multiple dosage parenteral formulations must contain an antimicrobial agent at bacteriostatic or fungistatic concentrations. All parenteral formulations must be sterile, as known and practiced in the art.

In one embodiment, the pharmaceutical compositions of AC220 are provided as ready-to-use sterile solutions. In another embodiment, the pharmaceutical compositions of AC220 are provided as sterile dry soluble products, including lyophilized powders and hypodermic tablets, to be reconstituted with a vehicle prior to use. In yet another embodiment, the pharmaceutical compositions of AC220 are provided as ready-to-use sterile suspensions. In yet another embodiment, the pharmaceutical compositions of AC220 are provided as sterile dry insoluble products to be reconstituted with a vehicle prior to use. In still another embodiment, the pharmaceutical compositions are provided as ready-to-use sterile emulsions.

The pharmaceutical compositions of AC220 may be formulated as immediate or modified release dosage forms, including delayed-, sustained, pulsed-, controlled, targeted, and programmed-release forms.

The pharmaceutical compositions of AC220 may be formulated as a suspension, solid, semi-solid, or thixotropic liquid, for administration as an implanted depot. In one embodiment, the pharmaceutical compositions provided herein are dispersed in a solid inner matrix, which is surrounded by an outer polymeric membrane that is insoluble in body fluids but allows the active ingredient in the pharmaceutical compositions diffuse through.

Suitable inner matrixes include polymethylmethacrylate, polybutylmethacrylate, plasticized or unplasticized polyvinylchloride, plasticized nylon, plasticized polyethylene terephthalate, natural rubber, polyisoprene, polyisobutylene, polybutadiene, polyethylene, ethylene-vinyl acetate copolymers, silicone rubbers, polydimethylsiloxanes, silicone carbonate copolymers, hydrophilic polymers, such as hydrogels of esters of acrylic and methacrylic acid, collagen, cross-linked polyvinyl alcohol, and cross-linked partially hydrolyzed polyvinyl acetate.

Suitable outer polymeric membranes include polyethylene, polypropylene, ethylene/propylene copolymers, ethylene/ethyl acrylate copolymers, ethylene/vinyl acetate copolymers, silicone rubbers, polydimethyl siloxanes, neoprene rubber, chlorinated polyethylene, polyvinylchloride, vinyl chloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer.

C. Topical Administration

The pharmaceutical compositions of AC220 may be administered rectally, urethrally, vaginally, or perivaginally in the forms of suppositories, pessaries, bougies, poultices or cataplasm, pastes, powders, dressings, creams, plasters, contraceptives, ointments, solutions, emulsions, suspensions, tampons, gels, foams, sprays, or enemas. These dosage forms can be manufactured using conventional processes as described in *Remington: The Science and Practice of Pharmacy*, supra.

Rectal, urethral, and vaginal suppositories are solid bodies for insertion into body orifices, which are solid at ordinary temperatures but melt or soften at body temperature to release the active ingredient(s) inside the orifices. Pharmaceutically acceptable carriers utilized in rectal and vaginal suppositories include bases or vehicles, such as stiffening agents, which produce a melting point in the proximity of body temperature, when formulated with the pharmaceutical compositions provided herein; and antioxidants as described herein, including bisulfite and sodium metabisulfite. Suitable vehicles include, but are not limited to, cocoa butter (theobroma oil), glycerin-gelatin, carbowax (polyoxyethylene glycol), spermaceti, paraffin, white and yellow wax, and appropriate mixtures of mono-, di- and triglycerides of fatty acids, hydrogels, such as polyvinyl alcohol, hydroxyethyl methacrylate, polyacrylic acid; glycerinated gelatin. Combinations of the various vehicles may be used. Rectal and vaginal suppositories may be prepared by the compressed method or molding. The typical weight of a rectal and vaginal suppository is about 2 to about 3 g.

The pharmaceutical compositions of AC220 may be administered intranasally or by inhalation to the respiratory tract. The pharmaceutical compositions of AC220 may be provided in the form of an aerosol or solution for delivery using a pressurized container, pump, spray, atomizer, such as an atomizer using electrohydrodynamics to produce a fine mist, or nebulizer, alone or in combination with a suitable propellant, such as 1,1,1,2-tetrafluoroethane or 1,1,1,2,3,3,3-heptafluoropropane. The pharmaceutical compositions of AC220 may also be provided as a dry powder for insufflation, alone or in combination with an inert carrier such as lactose or phospholipids; and nasal drops. For intranasal use, the powder may comprise a bioadhesive agent, including chitosan or cyclodextrin.

Solutions or suspensions for use in a pressurized container, pump, spray, atomizer, or nebulizer may be formulated to contain ethanol, aqueous ethanol, or a suitable alternative agent for dispersing, solubilizing, or extending release of the active ingredient provided herein, a propellant as solvent; and/or a surfactant, such as sorbitan trioleate, oleic acid, or an oligolactic acid.

The pharmaceutical compositions of AC220 herein may be micronized to a size suitable for delivery by inhalation, such as about 50 micrometers or less, or about 10 micrometers or less. Particles of such sizes may be prepared using a comminuting method known to those skilled in the art, such as spiral jet milling, fluid bed jet milling, supercritical fluid processing to form nanoparticles, high pressure homogenization, or spray drying.

Capsules, blisters and cartridges for use in an inhaler or insufflator may be formulated to contain a powder mix of the pharmaceutical compositions provided herein; a suitable powder base, such as lactose or starch; and a performance modifier, such as l-leucine, mannitol, or magnesium stearate. The lactose may be anhydrous or in the form of the monohydrate. Other suitable excipients or carriers include dextran, glucose, maltose, sorbitol, xylitol, fructose, sucrose, and trehalose. The pharmaceutical compositions provided herein for inhaled/intranasal administration may further comprise a suitable flavor, such as menthol and levomenthol, or sweeteners, such as saccharin or saccharin sodium.

The pharmaceutical compositions of a compound formula (I) or AC220 for topical administration may be formulated to be immediate release or modified release, including delayed, sustained, pulsed, controlled, targeted, and programmed release.

I. Articles of Manufacture and Kits

The combination regimes provided herein can also be provided as an article of manufacture using packaging materials well known to those of skill in the art. See, e.g., U.S. Pat. Nos. 5,323,907; 5,052,558; and 5,033,252. Examples of pharmaceutical packaging materials include, but are not limited to, blister packs, bottles, tubes, inhalers, pumps, bags, vials, containers, syringes, and any packaging material suitable for a selected formulation and intended mode of administration and treatment.

Provided herein also are kits which, when used by the medical practitioner, can simplify the administration of appropriate amounts of active ingredients to a subject. In certain embodiments, the kit provided herein includes containers and dosage forms of the compounds in the combination regimens provided herein.

In certain embodiments, the kit includes a container comprising dosage forms of the compounds in the combination regimens provided herein, in one or more containers.

Kits provided herein can further include devices that are used to administer the active ingredients. Examples of such devices include, but are not limited to, syringes, needle-less injectors drip bags, patches, and inhalers. The kits provided herein can also include condoms for administration of the active ingredients.

Kits provided herein can further include pharmaceutically acceptable vehicles that can be used to administer one or more active ingredients. For example, if an active ingredient is provided in a solid form that must be reconstituted for parenteral administration, the kit can comprise a sealed container of a suitable vehicle in which the active ingredient can be dissolved to form a particulate-free sterile solution that is suitable for parenteral administration. Examples of pharmaceutically acceptable vehicles include, but are not limited to: aqueous vehicles, including, but not limited to, Water for Injection USP, Sodium Chloride Injection, Ringer's Injection, Dextrose Injection, Dextrose and Sodium Chloride Injection, and Lactated Ringer's Injection; water-miscible vehicles, including, but not limited to, ethyl alcohol, polyethylene glycol, and polypropylene glycol; and non-aqueous vehicles, including, but not limited to, corn oil, cottonseed oil, peanut oil, sesame oil, ethyl oleate, isopropyl myristate, and benzyl benzoate.

The disclosure will be further understood by the following non-limiting examples.

Examples

Example 1

A Clinical Study

A clinical trial is to be conducted to determine the clinical activity and determine the toxicity profile of the combinations of azacytidine ("AZA") and N-(5-tert-Butyl-isoxazol-3-yl)-N'-{4-[7-(2-morpholin-4-yl-ethoxy)imidazo[2,1-b][1,3]benzothiazol-2-yl]phenyl}urea ("AC220") in patients with refractory or relapsed AML and/or MDS. In addition to clinical response, patients will be monitored for certain correlative studies, such as induction of hypomethylation, DNA damage, and FLT-3 signalling.

This trial is a phase I/II, single-arm, open-label study in which patients receive, for each 28-day treatment cycle, therapy comprising daily oral administration of a compound formula (I) or AC220 for the first 14 days and daily subcutaneous or intravenous administration of AZA for the first 7 days. Cycles are repeated approximately every 28 days and therapy is continued until disease progression or documentation of unacceptable toxicity.

Approximately 30 patients are expected to participate in the study. Patients eligible for enrollment are:

1. Patients with MDS, CMML or AML, who have failed prior therapy.
   a. Patients with MDS should have failed prior therapy with a hypomethylating agent and/or with lenalidomide.
   b. Patients with AML should have failed any prior induction therapy or have relapsed after prior therapy.
   c. Patients who with MDS who received therapy with a hypomethylating agent and progress to AML are eligible at the time of diagnosis of AML regardless of prior therapy for AML.
   d. Patients with any of the eligible diagnoses who have received no prior therapy are eligible if unfit to receive standard therapy.
2. Age ≧18 years
3. ECOG Performance Status ≦2
4. Adequate liver (bilirubin ≦2 mg/dl) and renal (creatinine ≦2 mg/dl) function.

One objective of the trial is to administer AZA and AC220 at full dose, starting at a dose level of −1 for the first six patients (See Tables A to E below). The study is a clinical trial with a byesian design with early stopping rules for futility and toxicity. If no more than 1 patient experiences unacceptable toxicity, all subsequent patients will be treated at dose level 0. The first 6 patients will be treated at dose level −1. If 2 or more of the first 6 patients treated at dose level 0 experience unacceptable toxicity, then all subsequent patients will be treated at dose level −1. Otherwise, all patients will be treated at dose level 0. A total of 30 patients will be treated.

Azacytidine is administered either subcutaneously or intravenously at 75 mg/m$^2$/day from day 1 through day 7 of a 28 day treatment cycle. AC220 is administered at dose level −1 which is one dose level below the maximum tolerated dose (MTD). The MTD for AC220 has not been reached and the possible AC220 dosage strength and schedule to be administered orally in combination with AZA are showed in the following tables:

TABLE A

| Dose level −1 | 75 mg/m$^2$/day of AZA on days 1 to 7; and 300 mg/day of AC220 on days 1 to 14, of a 28-day treatment cycle. |
| Dose level 0 | 75 mg/m$^2$/day of AZA on days 1 to 7; and 450 mg/day of AC220 on days 1 to 14, of a 28-day treatment cycle. |

TABLE B

| Dose level −1 | 75 mg/m$^2$/day of AZA on days 1 to 7; and 200 mg/day of AC220 on days 1 to 14, of a 28-day treatment cycle. |

TABLE B-continued

| Dose level 0 | 75 mg/m$^2$/day of AZA on days 1 to 7; and 300 mg/day of AC220 on days 1 to 14, of a 28-day treatment cycle. |

TABLE C

| Dose level −1 | 75 mg/m$^2$/day of AZA on days 1 to 7; and 300 mg/day of AC220 on days 1 to 28, of a 28-day treatment cycle. |
| Dose level 0 | 75 mg/m$^2$/day of AZA on days 1-7; and 450 mg/day of AC220 on days 1 to 28, of a 28-day treatment cycle. |

TABLE D

| Dose level −1 | 75 mg/m$^2$/day of AZA on days 1 to 7; and 200 mg/day of AC220 on days 1 to 28, of a 28-day treatment cycle. |
| Dose level 0 | 75 mg/m$^2$/day of AZA on days 1 to 7; and 300 mg/day of AC220 on days 1 to 28, of a 28-day treatment cycle. |

TABLE E

| Dose level −1 | 75 mg/m$^2$/day of AZA on days 1 to 7; and 135 mg/day of AC220 on days 1 to 28, of a 28-day treatment cycle. |
| Dose level 0 | 75 mg/m$^2$/day of AZA on days 1 to 7; and 200 mg/day of AC220 on days 1 to 28, of a 28-day treatment cycle. |

Primary efficacy variable will be the rate of CR, CRp, PR and HI (toxicity for the phase I portion of the study). Secondary efficacy variable will be the duration of remission and survival, toxicity, and quality of life. Toxicity will be evaluated according to NCI CTC v3.0.

Treatment cycles are repeated approximately every 28 days, and therapy is continued until disease progression or documentation of unacceptable toxicity. Responses are to be evaluated according to the criteria proposed by the international working group for MDS (Cheson et al. *Blood* 2006; 108: 419-25) and AML (Cheson et al. *J Clin Oncol* 2003; 21: 4642-9). An overall response rate of 20% will be considered significant.

Example 2

Efficacy Study of AC220 Plus Cytarabine in the MV4-11 Solid Tumor Flank Model

Efficacy study (in vivo) of AC220 plus cytarabine was conducted using MV4-11 solid tumor flank model in the SCID mouse. Dosing was initiated on day 14 post-inoculation with groups of 10 animals per arm. The size of the tumors averaged about 222 mm$^3$. AC220 was delivered in a formulation of 5% hydroxybetacycicodextrin aqueous solution (5 ml/kg/day, prepared weekly) at 1.0 mg/kg/day (mkd), QD, PO, and the dose was adjusted for body weight. Cytarabine was delivered in a formulation of sterile saline (5 ml/kg/day, prepared weekly) at about 30 or about 60 mkd, QD, IP, and dose was adjusted for body weight. The average group starting body weight was about 20 g. The clinical signs and body weight were measured twice weekly. White blood cell (WBC) counts determined at the end of the cytarabine dosing period and again 7 days post drug treatment. The study was carried out in one or multiple treatment cycles with cytarabine delivered for 10 days on each 24 day cycle. As shown in Table 12 below, cytarabine was delivered either prior to or concurrent with AC220, with AC220 administered only in the first dosing cycle.

TABLE 12

Dosing Schedule of AC220 and Cytarabine Efficacy Study for one cycle (24 days)

| Group | Dosing Schedule |
|---|---|
| 1. Control (untreated) | Day 1 to Day 24 |
| 2. AC220 vehicle (5% cyclodextrin) | Day 1 to Day 24 |
| 3. cytarabine alone | cytarabine (30 mkd) from Day 1 to Day 10; and 5% cyclodextrin from Day 1 to Day 24. |
| 4. AC220 alone | Saline from Day 1 to Day 10; and AC220 (1 mkd) from Day 1 to Day 24. |
| 5. AC220 alone | Saline from Day 1 to Day 10; and AC220 (1 mkd) from Day 1 to Day 24. |
| 6. AC220 plus cytarabine (sequential) | cytarabine (30 mkd) from Day 1 to Day 10; and AC220 (1 mkd) from Day 11 to Day 24. |
| 7. AC220 plus cytarabine (overlapping) | cytarabine (30 mkd) from Day 1 to Day 10; and AC220 (1 mkd) from Day 1 to Day 24. |

FIG. 1 shows the flank tumor volume for the arms that received overlapping administration of AC220 and cytarabine (Group 7) or a single drug and vehicle (Groups, 3 and 5). Comparing Group 5 to 7, cytarabine does not have an antagonistic affect on AC220, and furthermore, concurrent cytarabine administration with AC220 appears to result in a slower rate of rebound in tumor growth compared to treatment with AC220 alone. In fact, on this schedule, the combination lead to a 20% cure rate (sustained complete regressions) while treatment with either agent alone lead to no sustained complete regressions. This data suggests that concurrent administration of cytarabine and AC220 may be an effective schedule for the treatment of cancer.

Figure 2:
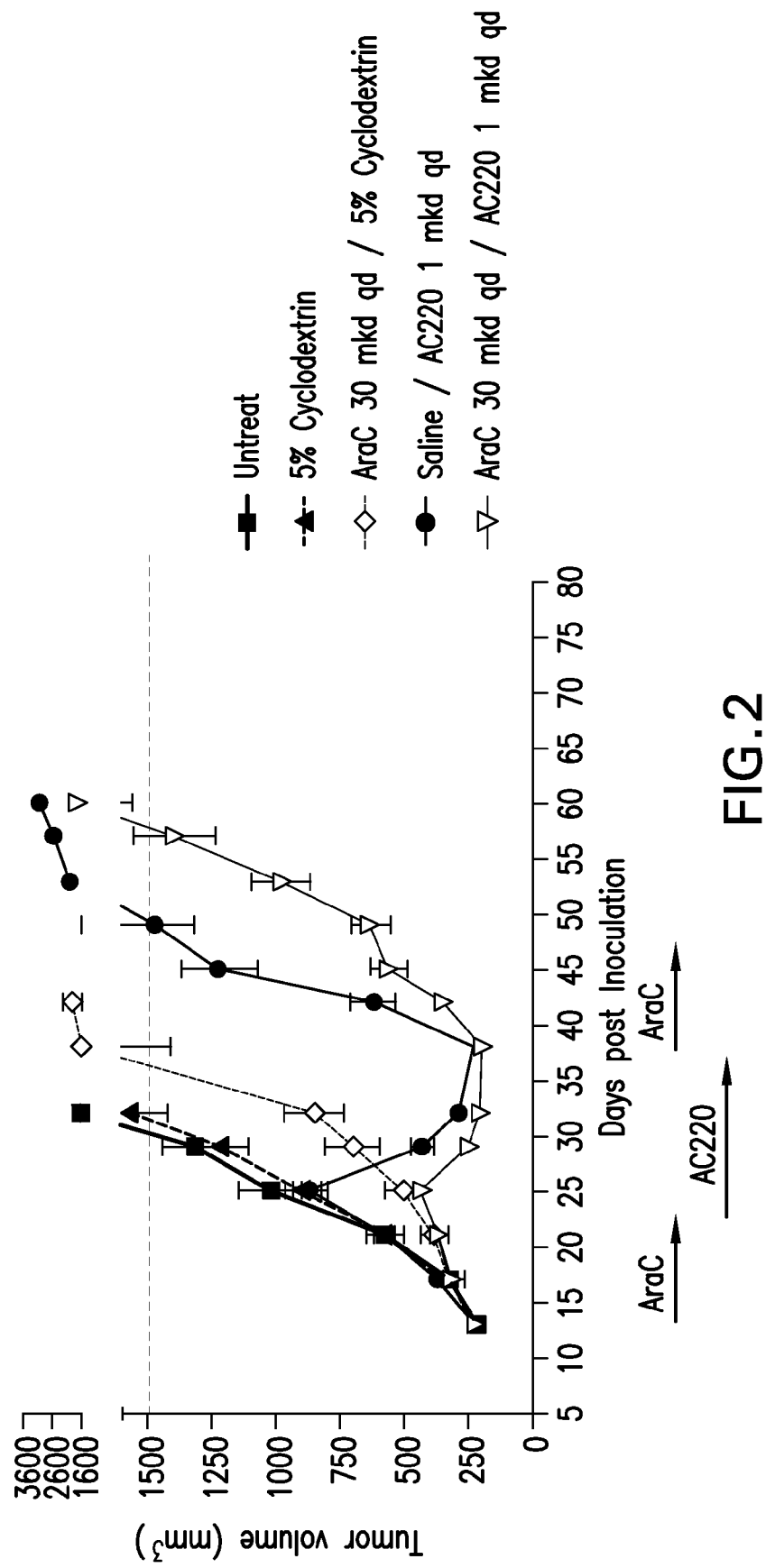
FIG. 2 is a graph showing the efficacy of AC220 plus cytarabine (sequential administration) in controlling tumor growth as compared to control, AC220 alone, and cytarabine alone.

FIG. 2 shows the flank tumor volume for the arms that received sequential administration of AC220 and cytarabine (group and 6) or AC220 and vehicle (Groups 4). Comparing Group 4 to Group 6, cytarabine does not have an antagonistic affect on AC220 and cytarabine is observed to be capable of reducing tumor burden in animals that had 2 weeks of AC220 treatment prior to second administration of Ara-C. This data suggests that the sequential administration of cytarabine first followed by AC220, may be an effective schedule for the treatment of cancer.

Example 3

In Vivo Study of AC220 Plus Aza-C in the MV4-11 Solid Tumor Flank Model

Efficacy study (in vivo) of AC220 plus Aza-C was conducted using MV4-11 solid tumor flank model in the SCID mouse. Dosing was initiated on day 15 post-inoculation with groups of 10 animals per arm. The size of the tumors averaged about 230 mm$^3$. AC220 was delivered in a formulation of 5% hydroxybetacycicodextrin aqueous solution (10 ml/kg/day, prepared weekly) at 0.5 mg/kg/day (mkd), QD, PO, and the dose was adjusted for body weight. Aza-C was delivered in a formulation of sterile saline (10 ml/kg/day, prepared in 5-day batches) at about 3 or about 1 mkd, QD, IP, and dose was adjusted for body weight. The average group starting body weight was about 20.6 g. The clinical signs and body weight were measured twice weekly. White blood cell (WBC) counts determined at the end of the Aza-C dosing period and again 7 days post drug treatment. The study was carried out in one or multiple treatment cycles with Aza-C delivered for 5 days on each 15 day cycle. As shown in Table 13 below, Aza-C was delivered either prior to or concurrent with AC220, with AC220 administered only in the first dosing cycle.

TABLE 13

Dosing Schedule of AC220 and Aza-C Efficacy Study for one cycle (15 days)

| Group | Dosing Schedule |
|---|---|
| 1. Control (untreated) | Day 1 to Day 15 |
| 2. AC220 vehicle (5% cyclodextrin) | Day 1 to Day 15 |
| 3. Aza-C alone | Aza-C (3 mkd) from Day 1 to Day 5; and 5% cyclodextrin from Day 1 to Day 15. |
| 4. Aza-C alone | Aza-C (1 mkd) from Day 1 to Day 5; and 5% cyclodextrin from Day 1 to Day 15. |
| 5. AC220 alone | Saline from Day 1 to Day 5; and AC220 (0.5 mkd) from Day 6 to Day 15. |
| 6. AC220 alone | Saline from Day 1 to Day 5; and AC220 (0.5 mkd) from Day 1 to Day 15. |
| 7. AC220 plus Aza-C (sequential) | Aza-C (3 mkd) from Day 1 to Day 5; and AC220 (0.5 mkd) from Day 6 to Day 15. |
| 8. AC220 plus Aza-C (sequential) | Aza-C (1 mkd) from Day 1 to Day 5; and AC220 (0.5 mkd) from Day 6 to Day 15. |
| 9. AC220 plus Aza-C (overlapping) | Aza-C (3 mkd) from Day 1 to Day 5; and AC220 (0.5 mkd) from Day 1 to Day 15. |
| 10. AC220 plus Aza-C (overlapping) | Aza-C (1 mkd) from Day 1 to Day 5; and AC220 (0.5 mkd) from Day 1 to Day 15. |

Figure 3:
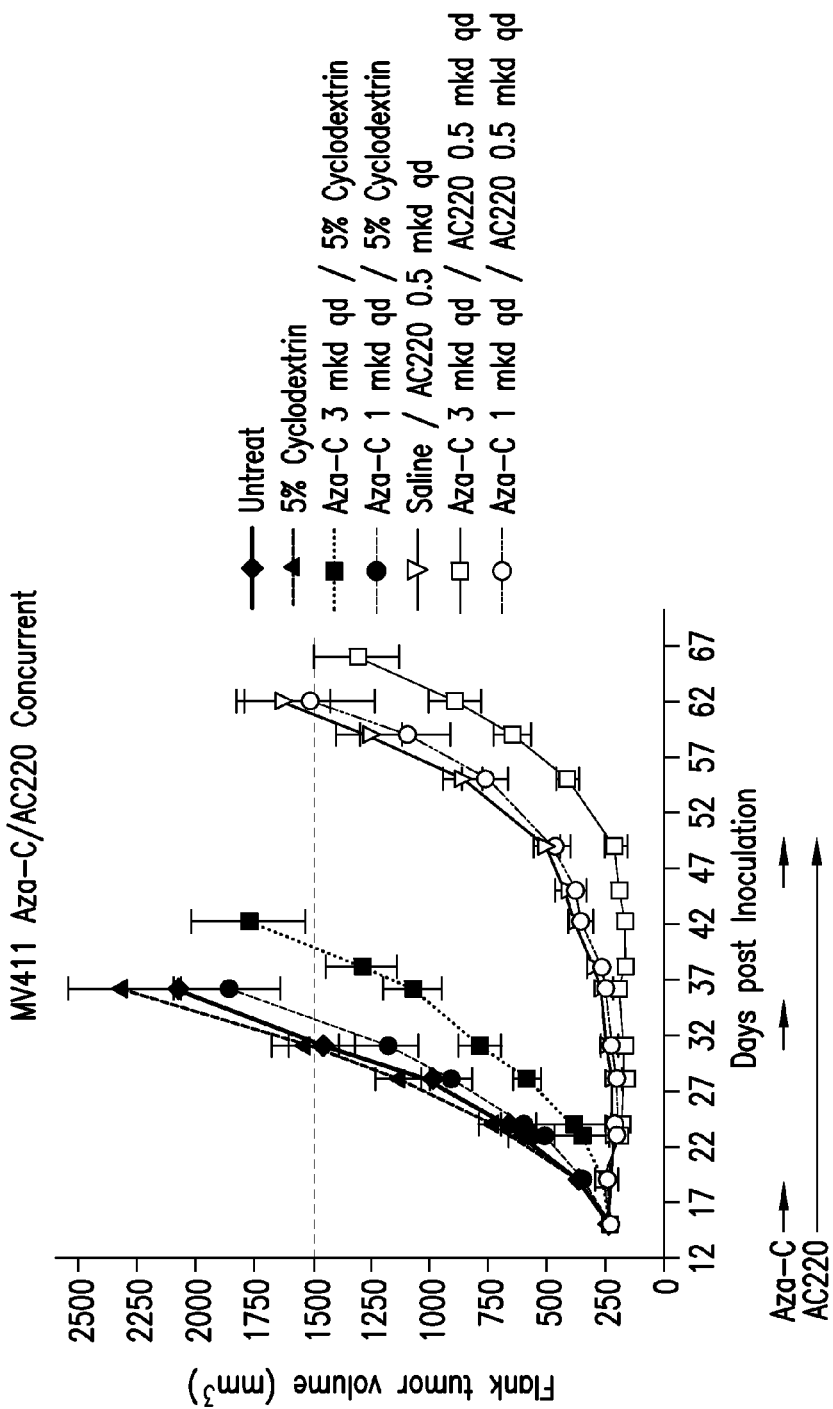
FIG. 3 is a graph showing the efficacy of AC220 plus Azacitidine (overlapping administration) in controlling tumor growth as compared to control, AC220 alone, and Azacitidine alone.

FIG. 3 shows the flank tumor volume in the arms that received the concurrent administration of AC220 and Aza-C (Groups 9 and 10) or a single drug and vehicle (Groups 3, 4 and 6). This figure shows that AC220 treatment at 15 days post inoculation results in tumor stasis and that Aza-C at the 3 mkg dose leads to approximately a 50% reduction in tumor volume. From this figure, Aza-C does not appear to antagonize the effect of AC220. Concurrent administration of Aza-C with AC220 was also associated with mild to moderate weight loss in the animals, which was no more pronounced than with Aza-c treatment alone. Based on these data, it is expected that a therapeutic window may be achieved with the concurrent administration of AC220 with Aza-C.

Figure 4:
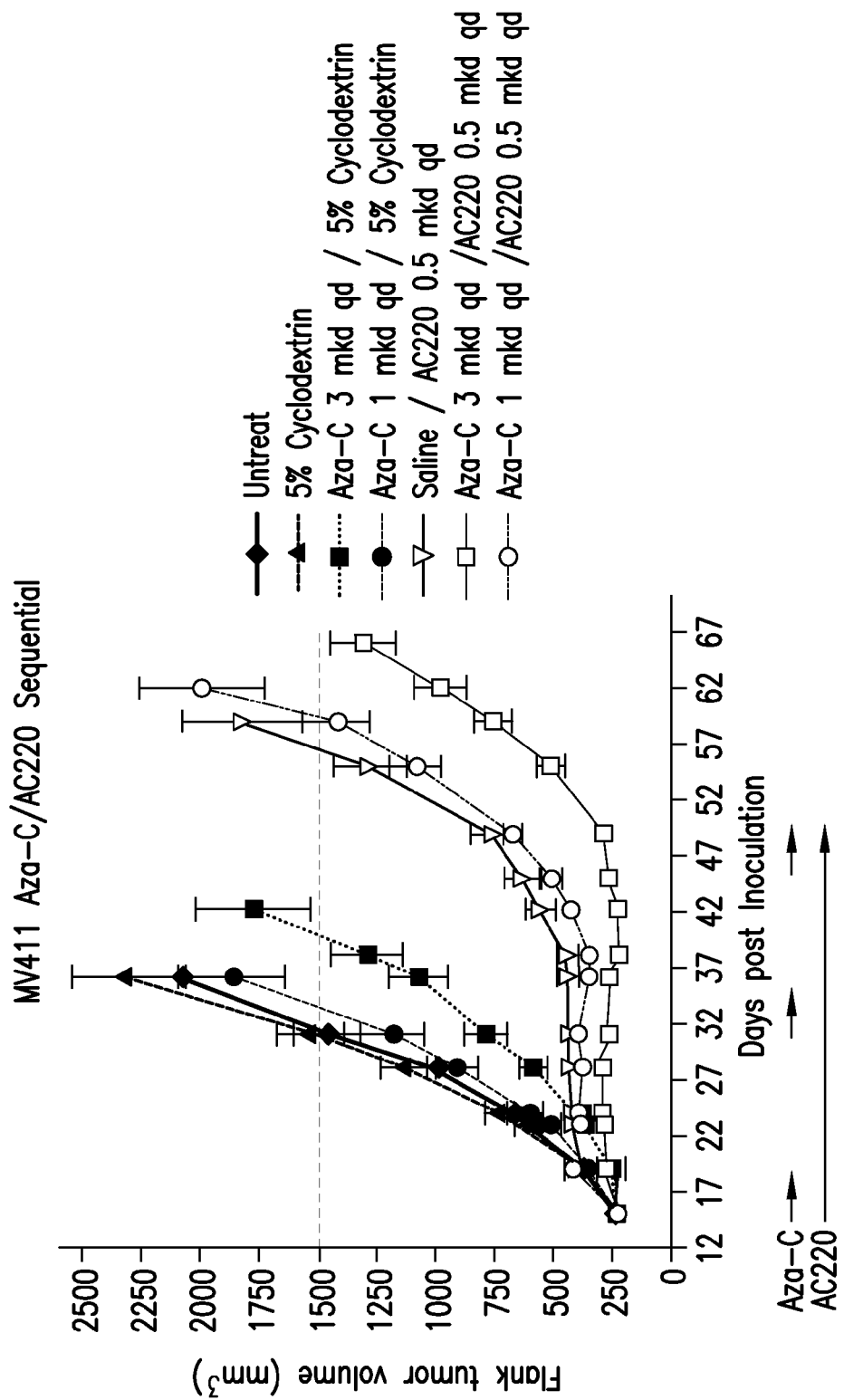
FIG. 4 is a graph showing the efficacy of AC220 plus Azacitidine (sequential administration) in controlling tumor growth as compared to control, AC220 alone, and Azacitidine alone.

FIG. 4 shows the flank tumor volume in the arms that received the sequential administration of AC220 and Aza-C (Groups 7 and 8) or single drug and vehicle (Groups 5 and 6). This figure shows that AC220 treatment at 20 days post inoculation results in tumor stasis and that Aza-C does not antagonize the effect of AC220. Sequential administration of Aza-C with AC220 was also associated with mild to moderate weight loss in the animals, which was no more pronounced than with Aza-C treatment alone. Based on these data, it is expected that a therapeutic window may be achieved with the sequential administration of AC220 with Aza-C.

Example 4

AC220 in Combination with Etoposide in Cell Viability Study

In this assay, the sequence of administration of AC220 and etoposide was examined for its cytotoxic effect. For the combination schedules tested, MV4-11 cell lines were cultured in RPMI medium with 10% fetal bovine serum and penicillin/streptomycin to a density of 3e5/mL to 1e6/mL and plated at 6e5 cells per well. Cells were exposed to two-fold serial dilutions of etoposide (at working concentrations starting from ¼× and up to 4× reported $EC_{50}$ value of 34.57 nM) in combination with two-fold serial dilutions of AC220 (at working concentrations starting from ¹⁄₁₆× and up to 8× $EC_{50}$ value of 0.35 nM), and incubated under 5% $CO_2$ at 37° C. for 24 hours in the case of simultaneous treatment of AC220 and etoposide, and incubated for a total of 72 hours in the case where cells are first pretreated with etoposide (for 24 hours) and then treated additionally with AC220 (for 48 hours). Cytotoxicity was assessed using the CellTiter-Blue™ Viability Assay (#G8081 Promega). A combination index (CI) value was generated for each combination experiment using a commercially available software program (Calcusyn; Biosoft, Manchester, United Kingdom). The interaction of the two agents was analyzed using the median effect method of Chou and Talalay (Adv. Enyme Regul. 1984; 22:27-55). The Combination index and Weighted combination index were calculated as described in Chou, *Pharmacol. Rev.* 58:621-681, 2006.

As described by Chou, supra, the ranges of CI indicate synergism, additive effect, and antagonism as follows: CI<1—synergism, CI=1—additive effect, and CI>1—antagonism.

Figure 5A:
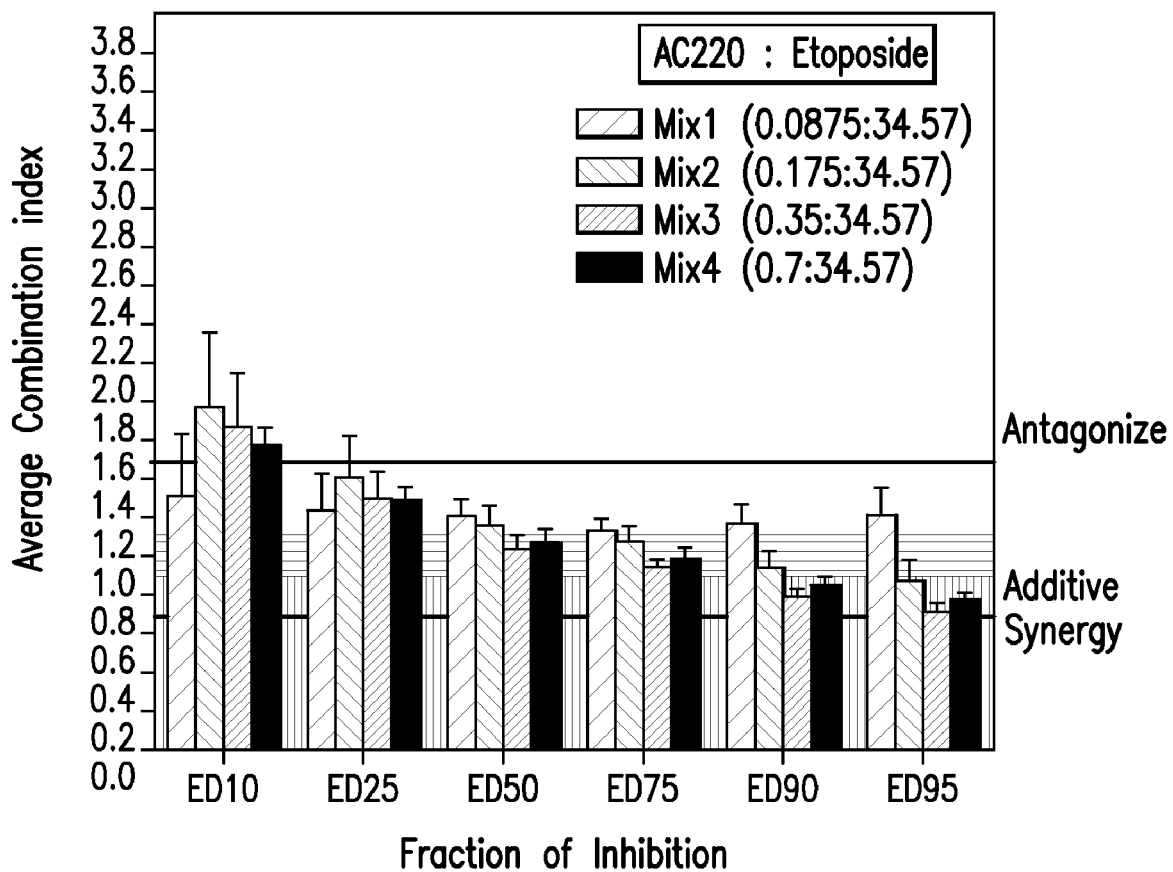
FIG. 5A shows the effect of administration of AC220 in combination with etoposide as determined at 10%, 25%, 50%, 75%, 90% and 95% inhibition of MV4-11 cell growth, when administration is concurrent.

Table 14 shows the combination index (CI) values obtained for simultaneous exposure to AC220 and etoposide. FIG. 5A highlights those specific combinations exhibiting synergy. [Table 14 shows the synergistic combinations of those cells receiving simultaneous exposure to AC220 and etoposide based on the combination index (CI) obtained for those combinations. The corresponding graph is shown in FIG. 5A.]

TABLE 14

| AC220 (nM):Etoposide (nM) | Weighted CI |
| --- | --- |
| Mixture 1 (0.0875:34.57) | 1.18 |
| Mixture 2 (0.175:34.57) | 0.96 |
| Mixture 3 (0.35:34.75) | 0.81 |
| Mixture 4 (0.7:34.57) | 0.87 |

Figure 5B:
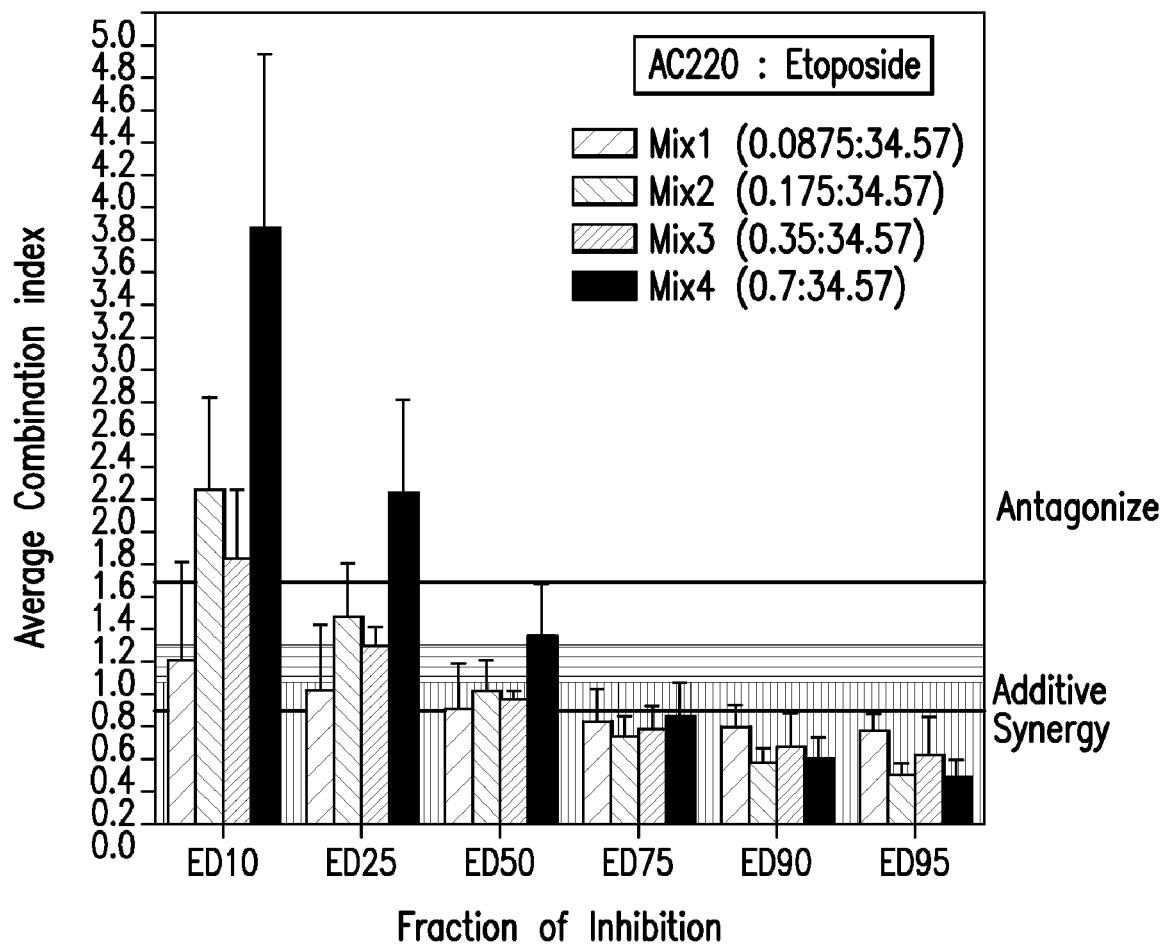
FIG. 5B shows the effect of administration of AC220 in combination with etoposide as determined at 10%, 25%, 50%, 75%, 90% and 95% inhibition of MV4-11 cell growth, when etoposide is administered 1 day before AC220.

Table 15 shows the combination index (CI) values obtained from cells receiving pretreatment with etoposide followed by the addition of AC220. FIG. 5B highlights those specific combinations exhibiting synergy. [Table 15 shows the synergistic combinations of those cells receiving pretreatment with etoposide followed by the addition of AC220, where synergy is determined by the combination index (CI) values. The corresponding graph is shown in FIG. 5B.]

TABLE 15

| AC220 (nM):Etoposide (nM) | Weighted CI |
| --- | --- |
| Mixture 1 (0.0875:34.57) | 0.61 |
| Mixture 2 (0.175:34.57) | 0.41 |
| Mixture 3 (0.35:34.75) | 0.50 |
| Mixture 4 (0.7:34.57) | 0.48 |

Example 5

AC220 in Combination with Daunorubicin in Cell Viability Study

In this assay, the sequence of administration of AC220 and daunorubicin was examined for its cytotoxic effect. For the combination schedules tested, MV4-11 cell lines were cultured in RPMI medium with 10% fetal bovine serum and penicillin/streptomycin to a density of 3e5/mL to 1e6/mL and plated at 6e5 cells per well. Cells were exposed to two-fold serial dilutions of daunorubicin (at working concentrations starting from ¼× and up to 4× reported $EC_{50}$ value of 12.65 nM) in combination with two-fold serial dilutions of AC220 (at working concentrations starting from ¹⁄₁₆× and up to 8× $EC_{50}$ value of 0.35 nM), and incubated under 5% $CO_2$ at 37° C. for 24 hours in the case of simultaneous treatment of AC220 and daunorubicin, and incubated for a total of 72 hours in the case where cells are first pretreated with daunorubicin (for 24 hours) followed by the addition of AC220 (for 48 hours) or in the case where cells are first pretreated with AC220 (for 24 hours) followed by the addition of daunorubicin (for 48 hours). Cytotoxicity was assessed using the CellTiter-Blue™ Viability Assay (#G8081 Promega). A combination index (CI) value was generated for each combination experiment using a commercially available software program (Calcusyn; Biosoft, Manchester, United Kingdom). The interaction of the two agents was analyzed using the median effect method of Chou and Talalay (Adv. Enyme Regul. 1984; 22:27-55).

Figure 6A:
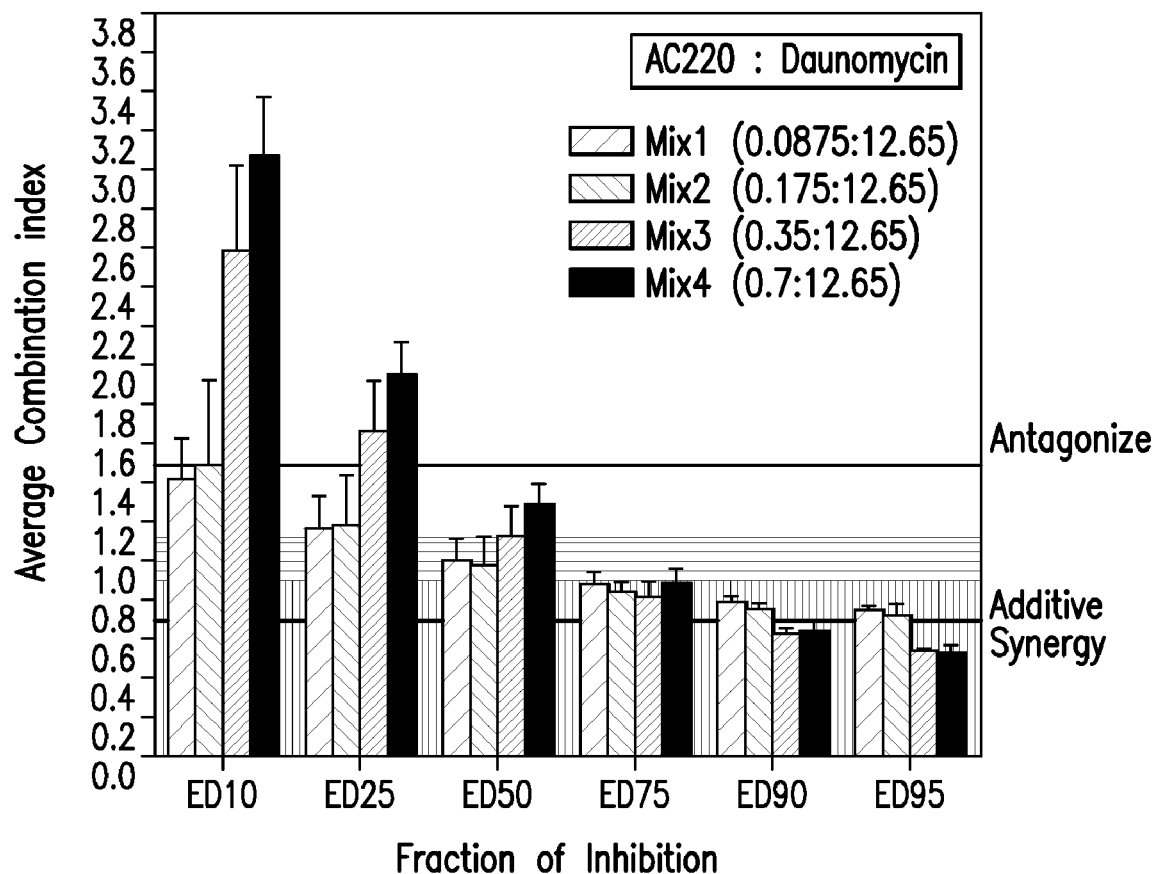
FIG. 6A shows the effect of AC220 in combination with daunorubicin as determined at 10%, 25%, 50%, 75%, 90% and 95% inhibition of MV4-11 cell growth, when administration is concurrent.

Table 16 shows the combination index obtained for the simultaneous exposure of cells to AC220 and daunorubicin. The corresponding graph is shown in FIG. 6A.

TABLE 16

| AC220 (nM):daunorubicin (nM) | Weighted CI |
| --- | --- |
| Mixture 1 (0.0875:12.65) | 0.81 |
| Mixture 2 (0.175:12.65) | 0.77 |
| Mixture 3 (0.35:12.65) | 0.67 |
| Mixture 4 (0.7:12.65) | 0.70 |

Figure 6B:
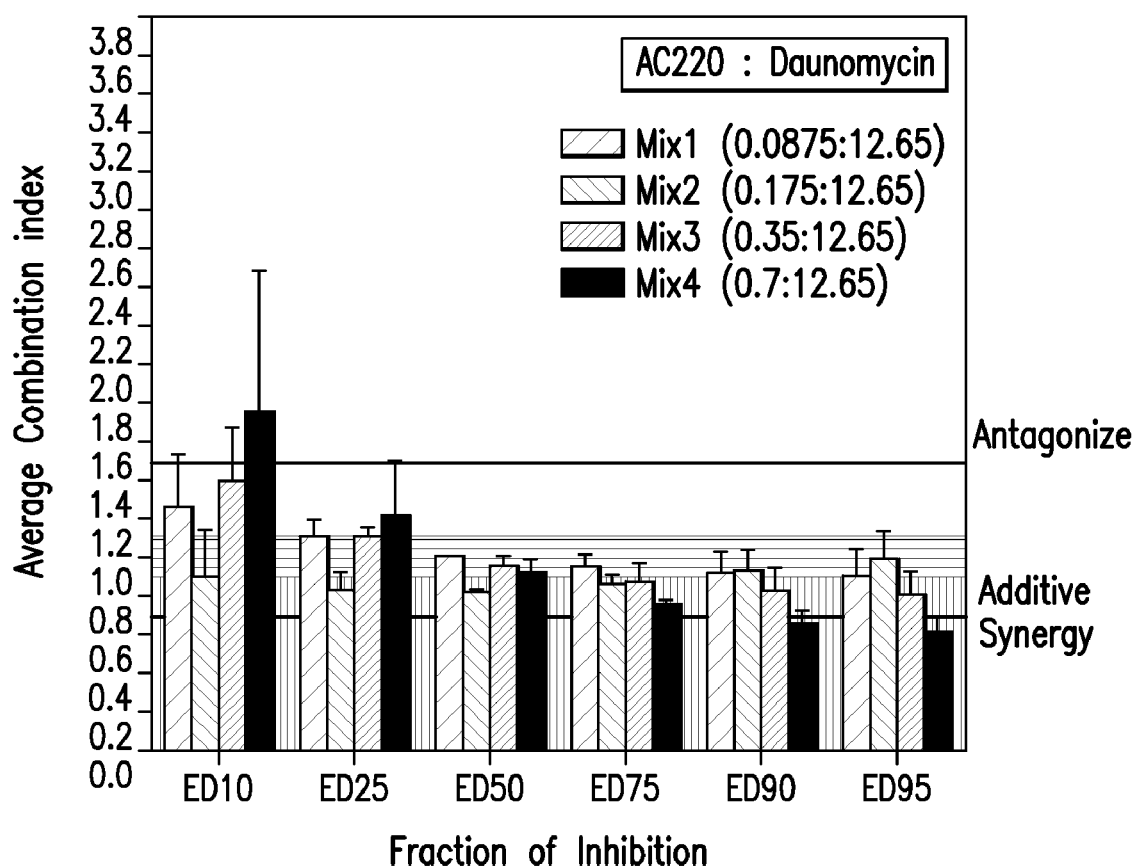
FIG. 6B shows the effect of administration of AC220 in combination with daunorubicin as determined at 10%, 25%, 50%, 75%, 90% and 95% inhibition of MV4-11 cell growth, when daunorubicin is administered 1 day before AC220.

Table 17 shows the combination index (CI) values obtained from cells receiving pretreatment with daunorubicin followed by the addition of AC220. The corresponding graph is shown in FIG. 6B.

TABLE 17

| AC220 (nM):daunorubicin (nM) | Weighted CI |
| --- | --- |
| Mixture 1 (0.0875:12.65) | 0.93 |
| Mixture 2 (0.175:12.65) | 0.92 |
| Mixture 3 (0.35:12.65) | 0.84 |
| Mixture 4 (0.7:12.65) | 0.69 |

Figure 6C:
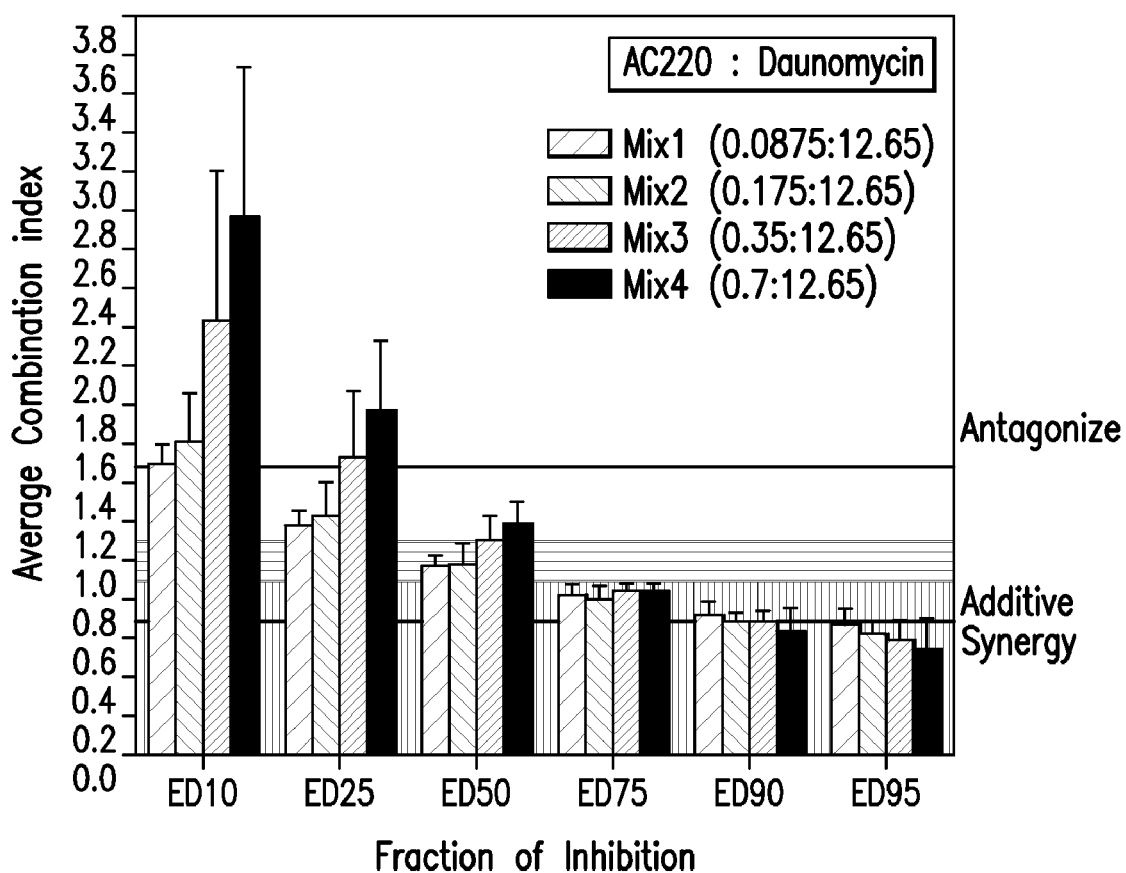
FIG. 6C shows the effect of administration of AC220 in combination with daunorubicin as determined at 10%, 25%, 50%, 75%, 90% and 95% inhibition of MV4-11 cell growth, when daunorubicin is administered 1 day after AC220.

Table 18 shows the combination index (CI) values obtained from cells receiving treatment with AC220 followed by treatment with daunorubicin. The corresponding graph is shown in FIG. 6C.

TABLE 18

| AC220 (nM):daunorubicin (nM) | Weighted CI |
| --- | --- |
| Mixture 1 (0.0875:12.65) | 0.75 |
| Mixture 2 (0.175:12.65) | 0.71 |
| Mixture 3 (0.35:12.65) | 0.72 |
| Mixture 4 (0.7:12.65) | 0.70 |

Example 6

AC220 in Combination with Cladribine in Cell Viability Study

In this assay, the sequence of administration of AC220 and cladribine was examined for its cytotoxic effect. For the combination schedules tested, MV4-11 cell lines were cultured in Iscove medium with 10% fetal bovine serum and penicillin/ streptomycin to a density of 3e5/mL and plated at 6e4 cells per well. Cells were exposed to two-fold serial dilutions of cladribine (at working concentrations starting from ¼× and up to 4× reported $EC_{50}$ value of 16.2 nM) in combination with two-fold serial dilutions of AC220 (at working concentrations starting from ¹⁄₁₆× and up to 8× $EC_{50}$ value of 0.35 nM), and incubated under 5% $CO_2$ at 37° C. for 72 hours in the case of simultaneous treatment of AC220 and cladribine, and incubated for a total of 72 hours in the case where cells are first pretreated with cladribine (for 24 hours) and then treated additionally with AC220 (for 48 hours) or where the cells are first pretreated with AC220 (for 24 hours) and then treated additionally with cladribine (for 48 hours). Cytotoxicity was assessed using the CellTiter-Blue™ Viability Assay (#G8081 Promega). A combination index (CI) value was generated for each combination experiment using a commercially available software program (Calcusyn; Biosoft, Manchester, United Kingdom). The interaction of the two agents was analyzed using the median effect method of Chou and Talalay (Adv. Enyme Regul. 1984; 22:27-55).

Table 19 shows the weighted combination index (CI) values obtained for simultaneous exposure to AC220 and cladribine.

TABLE 19

| AC220 (nM):cladribine (nM) | Weighted CI |
|---|---|
| Mixture 1 (0.0875:16.2) | 0.96 |
| Mixture 2 (0.175:16.2) | 0.99 |
| Mixture 3 (0.35:16.2) | 0.91 |
| Mixture 4 (0.7:16.2) | 0.91 |

Table 20 shows the weighted combination index (CI) values obtained from cells receiving pretreatment with cladribine followed by the addition of AC220.

TABLE 20

| AC220 (nM):cladribine (nM) | Weighted CI |
|---|---|
| Mixture 1 (0.0875:16.2) | 1.07 |
| Mixture 2 (0.175:16.2) | 1.01 |
| Mixture 3 (0.35:16.2) | 1.09 |
| Mixture 4 (0.7:16.2) | 1.24 |

Table 21 shows the weighted combination index (CI) values obtained for cells receiving pretreatment with AC220 followed by the addition of cladribine.

TABLE 21

| AC220 (nM):cladribine (nM) | Weighted CI |
|---|---|
| Mixture 1 (0.0875:16.2) | 0.90 |
| Mixture 2 (0.175:16.2) | 0.81 |
| Mixture 3 (0.35:16.2) | 0.89 |
| Mixture 4 (0.7:16.2) | 0.67 |

Example 7

AC220 in Combination with Cytarabine in Cell Viability Study

In this assay, the sequence of administration of AC220 and cytarabine was examined for its cytotoxic effect. For the combination schedules tested, MV4-11 cell lines were cultured in Iscove medium with 10% fetal bovine serum and penicillin/streptomycin to a density of 3e5/mL and plated at 6e4 cells per well. Cells were exposed to two-fold serial dilutions of cytarabine (at working concentrations starting from ¼× and up to 4× reported $EC_{50}$ value of 380 nM) in combination with two-fold serial dilutions of AC220 (at working concentrations starting from ¹⁄₁₆× and up to 8× $EC_{50}$ value of 0.35 nM), and incubated under 5% $CO_2$ at 37° C. for 72 hours in the case of simultaneous treatment of AC220 and cytarabine, and incubated for a total of 72 hours in the case where cells are first pretreated with cytarabine (for 24 hours) and then treated additionally with AC220 (for 72 hours) or where the cells are first pretreated with AC220 (for 24 hours) and then treated additionally with cytarabine (for 72 hours). Cytotoxicity was assessed using the CellTiter-Blue™ Viability Assay (#G8081 Promega). A combination index (CI) value was generated for each combination experiment using a commercially available software program (Calcusyn; Biosoft, Manchester, United Kingdom). The interaction of the two agents was analyzed using the median effect method of Chou and Talalay (Adv. Enyme Regul. 1984; 22:27-55).

Table 22 shows the weighted combination index (CI) values obtained for cells receiving simultaneous exposure to AC220 and cytarabine.

TABLE 22

| AC220 (nM):cytarabine (nM) | Weighted CI |
|---|---|
| Mixture 1 (0.0875:380) | 0.71 |
| Mixture 2 (0.175:380) | 0.66 |
| Mixture 3 (0.35:380) | 0.63 |
| Mixture 4 (0.7:380) | 0.68 |

Table 23 shows the weighted combination index (CI) values obtained for cells receiving pretreatment with cytarabine followed by the addition of AC220.

TABLE 23

| AC220 (nM):cytarabine (nM) | Weighted CI |
|---|---|
| Mixture 1 (0.0875:380) | 0.77 |
| Mixture 2 (0.175:380) | 0.78 |
| Mixture 3 (0.35:380) | 0.61 |
| Mixture 4 (0.7:380) | 0.56 |

Table 24 shows the weighted combination index (CI) values obtained for cells receiving pretreatment with AC220 followed by the addition of cytarabine.

TABLE 24

| AC220 (nM):cytarabine (nM) | Weighted CI |
|---|---|
| Mixture 1 (0.0875:380) | 0.93 |
| Mixture 2 (0.175:380) | 0.73 |
| Mixture 3 (0.35:380) | 1.01 |
| Mixture 4 (0.7:380) | 1.15 |

Example 8

AC220 in Combination with PI3K Inhibitor GDC-0941 in Cell Viability Study

In this assay, the sequence of administration of AC220 and the PI3K inhibitor GDC-0941 was examined for its cytotoxic effect. For the combination schedules tested, SEM-K2 cell lines were cultured in RPMI medium with 10% fetal bovine serum and penicillin/streptomycin to a density of 3e5/mL to 1e6/mL and plated at 6e4 cells per well. Initially, EC50 values were calculated for GDC-0941 and AC220 independently, for each treatment schedule of each drug used in the combinations. Cells were exposed to two-fold serial dilutions of GDC-0941 (at working concentrations starting from ¼× and up to 4× the calculated $EC_{50}$ value of GDC-0941 in combination with two-fold serial dilutions of AC220 (at working concentrations starting from ¹⁄₁₆× and up to 8× the calculated $EC_{50}$ value) and incubated for a total of four days under 5% $CO_2$ at 37° C. according to one of the following schedules: (i) incubated with AC220 and GDC-0941 for a period of four days in the case of simultaneous treatment of AC220 and GDC-0941; (ii) incubated with only GDC-0941 for the first 24 hours, followed by incubation with both AC220 and GDC-0941 in the case of semi-concurrent administration starting with GDC-0941; (iii) incubated with GDC-0941 for the first 24 hours followed by the removal of GDC-0941 and addition of AC220 in the case of sequential administration beginning with GDC-0941; (iv) incubated with only AC220 for the first 24 hours followed by concurrent administration of AC220 and GDC-0941 in the case of semi-concurrent administration starting with AC220; and finally, (v) incubated with AC220 only for the first 24 hours followed by the removal of AC220 and addition of GDC-0941 in the case of sequential administration beginning with AC220. Cytotoxicity was assessed using the CellTiter-Blue™ Viability Assay (#G8081 Promega). A combination index (CI) value was generated for each combination experiment using a commercially available software program (Calcusyn; Biosoft, Manchester, United Kingdom). The interaction of the two agents was analyzed using the median effect method of Chou and Talalay (Adv. Enyme Regul. 1984; 22:27-55).

Table 25 shows the weighted combination index (CI) values obtained for cells receiving the various schedules of AC220 and GDC-0941.

TABLE 25

| Schedule | Weighted CI |
| --- | --- |
| Semi-concurrent - GDC-0941 first | 0.35 |
| Sequential - GDC-0941 first | 0.76 |
| Concurrent | 0.49 |
| Semi-concurrent - AC220 first | 0.21 |
| Sequential - AC220 first | 0.16 |

Example 9

AC220 in Combination with Daunorubicin in the MV4-11 Solid Tumor Model

Figure 7:
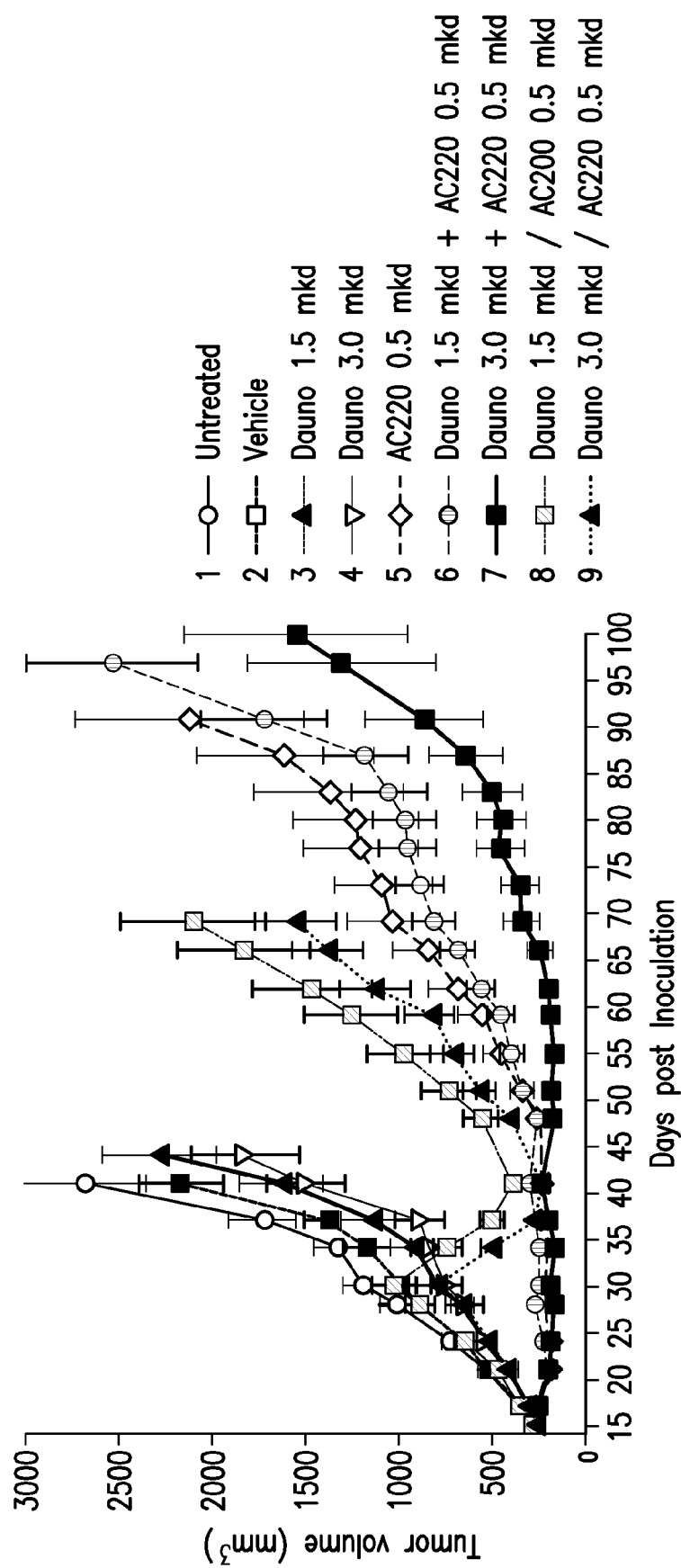
FIG. 7 is a graph showing the efficacy of AC220 plus daunorubicin in controlling tumor growth in a MV4-11 solid tumor model as compared to control, AC220 alone, and daunorubicin alone.

An in vivo study of AC220 plus daunorubicin was conducted using MV4-11 solid tumor flank model in the C.B-17 SCID mouse (Harlan Laboratories). Female SCID mice were inoculated on the right flank with 200 µL of a 50/50 mixture of MV4-11 cells and Matrigel. 5e6 cells were inoculated per animal. Dosing was initiated on day 15 with nine groups of 10 animals each. The average tumor volume was about 274 mm³. The average starting body weight was about 20.8 g. Daunorubicin (Sigma Aldrich) was delivered every 5 days intravenously (Q5D, IV) in a formulation of sterile saline at 2.5 mg/mL, with the dose adjusted to body weight. AC220 was delivered in a formulation of 5% hydroxypropylbetacyclodextrin aqueous solution at 0.5 mg/kg/day (mkd), QD, PO, and the dose was adjusted for body weight. The dosing schedule was as shown in Table 26, and body weight and clinical signs were measured twice weekly. Complete blood cell counts were determined on day 20, day 31 and day 37. On day 31 and onwards, Groups 8 and 9 and all other groups receiving daily AC220 continued to receive AC220 until the tumor volume had reached at least 1500 mm³. FIG. 7 shows median tumor growth curves generated from this experiment.

TABLE 26

| Treatment group | Dosing Schedule (days refer to days post inoculation with MV4-11) |
| --- | --- |
| 1. untreated | n/a |
| 2. vehicles (saline + 5% cyclodextrin) | Saline IV on d15; d20; d25; d30<br>Cyclodextrin PO, daily d1-30 |
| 3. 1.5 mg/kg/day daunorubicin plus 5% cyclodextrin vehicle | Daunorubicin IV on d15; d20; d25; d30<br>Cyclodextrin PO, daily d1-30 |
| 4. 3 mg/kg/day daunorubicin plus 5% cyclodextrin vehicle | Daunorubicin IV on d15; d20; d25; d30<br>Cyclodextrin PO, daily d1-30 |
| 5. 0.5 mg/kg AC220 plus saline vehicle | Saline IV on d15; d20; d25; d30<br>AC220 PO, daily d1-30 |
| 6. 1.5 mg/kg/day daunorubicin plus 0.5 mg/kg AC220 continuous | Daunorubicin IV on d15; d20; d25; d30<br>AC220 PO, daily d1-30 |
| 7. 3 mg/kg/day daunorubicin plus 0.5 mg/kg AC220 continuous | Daunorubicin IV on d15; d20; d25; d30<br>AC220 PO, daily d1-30 |
| 8. 1.5 mg/kg/day daunorubicin plus 0.5 mg/kg AC220 post | Daunorubicin IV on d15; d20; d25; d30<br>AC220 PO, daily starting d31 |
| 9. 3 mg/kg/day daunorubicin plus 0.5 mg/kg AC220 post | Daunorubicin IV on d15; d20; d25; d30<br>AC220 PO, daily starting d31 |

FIG. 7 demonstrates that concurrent administration of AC220 and daunorubicin (Groups 6 and 7) provides tumor growth regression not found in group receiving sequential administration of AC220 and daunorubicin (Groups 8 and 9). Administration of AC220 following daunorubicin on Day 31 initially leads to tumor growth regression in Groups 8 and 9, but overall, the groups originally receiving concurrent therapy (Groups 6 and 7) exhibit the greatest delay in tumor growth.

A similar in vivo study examining the effects of concurrent and sequential administration of AC220 and daunorubicin has been initiated in the MOLM-14 leukemia model in NOD/SCID mice. While the MV4-11 cell line is homozygous for the FLT3 ITD mutation and responsive to AC220, the MOLM-14 is a cell line that is heterozygous for the FLT3 ITD mutation and which is less responsive to AC220 and therefore represents a disease model that will not be overpowered by the effects of AC220 and hence may be a better model for testing AC220 combination effects.

The examples set forth above are provided to give those of ordinary skill in the art with a complete disclosure and description of how to make and use the claimed embodiments, and are not intended to limit the scope of what is disclosed herein. Modifications that are obvious to persons of skill in the art are intended to be within the scope of the following claims. All publications, patents, and patent applications cited in this specification are incorporated herein by reference as if each such publication, patent or patent application were specifically and individually indicated to be incorporated herein by reference.

What is claimed is:

1. A method of treating a proliferative disease in a mammal, which comprises administering to the mammal having or suspected to have the proliferative disease, a therapeutically effective amount of: (a) a compound of structural formula A

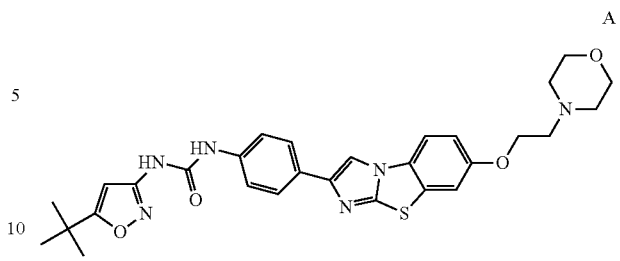

or a salt thereof, and (b) a second agent selected from a nucleoside analog, wherein the nucleoside analog is a neoplastic cell antimetabolite; an anthracycline and a topoisomerase inhibitor, or a combination thereof.

2. A method of treating a proliferative disease in a mammal, which comprises administering to the mammal having or suspected to have the proliferative disease, a therapeutically effective amount of a compound of Formula A

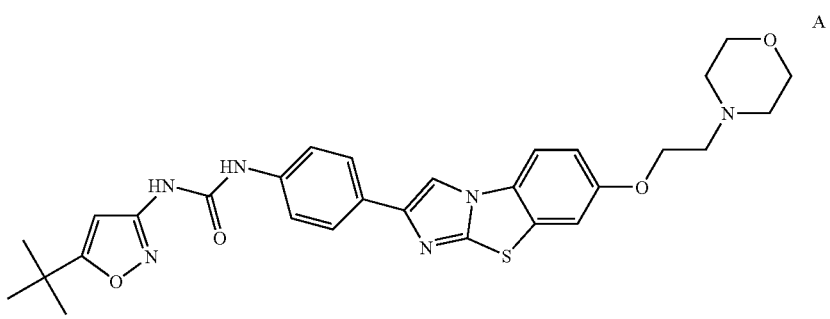 [SMILES: CC(C)(C)c1cc(NC(=O)Nc2ccc(-c3cn4c(n3)sc3cc(OCCN5CCOCC5)ccc34)cc2)no1]

or a pharmaceutically acceptable salt thereof, and a therapeutically acceptable dose of a second agent selected from an anthracycline and a topoisomerase inhibitor.

3. A method of treating a hematological neoplastic disease comprising co-administering to a patient in need thereof a therapeutically effective amount of (a) a nucleoside analog, wherein the nucleoside analog is a neoplastic cell antimetabolite; and (b) a compound of structural formula A:

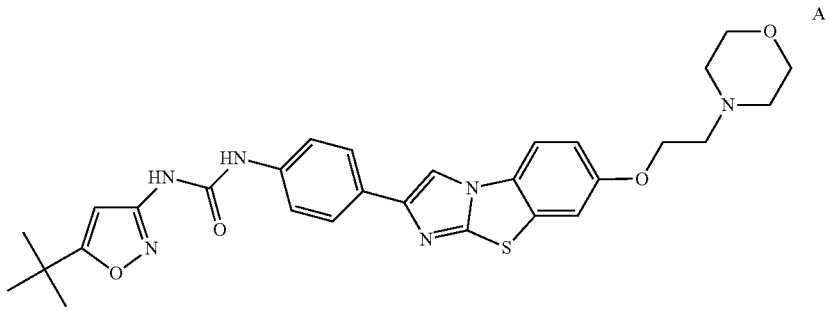 [SMILES: CC(C)(C)c1cc(NC(=O)Nc2ccc(-c3cn4c(n3)sc3cc(OCCN5CCOCC5)ccc34)cc2)no1]

or a salt thereof.

4. The method of claim 1, wherein the compound of formula A or a pharmaceutically acceptable salt thereof is administered in a dose of at least 12 mg per day.

5. The method of claim 1, wherein the compound of formula A or a pharmaceutically acceptable salt thereof is administered in a dose of about 27 to 1000 mg per day.

6. The method of claim 1, wherein the compound of formula A or a pharmaceutically acceptable salt thereof is administered in a dose of about 40 to 450 mg per day.

7. The method of claim 1, wherein the compound of formula A or a pharmaceutically acceptable salt thereof is administered in a dose of about 12, about 18, about 27, about 40, about 60, about 90, about 135, about 200, or about 450 mg per day.

8. The method of claim 1, wherein the compound of formula A, or a pharmaceutically acceptable salt thereof, is administered once per day for one week, two weeks, or three weeks.

9. The method of claim 1, wherein the compound of formula A, or a pharmaceutically acceptable salt thereof is administered once per day for fourteen days.

10. The method of claim 1, wherein the second agent is a nucleoside analog.

11. The method of claim 10, wherein the nucleoside analog comprises a phosphate moiety.

12. The method of claim 11, wherein the nucleoside analog is fludarabine phosphate.

13. The method of claim 10, wherein the nucleoside analog does not comprise a phosphate moiety.

14. The method of claim 13, wherein the nucleoside analog is selected from the group consisting of decitabine, azacitidine, clofarabine, cytarabine, cladribine and a combination thereof.

15. The method of claim 10, wherein the nucleoside analog is a DNA methylation inhibitor.

16. The method of claim 15, wherein the nucleoside analog is decitabine, azacitidine, or a combination thereof.

17. The method of claim 1, wherein the second agent is selected from etoposide, cytarabine, clofarabine, idarubicin and daunorubicin, or a combination thereof.

18. The method of claim 17, wherein cytarabine is administered in a dose of about 100 mg/m$^2$/day, 200 mg/m$^2$/day, 750 mg/m$^2$/day, 1 g/m$^2$/day or 3 g/m$^2$/day.

19. The method of claim 18 further comprising co-administering an anthracycline.

20. The method of claim 1, wherein the anthracycline is selected from the group consisting of doxorubicin, daunorubicin, vulrubicin, idarubicin, epirubicin, and a combination thereof.

21. The method of claim 20, wherein daunorubicin is administered in a dose of about 25, 30, 45, or 60 mg/m$^2$/day.

22. The method of claim 17, wherein etoposide is administered in a dose from about 10 mg/m$^2$/day to about 150 mg/m$^2$/day.

23. The method of claim 17, wherein the dose of etoposide is about 35, 50, 100 or 150 mg/m$^2$/day.

24. The method of claim 22, wherein the compound of formula A, or a pharmaceutically acceptable salt thereof is administered once a day for one week, two weeks, three weeks, four weeks or five weeks and etoposide is administered once a day for 5 days.

25. The method of claim 22, wherein the compound of formula A, or a pharmaceutically acceptable salt thereof is administered once a day for one week, two weeks, three weeks, four weeks or five weeks and etoposide is administered once a day on days 1, 3, and 5.

26. The method of claim 17, wherein the compound of formula A, or a pharmaceutically acceptable salt thereof is administered once a day for one week, two weeks, three weeks, four weeks or five weeks and cytarabine is administered once a day for 7 days.

27. The method of claim 17, wherein the compound of formula A, or a pharmaceutically acceptable salt thereof is administered once a day for one week, two weeks, three weeks, four weeks or five weeks and cytarabine is administered once a day on days 1, 3 and 5.

28. The method of claim 1, wherein the compound of formula A, or a pharmaceutically acceptable salt thereof is administered once a day for one week, two weeks, three weeks, four weeks or five weeks and daunorubicin is administered once a day on days 1, 2 and 3.

29. The method of claim 1, wherein the compound of formula A, or a pharmaceutically acceptable salt thereof is administered once a day for one week, two weeks, three weeks, four weeks or five weeks, cytarabine is administered once a day for 7 days and daunorubicin is administered once a day on days 1, 2 and 3.

30. The method of claim 1, wherein the proliferative disease is cancer.

31. The method of claim 29, wherein the cancer is a leukemia.

32. The method of claim 31, wherein the leukemia is an acute leukemia.

33. The method of claim 31, wherein the leukemia is acute myeloid leukemia.

34. The method of claim 31, wherein the leukemia is promyelocytic leukemia.

35. The method of claim 31, wherein the leukemia is acute lymphoblastic leukemia.

36. The method of claim 31, wherein the leukemia is positive for the FLT3-ITD mutation.

37. The method of claim 31, wherein the leukemia is relapsed or refractory.

38. The method of claim 31, wherein the leukemia is a drug-resistant leukemia.

39. The method of claim 38, wherein the drug-resistant leukemia is resistant to a FLT3 kinase inhibitor.

40. The method of claim 30, wherein the cancer is a solid tumor.

41. The method of claim 40, wherein the cancer is a bladder cancer, breast cancer, cervical cancer, CNS cancer, colon cancer, esophageal cancer, head and neck cancer, liver cancer, lung cancer, nasopharyngeal cancer, neuroendocrine cancer, ovarian cancer, pancreatic cancer, prostate cancer, renal cancer, salivary gland cancer, small cell lung cancer, skin cancer, stomach cancer, testicular cancer, thyroid cancer, uterine cancer, or hematologic malignancy.

42. The method of claim 1, wherein the compound of formula A, or a pharmaceutically acceptable salt thereof is administered orally.

43. The method of claim 1, wherein the compound of formula A, or a pharmaceutically acceptable salt thereof is administered parenterally.

44. The method of claim 1, wherein the compound of formula A, or a pharmaceutically acceptable salt thereof is administered intravenously.

* * * * *